US010925541B2

(12) United States Patent
Tokko et al.

(10) Patent No.: US 10,925,541 B2
(45) Date of Patent: Feb. 23, 2021

(54) BODILY INFORMATION MEASUREMENT APPARATUS

(71) Applicant: OMRON HEALTHCARE Co., Ltd., Kyoto (JP)

(72) Inventors: Yoshihide Tokko, Kyoto (JP); Masayuki Fukutsuka, Kyoto (JP); Yuma Adachi, Kyoto (JP); Kengo Nishiyama, Kyoto (JP); Sunao Ouchida, Osaka (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 0 days.

(21) Appl. No.: 15/917,516

(22) Filed: Mar. 9, 2018

(65) Prior Publication Data

US 2018/0192947 A1 Jul. 12, 2018

Related U.S. Application Data

(63) Continuation of application No. PCT/JP2016/089051, filed on Dec. 28, 2016.

(30) Foreign Application Priority Data

Jan. 4, 2016 (JP) .............................. JP2016-000259
Jun. 9, 2016 (JP) .............................. JP2016-115685

(51) Int. Cl.
*A61B 5/00* (2006.01)
*A61B 5/022* (2006.01)
*B29C 65/16* (2006.01)
*B29C 65/00* (2006.01)
(Continued)

(52) U.S. Cl.
CPC .............. *A61B 5/681* (2013.01); *A61B 5/022* (2013.01); *A61B 5/0205* (2013.01);
(Continued)

(58) Field of Classification Search
None
See application file for complete search history.

(56) References Cited

U.S. PATENT DOCUMENTS 2,429,950 A * 10/1947 Weber ...................... A44C 5/24
224/176
2,595,264 A * 5/1952 Jespersen ............. A44B 11/006
24/176

(Continued)

FOREIGN PATENT DOCUMENTS

JP    S63-200144 A    8/1988
JP    H06-11701 A     1/1994

(Continued)

OTHER PUBLICATIONS

International Search Report issued in Application No. PCT/JP2016/089051, dated Mar. 21, 2017 (2 pages).

(Continued)

*Primary Examiner* — Jacqueline Cheng
*Assistant Examiner* — Jairo H Portillo
(74) *Attorney, Agent, or Firm* — Osha Bergman Watanabe & Burton LLP

(57) ABSTRACT

A bodily information measurement apparatus includes: a belt for wrapping around a measurement site; a main body arranged at a base end portion in a lengthwise direction of the belt and on which an element that measures bodily information is mounted; and a buckle for joining the base end portion and a leading end portion of the belt such that the belt forms a loop shape. The buckle includes first and second plate frame members, which include, respectively, first and second opening portions that penetrate through the respective members with respect to a plate surface. In a state in which the inner surface of the main body and the first and second plate frame members of the buckle are folded in so as to overlap, the first and second opening portions of the (Continued)

first and second plate frame members, respectively, are continuous in a thickness direction of the main body.

15 Claims, 46 Drawing Sheets

(51) Int. Cl.
| | |
|---|---|
| *B29C 70/84* | (2006.01) |
| *A61B 5/0205* | (2006.01) |
| *A61B 5/024* | (2006.01) |
| *B29L 31/34* | (2006.01) |
| *A61B 5/0235* | (2006.01) |
| *A61B 5/021* | (2006.01) |
| *A61B 5/1455* | (2006.01) |

(52) U.S. Cl.
CPC ...... *A61B 5/02233* (2013.01); *A61B 5/02438* (2013.01); *A61B 5/6824* (2013.01); *A61B 5/6843* (2013.01); *B29C 65/1635* (2013.01); *B29C 66/1122* (2013.01); *B29C 70/84* (2013.01); *A61B 5/0235* (2013.01); *A61B 5/02108* (2013.01); *A61B 5/02225* (2013.01); *A61B 5/1455* (2013.01); *A61B 2562/0247* (2013.01); *A61B 2562/12* (2013.01); *A61B 2562/166* (2013.01); *A61B 2562/222* (2013.01); *B29L 2031/3481* (2013.01)

(56) References Cited

U.S. PATENT DOCUMENTS

| | | | | |
|---|---|---|---|---|
| 3,613,183 A * | 10/1971 | Yuen | ...... | A44C 5/145 |
| | | | | 24/265 H |
| 4,896,676 A * | 1/1990 | Sasaki | ...... | A61B 5/02241 |
| | | | | 600/494 |
| 6,175,729 B1 * | 1/2001 | He | ...... | A44C 5/24 |
| | | | | 343/718 |
| 6,314,058 B1 * | 11/2001 | Lee | ...... | A61B 5/02141 |
| | | | | 368/10 |
| 2006/0272134 A1 * | 12/2006 | Turuani | ...... | A44C 5/24 |
| | | | | 24/71 J |
| 2010/0302914 A1 * | 12/2010 | Faucher | ...... | A44C 5/147 |
| | | | | 368/282 |
| 2015/0289607 A1 * | 10/2015 | Lee | ...... | A44C 5/2071 |
| | | | | 224/219 |
| 2015/0342308 A1 * | 12/2015 | Wilson | ...... | A45F 5/00 |
| | | | | 224/219 |

FOREIGN PATENT DOCUMENTS

| | | |
|---|---|---|
| JP | H09-285453 A | 11/1997 |
| JP | 2000-155037 A | 6/2000 |
| JP | 2010-051364 A | 3/2010 |
| JP | 2014-018357 A | 2/2014 |
| JP | 2015-142713 A | 8/2015 |
| JP | 2017-027594 A | 2/2017 |
| WO | WO-2015137599 A1 * | 9/2015 ............. A44C 5/147 |

OTHER PUBLICATIONS

Written Opinion issued in Application No. PCT/JP2016/089051, dated Mar. 21, 2017 (5 pages).

Decision to Grant a Patent issued in corresponding Japanese Application No. 2016-115685, dated Jun. 6, 2017 (6 pages).

* cited by examiner

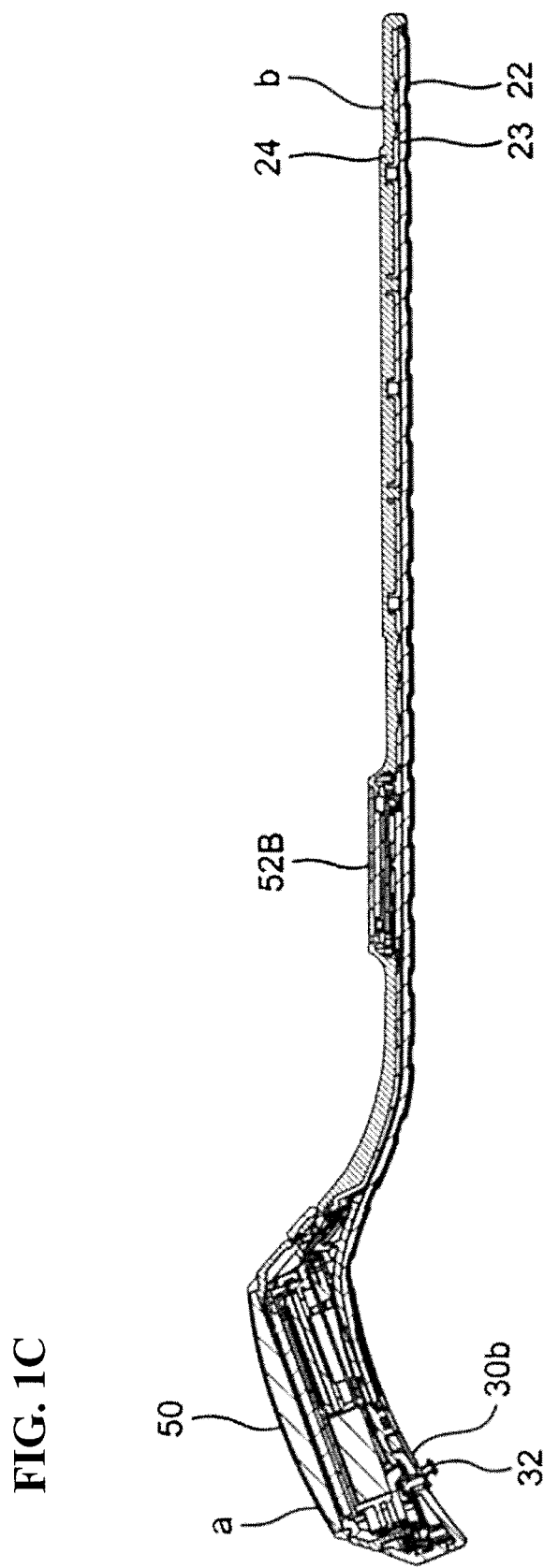

LASER LIGHT
→ X

→ X

BODILY INFORMATION MEASUREMENT APPARATUS

TECHNICAL FIELD

The present invention relates to a bodily information measurement apparatus, and more specifically relates to a bodily information measurement apparatus that is attached to a rod-shaped measurement site such as a wrist, for example.

BACKGROUND ART

In recent years, requirements of wrist-type blood pressure monitors have been increasing. For example, as disclosed in Patent Document 1 (JP 2010-51364A), a wrist-type blood pressure monitor 100 shown in FIG. 10 includes an apparatus main body 110 that has a main body case 21 with a housing shape and a display unit 26 provided on the front surface of the main body case 21, and a cuff 150 that is directly fixed to the apparatus main body 110. During blood pressure measurement, the user attaches the cuff 150 by wrapping it around his or her wrist.

CITATION LIST

Patent Literature

Patent Document 1: JP 2010-51364A
Patent Document 2: JP H6-11701A
Patent Document 3: JP S63-200144A
Patent Document 4: JP H9-285453A

SUMMARY OF INVENTION

However, with the above-described wrist-type blood pressure monitor 100, the apparatus main body 110 is large, and the cuff 150 for fixing the apparatus main body 110 to the wrist of the user is very thick. Accordingly, in order for the user to attach the wrist-type blood pressure monitor to his or her wrist, the user needs to wrap the thick cuff 150 around his or her arm while holding the large apparatus main body 110 with his or her hand, and thus it is very laborious and time-consuming to put on the wrist-type blood pressure monitor.

In view of this, advantageously, one or more embodiments of the present invention provide a bodily information measurement apparatus that is easy for a user to attach to his or her wrist.

Thus, a bodily information measurement apparatus according to one or more embodiments of the present invention is
 a bodily information measurement apparatus that is to be attached by being wrapped around a rod-shaped measurement site, the bodily information measurement apparatus including:
 a band-shaped belt that is to be wrapped around the measurement site;
 a main body that is arranged at a base end portion in a lengthwise direction of the belt and on which an element configured to measure bodily information is mounted; and
 a buckle for joining the base end portion and a leading end portion on an opposite side in the lengthwise direction of the belt such that the belt forms a loop shape,
 wherein the buckle includes, on an inner surface side of the base end portion of the belt, a first plate frame member that is attached at one end portion so as to be able to rotate about an axis that intersects the lengthwise direction of the belt, the first plate frame member extending in a plate shape from the one end portion to another end portion on the opposite side,
 on the other end portion of the first plate frame member, the buckle includes a second plate frame member that is attached at the one end portion so as to be able to rotate about an axis that is parallel to the axis, the second plate frame member extending in a plate shape from the one end portion to the other end portion on the side opposite thereto, and the other end portion of the second plate frame member is configured to be attachable to the leading end portion of the belt,
 the first plate frame member and the second plate frame member include a first opening portion and a second opening portion that penetrate through the respective members with respect to a plate surface, and
 in a state in which the inner surface of the main body, the first plate frame member of the buckle, and the second plate frame member of the buckle are folded so as to overlap, the first opening portion of the first plate frame member and the second opening portion of the second plate frame member are continuous in a thickness direction of the main body.

In the present specification, "base end portion", "leading end portion", "one end portion", and "other end portion" are not limited to the base end, the leading end, the one end, and the other end respectively, and may denote portions within certain ranges.

Also, "inner surface" denotes a surface on the measurement subject side in a state in which the bodily information measurement apparatus has been attached by being wrapped around the measurement site. "Outer surface" denotes a surface on the side opposite to that of the inner surface in a state in which the bodily information measurement apparatus has been attached by being wrapped around the measurement site.

Also, "bodily information" widely encompasses blood pressure values, a pulse value, an activity amount, a blood oxygen concentration, and the like.

With the bodily information measurement apparatus according to one or more embodiments of the present invention, the main body, on which an element for measuring the bodily information is mounted, is arranged at the base end portion in the lengthwise direction of the band-shaped belt that is to be wrapped around the measurement site, and the buckle for joining the base end portion and the leading end portion on the opposite side in the lengthwise direction of the belt such that the belt becomes loop-shaped is included. Furthermore, the buckle includes the second plate frame member that can be attached to the leading end portion of the belt and the first plate frame member that is joined to the second plate frame member and the main body.

When the user attaches the bodily information measurement apparatus to his or her wrist, the user passes his or her hand through the loop of the belt in a state in which the belt is loop-shaped and the main body, the first plate frame member, and the second plate frame member of the buckle are open toward each other, and then the user folds the main body, the first plate frame member, and the second plate frame member of the buckle in on each other. Accordingly, it is possible for the user to easily attach the bodily information measurement apparatus to his or her wrist.

Furthermore, in the folded state, the first opening portion of the first plate frame member and the second opening portion of the second plate frame member are continuous in the thickness direction of the main body, and therefore it is possible to achieve a configuration in which a fluid bladder for compressing the measurement site is arranged on the inner side of the main body. Accordingly, the measurement site located on the inner side of the main body is compressed.

With the bodily information measurement apparatus of an embodiment, a sticking mechanism that causes the inner surface side of the base end portion of the belt or the one end portion of the first plate frame member and the other end portion of the second plate frame member to stick together, or a lock mechanism that causes the inner surface side of the base end portion of the belt or the one end portion of the first plate frame member and the other end portion of the second plate frame member to engage with each other.

With the bodily information measurement apparatus according to one or more embodiments of the present invention, the inner surface side of the base end portion of the belt or the one end portion of the first plate frame member, and the other end portion of the second plate frame member are caused to stick to each other, and therefore when the main body, the first plate frame member, and the second plate frame member of the buckle are folded in on each other, the inner surface of the main body, the first plate frame member, and the second plate frame member of the buckle are guided so as to overlap.

Also, in addition to or instead of the sticking mechanism, it is preferable to include a lock mechanism that allows the inner surface side of the base end portion of the belt or the one end portion of the first plate frame member and the other end portion of the second plate frame member to engage with each other. Also, the sticking mechanism and/or the lock mechanism preferably include an unlocking mechanism for removing the sticking and/or the engagement.

With the bodily information measurement apparatus of an embodiment,
  the first opening portion opens toward the other end portion side of the first plate frame member, the second opening portion opens toward the one end portion side of the second plate frame member, and the first opening portion and the second opening portion are in communication, and
  a fluid bladder for compressing the measurement site during blood pressure measurement is provided in the belt in the lengthwise direction of the belt, and the fluid bladder is in communication with the inside of the main body through a region corresponding to the first opening portion and the second opening portion in the folded state.

In the present specification, the first opening portion "opening" toward the other end portion side of the first plate frame member and the second opening portion "opening" toward the one end portion side of the second plate frame member means that the first plate frame member and the second plate frame member that form the buckle do not actually exist, and for example, those members open in an approximate U shape.

With the bodily information measurement apparatus according to one or more embodiments of the present invention, the fluid bladder is in communication with the interior of the main body through the region corresponding to the first opening portion and the second opening portion in the folded state, and therefore the region of the measurement site that is spatially continuous from the portion corresponding to the inner side of the main body to the leading end portion of the belt can be compressed in the circumferential direction by the fluid bladder.

Accordingly, it is possible to further increase the area of contact between the fluid bladder and the measurement site, and therefore the efficiency of compressing the artery can be improved. Accordingly, the blood pressure measurement accuracy can be further increased.

With the bodily information measurement apparatus of an embodiment, the fluid bladder extends in the lengthwise direction to the leading end portion of the belt, and in the folded state, the portion of the main body with which the fluid bladder is in communication overlaps with the portion of the belt in which the fluid bladder is present.

With the bodily information measurement apparatus according to one or more embodiments of the present invention, the region of the belt that overlaps in the longitudinal direction swells by an amount corresponding to a thickness that is greater than the thickness of other regions. Accordingly, the distance by which the artery that exists at the measurement site moves away due to being pressed by the region other than the overlapping region decreases, and the extra pressure amount for pressing down the artery decreases. As a result, the measurement value of the blood pressure measured by inflating the fluid bladder can be brought closer to the true value, and the measurement accuracy can be increased.

With the bodily information measurement apparatus of an embodiment, a first fixing element is provided on the inner surface of the other end portion of the second plate frame member, and a second fixing element is provided on the outer surface of the leading end portion of the belt, and the first fixing element and the second fixing element are configured to be able to engage with each other.

With the bodily information measurement apparatus of this embodiment, the belt can be made into a loop shape, and the loop shape can be maintained.

With the bodily information measurement apparatus of an embodiment, a plate-shaped plate portion that can rotate about an axis that is parallel to the axis is formed on the other end portion of the second plate frame member,
  a first fixing element is provided on the inner surface of the plate portion, and a second fixing element is provided on the outer surface of the leading end portion of the belt, and
  the first fixing element and the second fixing element are configured to be able to engage with each other.

With the bodily information measurement apparatus of this embodiment, the belt can be made into a loop shape, and the loop shape can be maintained. Furthermore, since the first fixing element can rotate with respect to the belt, it is easier to engage the first fixing element with the second fixing element. Accordingly, the length of the loop of the belt is variable and is thus easier to set so as to exactly match the circumferential length of the wrist serving as the measurement site. Furthermore, since the first fixing element is formed on the plate portion, which can rotate with respect to the second plate frame member, the plate portion rotates even if a force is applied in the direction in which the first fixing element comes off during attachment to the wrist. Accordingly, since the force applied between the first fixing element and the second fixing element does not change, the first fixing element is not likely to come off of the second fixing element. Furthermore, since the first fixing element can rotate with respect to the belt, it is easier to engage the first fixing element with the second fixing element. Accordingly, the length of the loop of the belt is variable and is thus easier to set so as to exactly match the circumferential length of the wrist serving as the measurement site.

With the bodily information measurement apparatus of an embodiment, the first fixing element has one of a recessed shape and a protruding shape, and the second fixing element has the other of the recessed shape and the protruding shape.

With the bodily information measurement apparatus of this embodiment, the belt can easily be made into a loop shape, and the loop shape can be stably maintained.

With the bodily information measurement apparatus of an embodiment, the first fixing element is a screw, and the second fixing element is a recessed portion or a cavity portion that receives the screw.

With the bodily information measurement apparatus of this embodiment, the belt can easily be made into a loop shape, and the loop shape can be stably maintained.

With the bodily information measurement apparatus of an embodiment, the first fixing element is a latch mechanism, and the second fixing element is a protruding portion that extends in a width direction of the belt, and the latch mechanism includes latch arms that grip the protruding portion and a spring for adjusting an interval of the latch arms.

With the bodily information measurement apparatus of this embodiment, the belt can easily be made into a loop shape, and the loop shape can be stably maintained.

With the bodily information measurement apparatus of an embodiment, a plurality of said second fixing elements are formed in alignment in the lengthwise direction of the belt so as to enable adjustment of the attachment position of the other end portion of the second plate frame member in the lengthwise direction of the belt.

With the bodily information measurement apparatus of this embodiment, multiple said second fixing elements are formed in alignment in the lengthwise direction of the belt. Accordingly, it is possible to adjust the attachment position of the other end portion of the second plate frame member in the lengthwise direction of the belt. Accordingly, the length of the loop of the belt can be set variably so as to exactly match the circumferential length of the measurement site.

With the bodily information measurement apparatus of an embodiment, a plurality of said second fixing elements are formed in alignment in the width direction of the belt.

With the bodily information measurement apparatus of this embodiment, even if the belt is slightly twisted, the engagement between the first fixing element and the second fixing element is not likely to come undone.

With the bodily information measurement apparatus of an embodiment, at least the outer surface of the leading end portion of the belt is composed of a flexible material.

With the bodily information measurement apparatus of this embodiment, the engagement between the first fixing element and the second fixing element can be removed using the flexibility of the outer surface of the leading end portion of the belt.

With the bodily information measurement apparatus of an embodiment,
   at least one hook portion that is formed on the other end portion of the second plate frame member,
   wherein the leading end portion of the belt is formed so as to be wide in the width direction, which is perpendicular to the lengthwise direction of the belt, such that the leading end portion of the hook portion is caught and locked.

With the bodily information measurement apparatus of this embodiment, even if the belt twists slightly, the engagement between the first fixing element and the second fixing element is even less likely to come undone.

With the bodily information measurement apparatus of an embodiment,
   at least one hook-shaped hook portion that is formed on the other end portion of the second plate frame member is further included,
   wherein the leading end portion of the belt is formed so as to be thick, and a cut-out portion in which the leading end portion of the hook portion is inserted and locked is formed at the thick portion.

With the bodily information measurement apparatus of this embodiment, even if the belt twists slightly, the engagement between the first fixing element and the second fixing element is even less likely to come undone.

With the bodily information measurement apparatus of an embodiment,
   a third fixing element is provided on a side surface of the hook portion, and a fourth fixing element is provided on a side surface of the leading end portion of the belt, and
   the third fixing element and the fourth fixing element are configured to be able to engage with each other.

With the bodily information measurement apparatus of this embodiment, even if the belt twists slightly, the engagement between the first fixing element and the second fixing element is even less likely to come undone.

With the bodily information measurement apparatus of an embodiment,
   the third fixing element is a screw, and the fourth fixing element is a recessed portion or a cavity portion that receives the screw.

With the bodily information measurement apparatus of this embodiment, the belt can easily be made into a loop, and the loop shape can be stably maintained.

With the bodily information measurement apparatus of an embodiment, on the other end portion of the second plate frame member, a plate-shaped member that can rotate about an axis that is parallel to the axis is further included.

With the bodily information measurement apparatus of this embodiment, even if the belt twists slightly, the engagement between the first fixing element and the second fixing element is even less likely to come undone.

As is evident from the description above, in the bodily information measurement apparatus according to one or more embodiments of the present invention, the buckle provided on the inner side of the main body is used to join the base end portion of the belt and the leading end portion on the opposite side, whereby the main body can be attached by being wrapped around the measurement site, and therefore the user can easily attach the bodily information measurement apparatus to his or her wrist.

BRIEF DESCRIPTION OF DRAWINGS

FIG. 1C is a lateral cross-sectional view of the bodily information measurement apparatus 1 taken along line A-A in FIG. 1A.

DESCRIPTION OF EMBODIMENTS

Figure 1A:
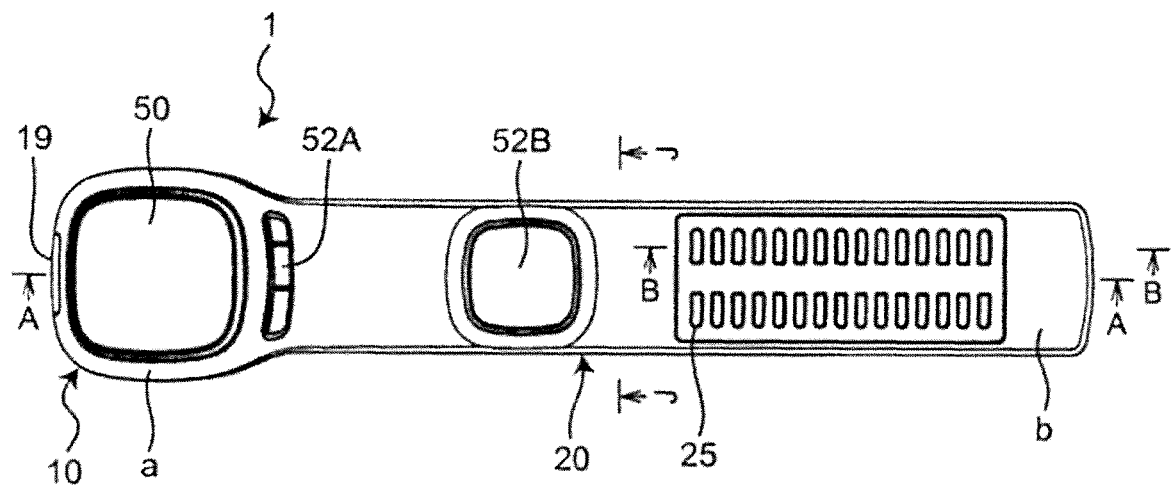
FIG. 1A is a top view showing an exterior of a bodily information measurement apparatus 1 according to a first embodiment of the present invention.

Hereinafter, embodiments according to the present invention will be described with reference to the drawings. Note that in the following embodiments, similar constituent elements are denoted by the same reference numerals and redundant description thereof is not included.

First Embodiment

Figure 1B:
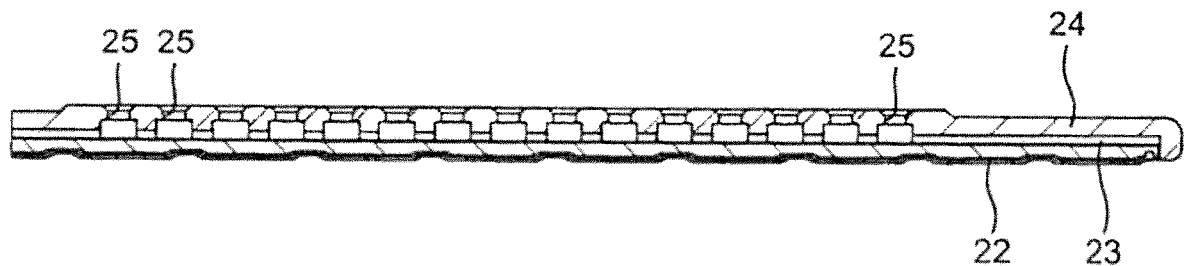
FIG. 1B is a lateral cross-sectional view of the bodily information measurement apparatus 1 taken along line B-B in FIG. 1A.
Figure 2:
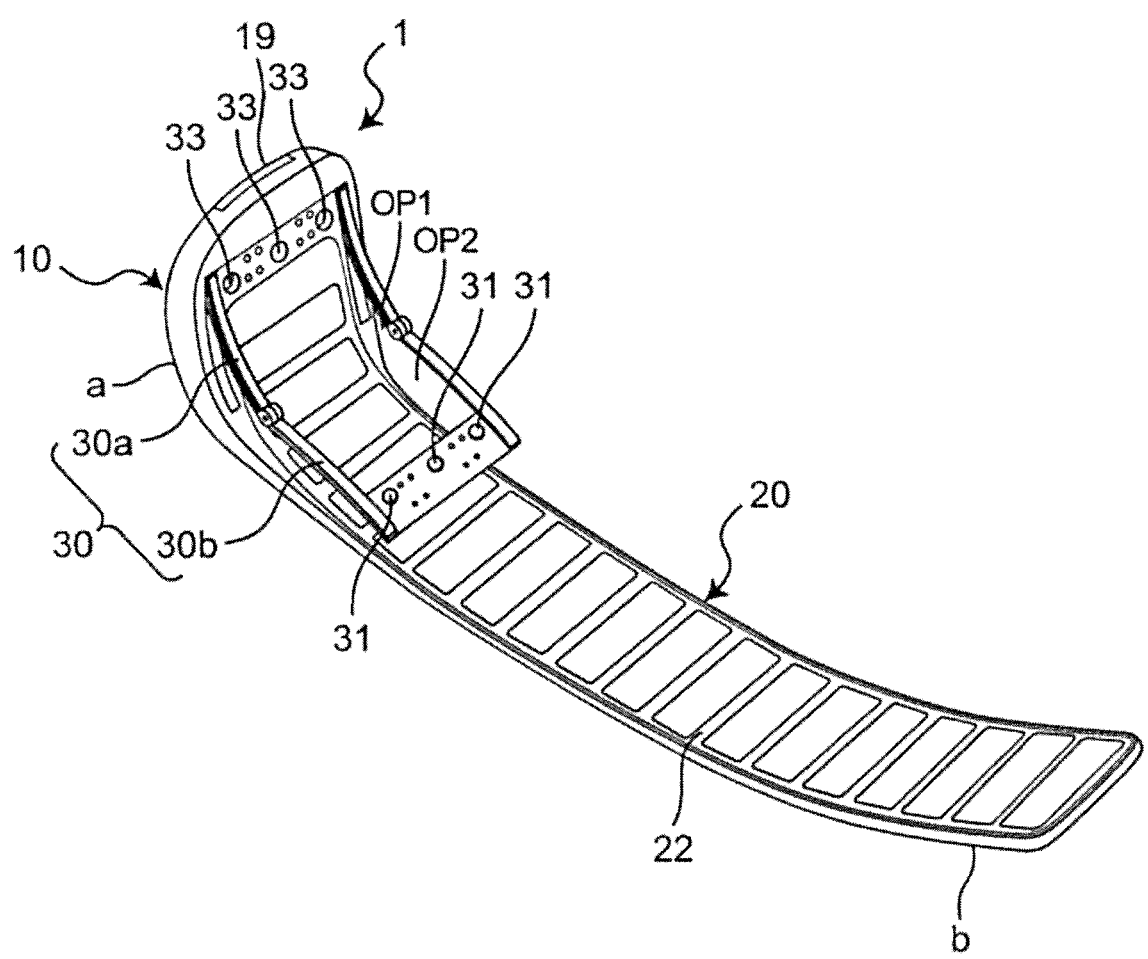
FIG. 2 is a bottom view of the bodily information measurement apparatus 1 shown in FIG. 1.
Figure 4:
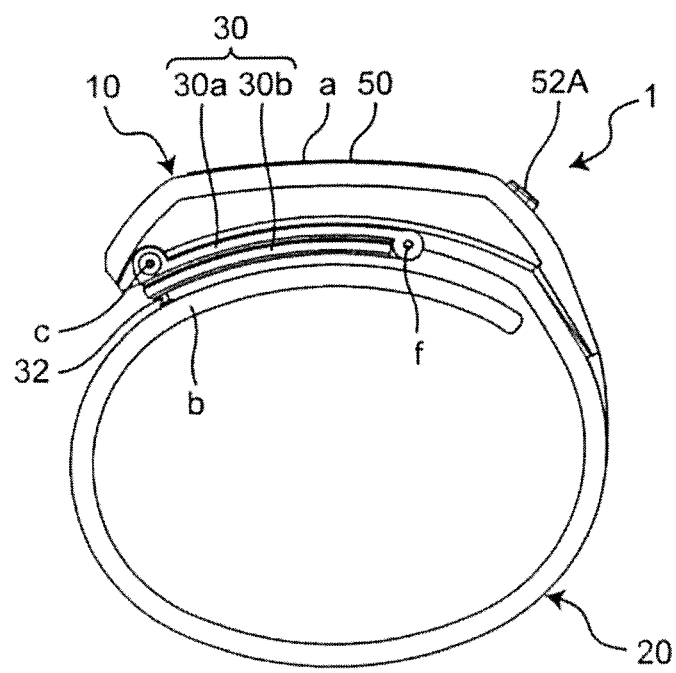
FIG. 4 is a diagram showing a view of the bodily information measurement apparatus 1 in FIG. 3 in a direction orthogonal to the loop of the belt.
Figure 5:
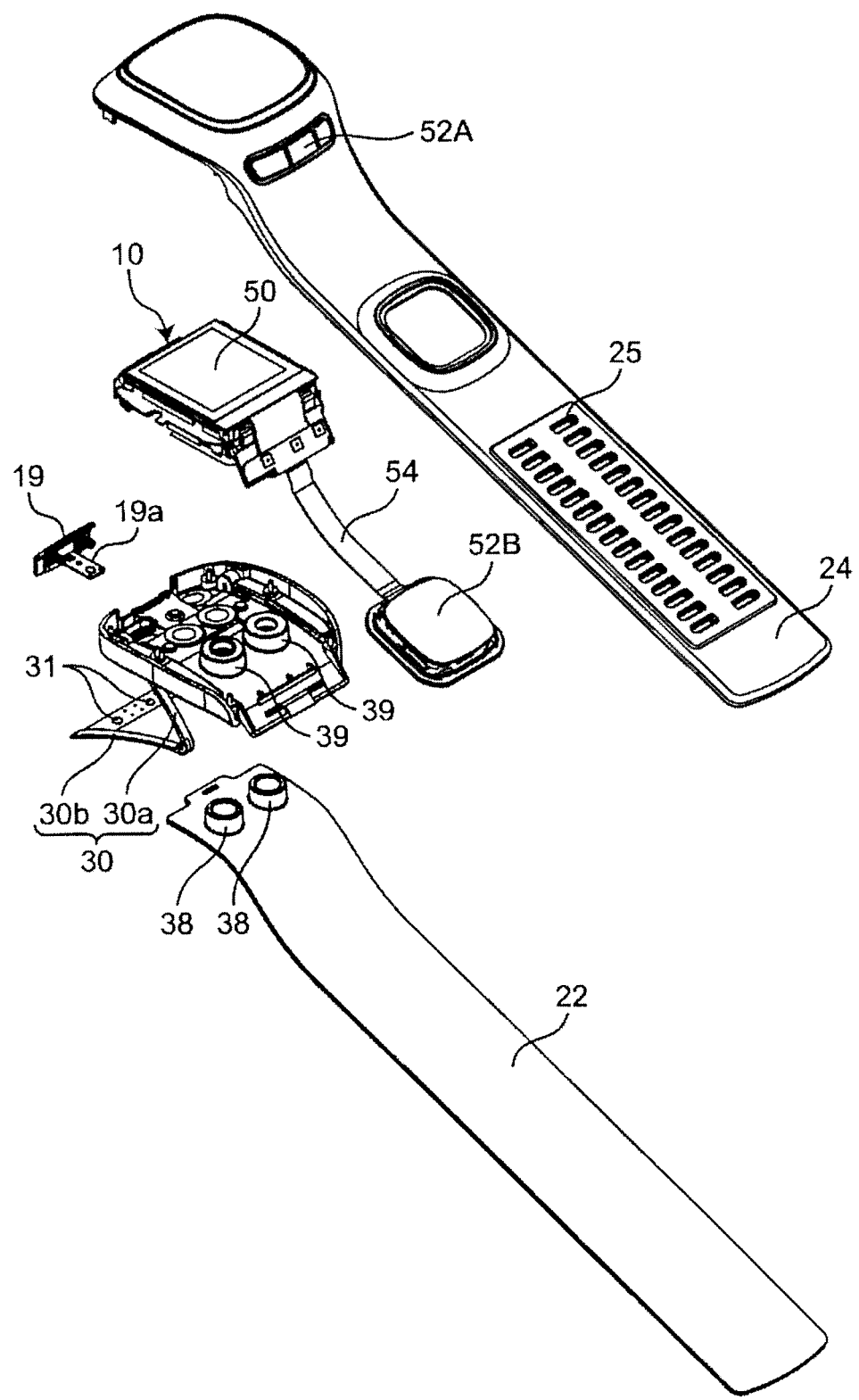
FIG. 5 is an exploded perspective view for illustrating a structure of the bodily information measurement apparatus 1 in FIG. 1A.

FIG. 1A is a top view showing an exterior of a bodily information measurement apparatus 1 according to a first embodiment of the present invention, FIG. 1B is a lateral cross-sectional view of the bodily information measurement apparatus 1 taken along line B-B in FIG. 1A, and FIG. 1C is a lateral cross-sectional view of the bodily information measurement apparatus 1 taken along line A-A in FIG. 1A. Also, FIG. 2 is a bottom view of the bodily information measurement apparatus 1 shown in FIG. 1, FIG. 3 is a perspective view showing a state at a time of attaching the bodily information measurement apparatus shown in FIG. 1 by wrapping it around the measurement site, FIG. 4 is a diagram showing a view of the bodily information measurement apparatus 1 shown in FIG. 3 in a direction orthogonal to the loop of the belt 20, and FIG. 5 is an exploded perspective view for illustrating a structure of the bodily information measurement apparatus 1 shown in FIG. 1A.

Figure 3:
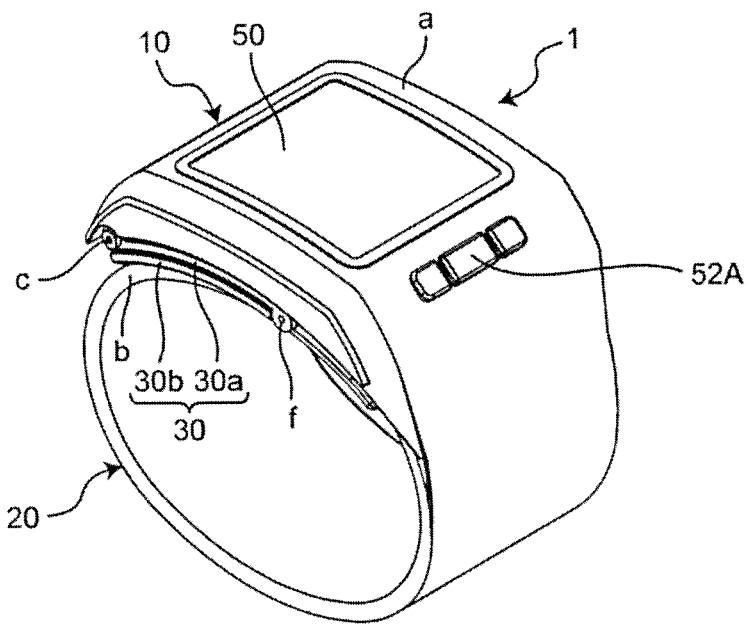
FIG. 3 is a perspective view showing a state at a time when the bodily information measurement apparatus 1 shown in FIG. 1 is formed into a loop shape.

As can be understood from FIG. 3, the bodily information measurement apparatus 1 is attached by being wrapped around a rod-shaped measurement site, such as a wrist 90 (see FIGS. 7A to 7C) of a user, for example, and includes a band-shaped belt 20 that is to be wrapped around the measurement site, a main body 10 that is arranged at a base end portion a in the lengthwise direction of the belt 20 and on which an element for measuring blood pressure is mounted, and a buckle 30 for joining the base end portion a and a leading end portion b on the side opposite thereto in the lengthwise direction of the belt 20 such that the belt 20 becomes a loop shape. Here, the belt 20 serves as a blood pressure measurement cuff. Hereinafter, the structure of the belt 20 will be described.

As can be understood from FIG. 1B, the belt 20 includes a fluid bladder 22 for compressing the measurement site during blood pressure measurement, a reinforcing layer 23 that is provided along the outer surface of the fluid bladder 22 and is for suppressing outward swelling of the fluid bladder 22, and an outer circumferential layer 24 that is provided along the outer surface of the reinforcing layer 23 and covers the reinforcing layer 23. Accordingly, since outward swelling of the fluid bladder 22 can be suppressed, the efficiency of compressing the measurement site can be improved, and the blood pressure measurement accuracy can be further increased. On the other hand, the surface of the fluid bladder 22 (becomes the inner surface when worn) has multiple recesses and protrusions along the lengthwise direction and can easily swell toward the measurement site.

Also, the fluid bladder 22, the reinforcing layer 23, and the outer circumferential layer 24 that are included in the belt 20 are each formed of an elastomer material. For this reason, the belt 20 is flexible, and therefore can be wrapped around the wrist 90, is not likely to get dirty, and can be wiped with a damp cloth.

Furthermore, the hardness of the reinforcing layer 23 is greater than the hardness of the outer circumferential layer 24, which is greater than the hardness of the fluid bladder 22. Accordingly, since the reinforcing layer 23 can suppress outward swelling of the fluid bladder 22 when the fluid bladder 22 swells, the efficiency of compressing the measurement site can be improved. Accordingly, the blood pressure measurement accuracy can be further increased. Furthermore, since the outer circumferential layer 23, which has a hardness that is smaller than the hardness of the reinforcing layer 23, covers the outer circumference of the reinforcing layer 23, the outer circumferential layer 24 of the belt 20 is soft to the touch.

Figure 23A:
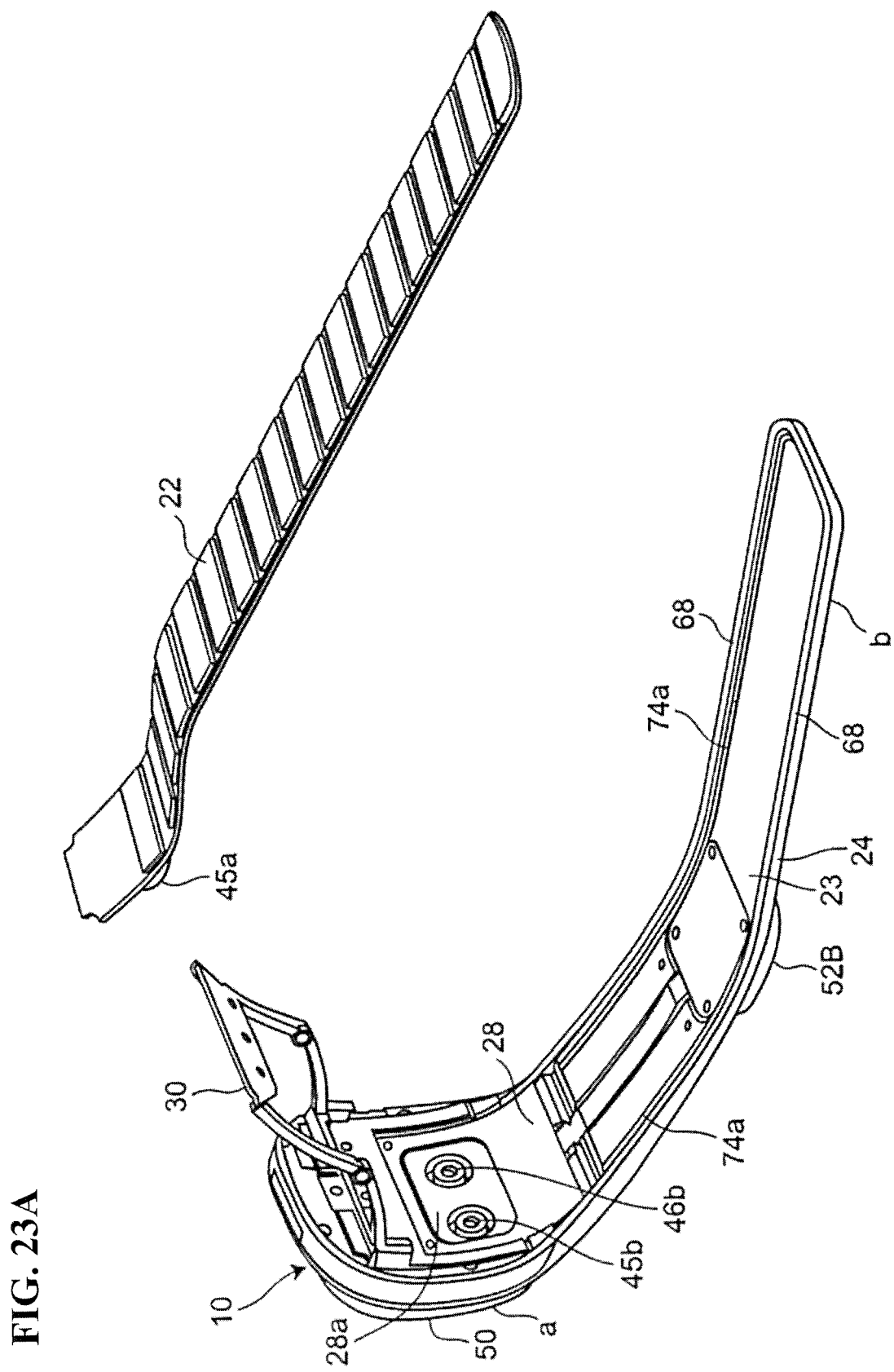
FIG. 23A is an exploded perspective view for illustrating a structure of the belt 20 of the bodily information measurement apparatus 1 in FIG. 1A.
Figure 23B:
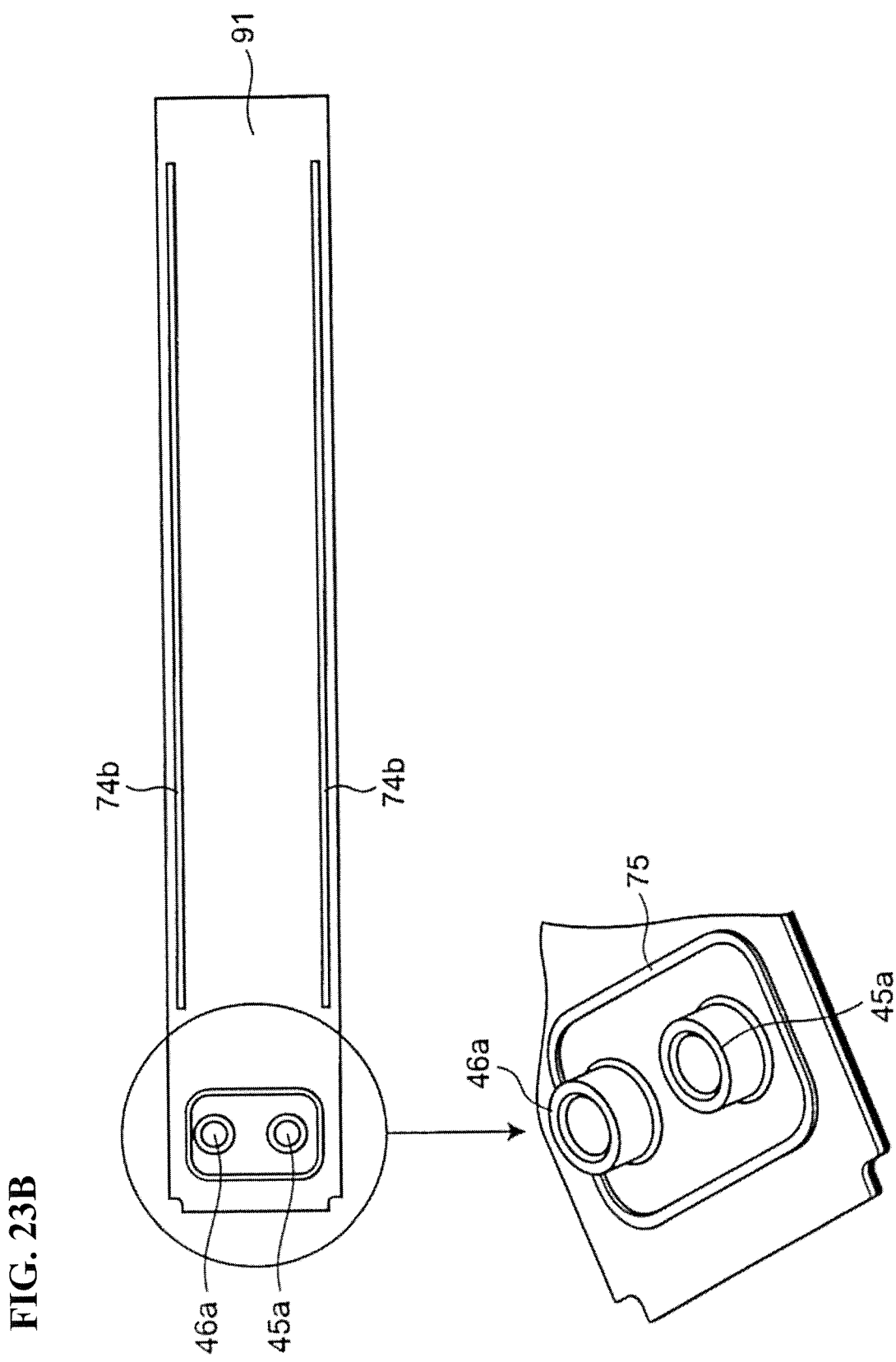
FIG. 23B is a plan view showing an adhesion surface of a fluid bladder 22 in FIG. 23A.
Figure 23C:
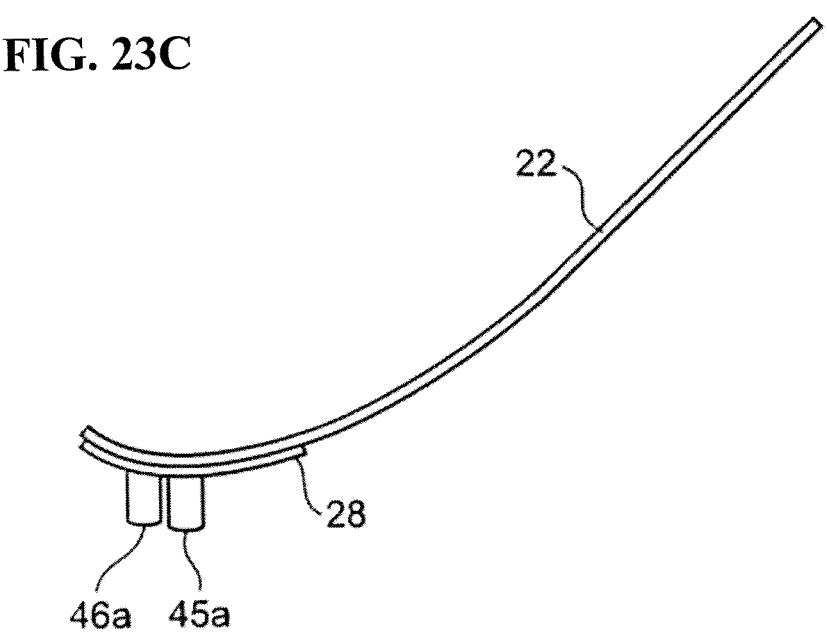
FIG. 23C is a side view schematically showing a state at a time when a reinforcing plate 28 is adhered to the fluid bladder 22 in FIG. 23A.
Figure 23D:
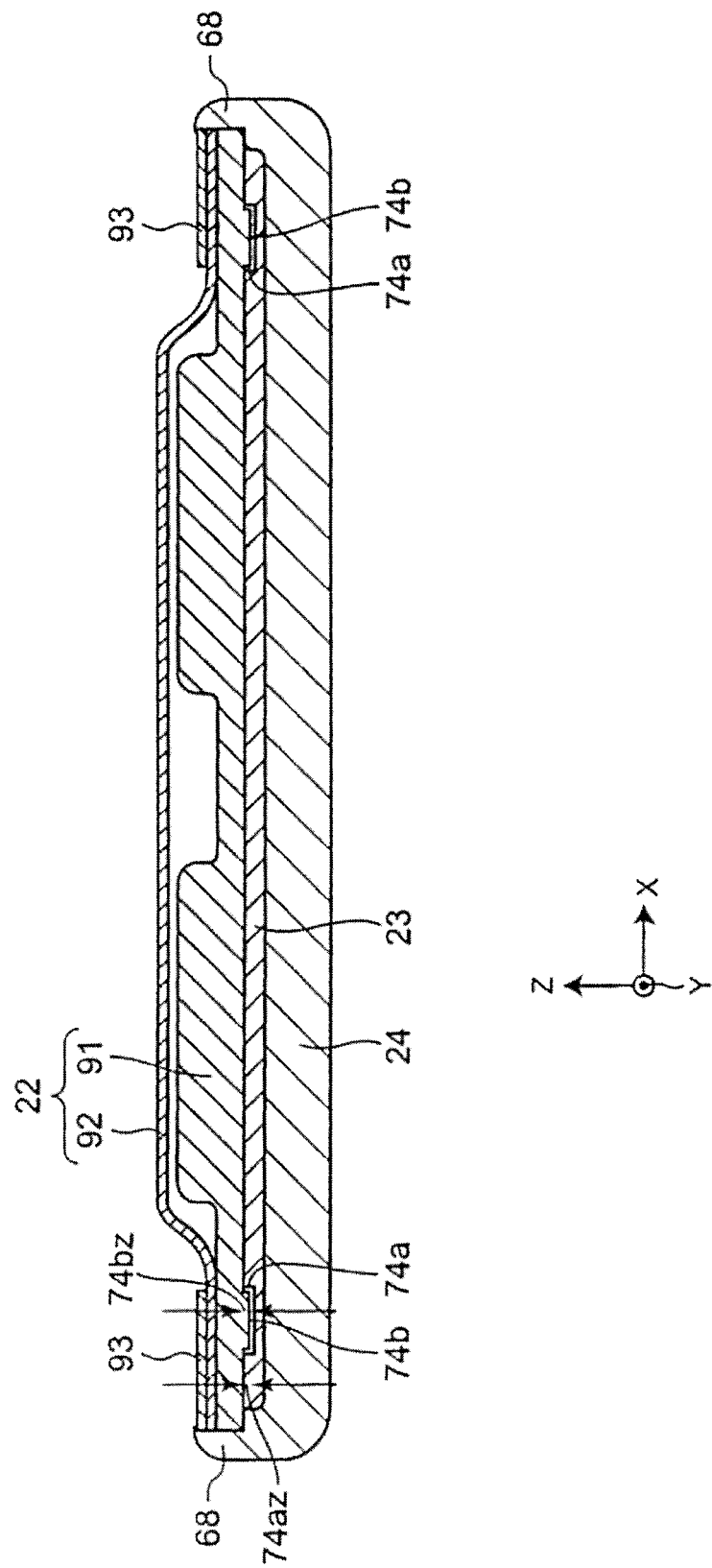
FIG. 23D is a lateral cross-sectional view of the bodily information measurement apparatus 1 taken along line J-J in FIG. 1A.

FIG. 23A is an exploded perspective view for illustrating the structure of the belt 20 of the bodily information measurement apparatus 1 shown in FIG. 1A. Here, a bottom surface of the bodily information measurement apparatus 1 is shown. FIG. 23B is a plan view showing an adhesion surface of the fluid bladder 22 shown in FIG. 23A. FIG. 23C is a side view schematically showing a state at a time when a reinforcing plate 28 is adhered to the fluid bladder 22 shown in FIG. 23A. FIG. 23D is a lateral cross-sectional view of the bodily information measurement apparatus 1 taken along line J-J in FIG. 1A. In FIG. 23D, the width direction of the belt 20 is shown as the X direction, the lengthwise direction is shown as the Y direction, and the thickness direction is shown as the Z direction.

Figure 24A:
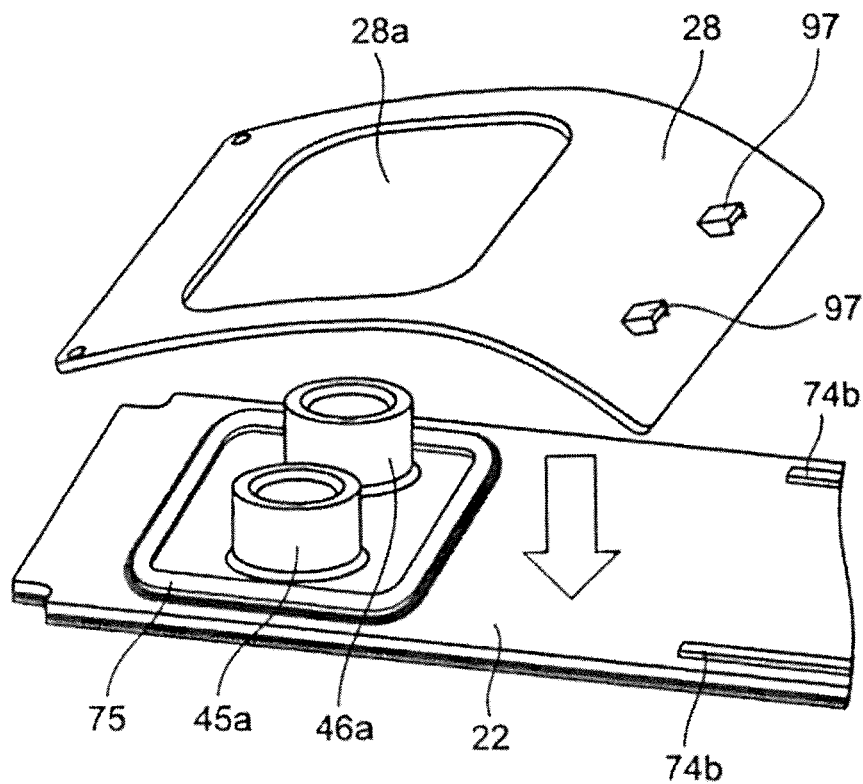
FIG. 24A is a schematic diagram showing a first step of assembling the belt 20 in FIG. 1A.
Figure 24B:
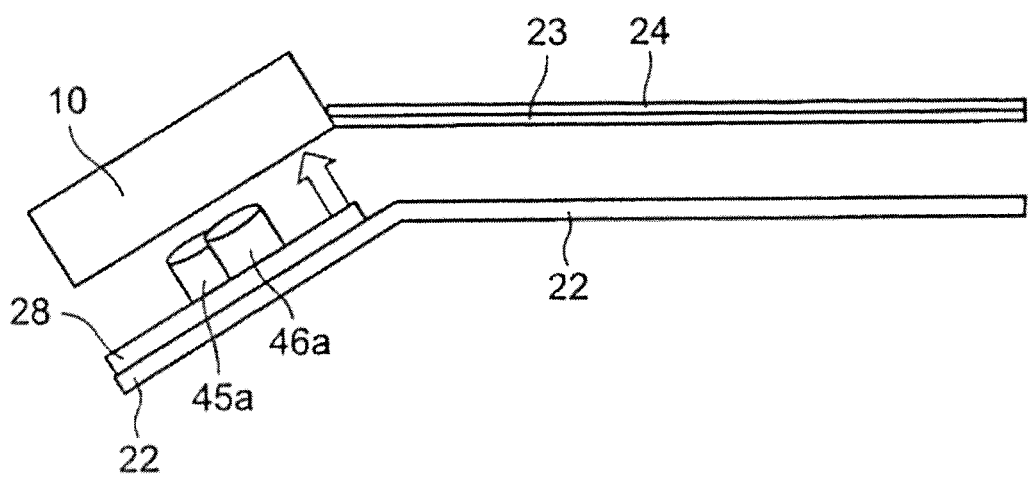
FIG. 24B is a schematic diagram showing a second step of assembling the belt 20 in FIG. 1A.
Figure 24C:
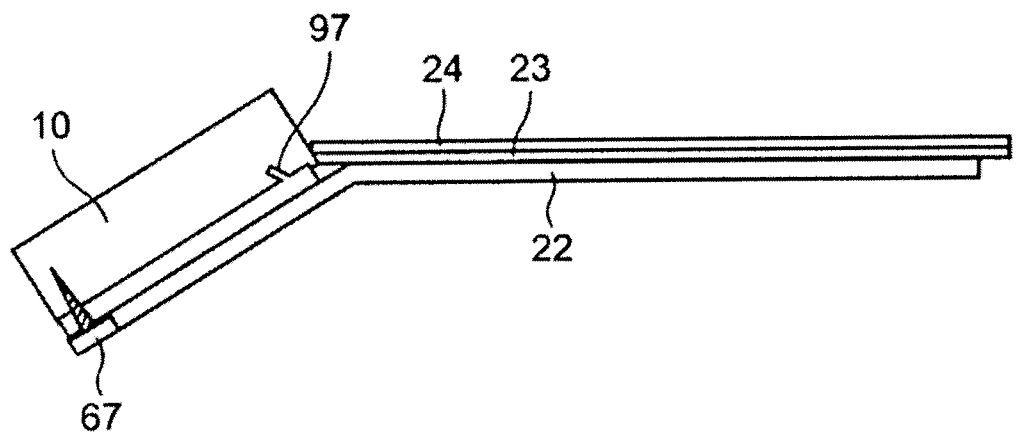
FIG. 24C is a schematic diagram showing a third step of assembling the belt 20 in FIG. 1A.

As shown in FIG. 23A, the main body 10 and the fluid bladder 22 are bonded by fitting the reinforcing plate 28 adhered to the fluid bladder 22 side in the main body 10 and fastening with a screw 67 (see FIG. 24C). The reinforcing plate 28 is adhered to the base end portion a side of the fluid bladder 22 using adhesive. Accordingly, by removing the screw 67, the fluid bladder 22 and the reinforcing plate 28 are removed from the main body 10. However, FIG. 23A shows a state when only the fluid bladder 22 has been removed so that the position of the reinforcing plate 28 at the time when the fluid bladder 22 is bonded to the main body 10 using the screw 67 is clearer.

A ventilation port 45b serving as a first main body-side pipe element for supplying a fluid for inflation from a piezoelectric pump 17 (see FIG. 8) mounted in the main body 10 to the interior of the fluid bladder 22, and a ventilation port 46b serving as a second main body-side pipe element for transferring the pressure in the fluid bladder 22 to the pressure sensor 16 (see FIG. 8) mounted on the main body 10 using the fluid are provided on a surface of the main body 10 that opposes the fluid bladder 22. The fluid bladder 22 includes a nipple 45a serving as a first bladder-side pipe element that fits air-tightly in the ventilation port 45b in a state of opposing the main body 10, and a nipple 46a serving as a second bladder-side pipe element that fits air-tightly in the ventilation port 46b. Here, the portion of the fluid bladder 22 that opposes the main body 10 is removably attached to the main body 10 via the reinforcing plate 28 adhered to that portion. With this configuration, the reinforcing plate 28 is bonded to the main body 10 via the screw 67, and therefore the fluid bladder 22 is more strongly attached to the main body 10. Furthermore, by removing the screw 67, the fluid bladder 22 and the reinforcing plate 28 can be easily removed, and therefore the ventilation port of the pressure sensor 16 and the piezoelectric pump 17 can be exposed. Accordingly, it is possible to perform product testing simply using the ventilation ports 45a and 45b by merely removing the screw 67.

Also, a through hole 28a having a shape through which all of the ventilation ports 45b and 46b and the nipples 45a and 46a pass is formed in the reinforcing plate 28. With this configuration, it is easier to fit the nipple 45a and the ventilation port 45b together and to fit the nipple 46a and the ventilation port 46b together.

As shown in FIG. 23B, a protruding ring 75 that protrudes in the thickness direction of the belt 20 is provided at a position along the inner side with respect to the edge portion of the through hole 28a of the reinforcing plate 28 that is to be attached, on the surface of the fluid bladder 22 that opposes the main body 10. With this configuration, the adhesive that is applied between the reinforcing plate 28 and the fluid bladder 22 does not protrude inward with respect to the protruding ring 75.

The portion of the fluid bladder 22 to which the reinforcing plate 28 is not adhered is adhered to the reinforcing layer 23 of the belt 20 with adhesive. As shown in FIGS. 23A and 23D, on the inner circumferential surface of the belt 20, the two edge portions 68 in the width direction (X direction) of the belt 20 protrude in the thickness direction (Z direction) and extend linearly in the lengthwise direction (Y direction). The gap between the two edge portions 68 is narrower than the width of the fluid bladder 22, and the fluid bladder 22 is pressed in the width direction (X direction) of the belt 20 between the two edge portions 68 so as to be adhered to the belt 20. With this configuration, the gap between the two edge portions 68 and the fluid bladder 22 is eliminated in the width direction of the belt 20. For this reason, dust is less likely to accumulate and the appearance improves.

As shown in FIG. 23A, grooves 74a with recessed cross sections extend linearly in the lengthwise direction (Y direction) on the surface of the reinforcing layer 23. The adhesive for adhering the fluid bladder 22 to the reinforcing layer 23 is applied to the grooves 74a. As shown in FIGS. 23B and 23D, protruding lines 74b that fit in the grooves 74a are provided on a base layer 91 of the fluid bladder 22 that opposes the reinforcing layer 23. Due to this configuration, the adhesion step becomes easier, while protrusion of the adhesive is suppressed.

As shown in FIG. 23D, the side surfaces and the bottom surfaces of the protruding lines 74b are adhered to the grooves 74a. Due to this configuration, it is possible to increase the strength of adhesion in the width direction (X direction) and the thickness direction (Z direction) of the belt 20. Note that in the present embodiment, the depth dimension 74aZ of the linear grooves 74a is greater than the height dimension 74bZ of the protruding lines 74b, but the present invention is not limited to this. For example, the depth dimension 74aZ of the linear grooves 74a and the height dimension 74bZ of the protruding lines 74b may be made equal. Due to this configuration, it is possible to further increase the strength of adhesion in the width direction (X direction) and the thickness direction (Z direction) of the belt 20.

As shown in FIG. 23D, the fluid bladder 22 includes a base layer 91 that opposes the inner circumferential surface of the belt 20 and a top layer 92 that is arranged so as to overlap with the base layer 91, the edge portions of the base layer 91 and the top layer 92 are welded, and thus a bladder shape is formed. Here, the base layer 91 is less likely to stretch than the top layer 92. Due to this configuration, the base layer 91 is not likely to come off of the inner circumferential surface of the belt 20 when the fluid bladder 22 swells. Note that sheets 93 for preventing lateral bulging of the fluid bladder 22 are further welded in the thickness direction on the edge portions at which the top layer 92 and the base layer 91 are welded. With this configuration, lateral bulging is suppressed when the fluid bladder 22 swells.

Figure 24D:
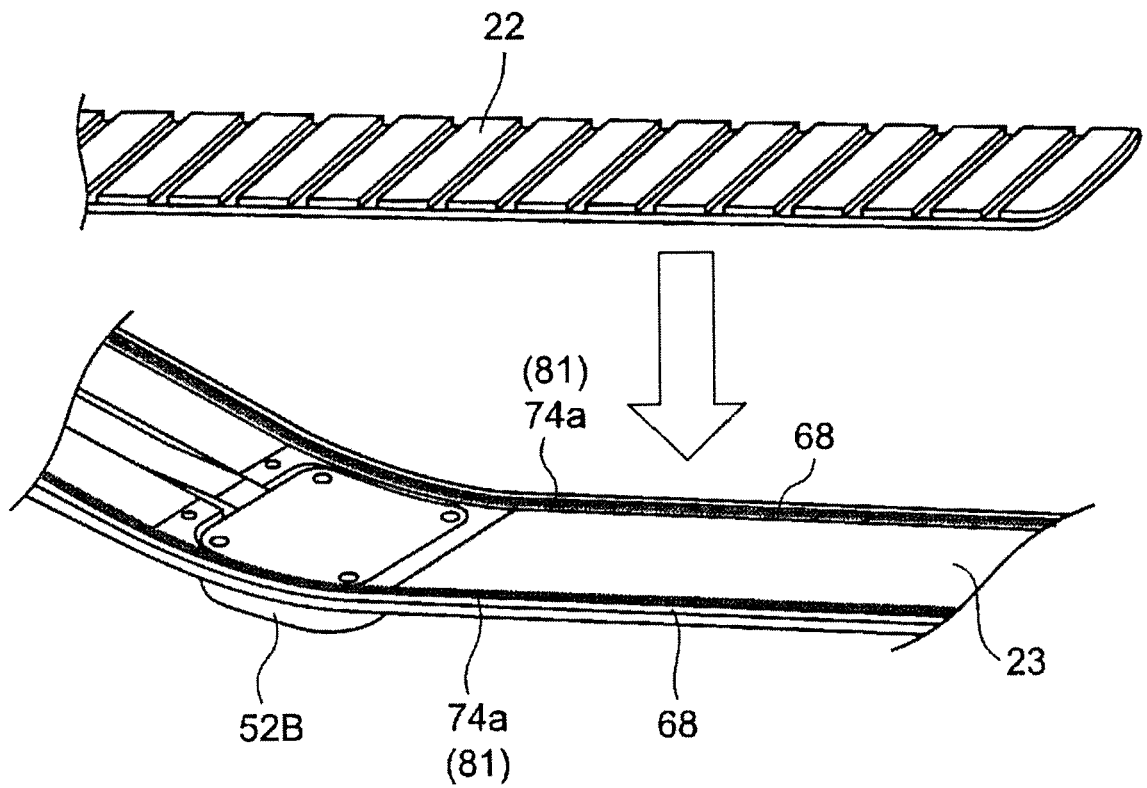
FIG. 24D is a schematic diagram showing a fourth step of assembling the belt 20 in FIG. 1A.
Figure 24E:
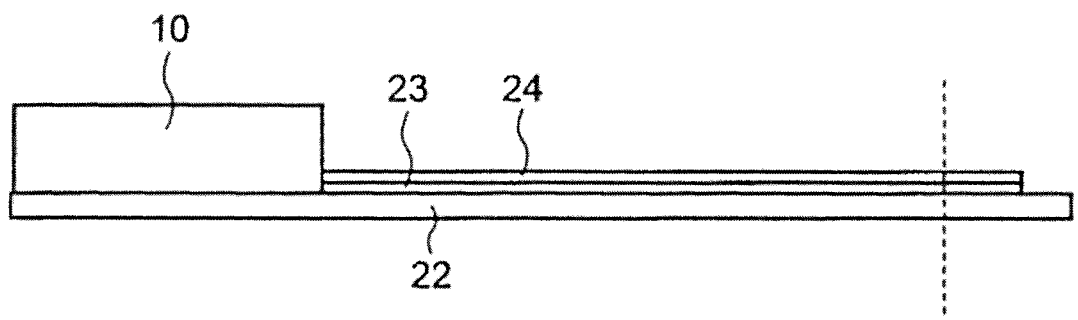
FIG. 24E is a schematic diagram showing a fifth step of assembling the belt 20 in FIG. 1A.
Figure 24F:
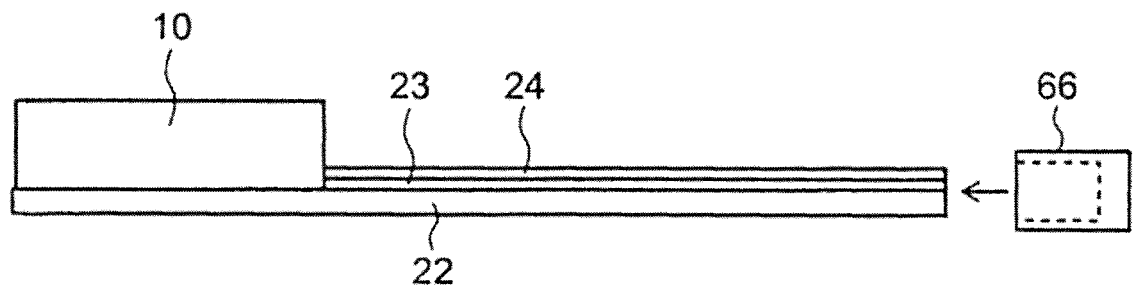
FIG. 24F is a schematic diagram showing a sixth step of assembling the belt 20 in FIG. 1A.

FIGS. 24A to 24F are schematic diagrams showing steps for assembling the belt 20 shown in FIG. 1A. First, as shown in FIG. 24A, the reinforcing plate 28 is adhered to the fluid bladder 22. Next, as shown in FIG. 24B, the nipples 45a and 46a are inserted into the ventilation ports 45b and 46b of the main body 10, and claws 97 of the reinforcing plate 28 are fit into a fit-together portion (not shown) provided on the main body 10 side and fastening is performed with the screw 67 (see FIG. 24C). Next, as shown in FIG. 24D, the reinforcing layer 23 and the fluid bladder 22 are adhered. At this time, the adhesive 81 is allowed to flow into the grooves 74a located several millimeters inward from the two edge portions 68 of the belt 20, and thereafter the fluid bladder 22 is adhered by being bonded. Next, as shown in FIG. 24E, the leading ends of the fluid bladder 22, the reinforcing layer 23, and the outer circumferential layer 24 are cut at the location of the dotted line. Finally, as shown in FIG. 24F, a cap member 66 is bonded to the cut end portion with the adhesive, and the leading ends are collectively covered.

Figure 24G:
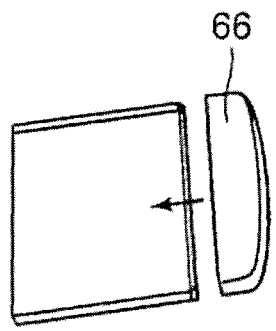
FIG. 24G is a schematic diagram showing a seventh step of assembling the belt 20 in FIG. 1A.

Furthermore, thereafter, as shown in FIG. 24E, the leading ends of the fluid bladder 22, the reinforcing layer 23, and the outer circumferential layer 24 may be further cut at the location of the dotted line, and then, as shown in FIGS. 24F and 24G the cap member 66 may be bonded with adhesive at the cut end portions, and the leading end portions may be collectively covered. The cap member 66 is a member that is formed of an elastomer material in which a depression that envelops the leading end portion of the belt 20 is provided. By placing the cap member 66 on the leading end portion of the belt 20, it is possible to conceal positional misalignment that occurs due to dimensional error and the like of the components, between the leading end portion of the reinforcing layer 23 of the belt 20, the leading end portion of the outer circumferential layer 24 of the belt 20, and the leading end portion of the fluid bladder 22 of the belt 20. Accordingly, the appearance of the product improves.

Note that by giving the leading end portion of the belt 20 a rounded shape so as to curve toward the inner circumferential surface and making it easier to slide by forming the cap member 66 with a material having a low friction coefficient, adding a mechanism such as a roller, or the like, it is possible to increase the wearability of the belt 20.

FIG. 25 is a lateral cross-sectional view illustrating a step of a method for manufacturing the fluid bladder 22. The fluid bladder 22 is manufactured using laser transmission welding (LTW). The fluid bladder 22 is formed into a bladder shape overall by overlapping two layers (the base layer 91 and the top layer 92). The sheets 93 for preventing lateral bulging are furthermore overlaid on the edge portions of the fluid bladder 22. Here, one edge portion in the width direction (X direction) will be described. The other edge portion is welded using a similar method as well.

Figure 25A:
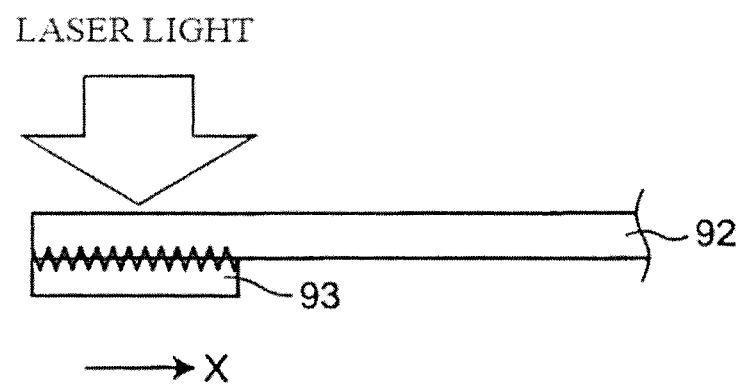
FIG. 25A is a lateral cross-sectional view illustrating a first step of a method for manufacturing the fluid bladder 22 in FIG. 23D.

First, as shown in FIG. 25A, the top layer 92 composed of a light-absorbing material is prepared, and the sheet 93 for preventing lateral bulging, which is composed of a light-absorbing material, is laid on the edge portion on the outer surface of the top layer 92. Next, for example, laser light is emitted from the top layer 92 side over the entire region of the sheet 93 in the width direction (X direction). Upon doing so, the light-absorbing material melts and is welded as overlapping portions, and the sheet 93 is welded. In FIG. 25A (and later-described FIGS. 25B, 26A, and 26B), the welded region is indicated by a triangular wave mark.

Figure 25B:
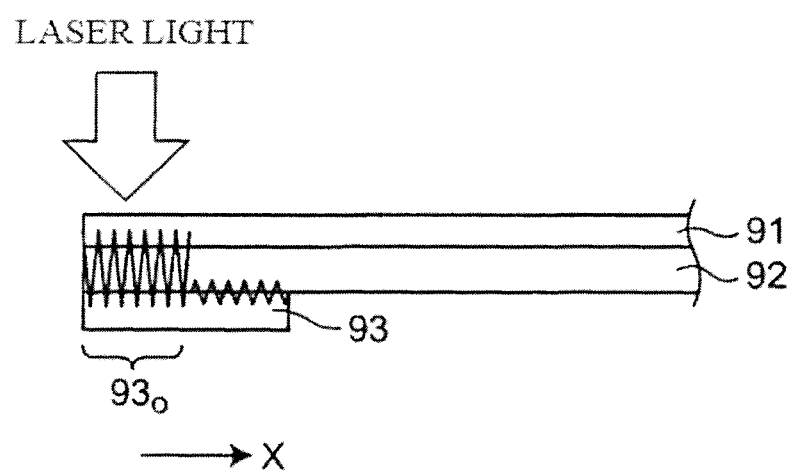
FIG. 25B is a lateral cross-sectional view illustrating a second step of a method for manufacturing the fluid bladder 22 in FIG. 23D.

Next, as shown in FIG. 25B, the base layer 91 composed of a light-transmitting material is laid on the inner surface of the top layer 92. Then, the laser light is once again emitted from the base layer 91 side to only the outside region 93o of the sheet 93 in the width direction (X direction). Upon doing so, the base layer 91 and the top layer 92 are welded at the emission region (outside region 93o). Accordingly, the base layer 91 and the top layer 92 are welded and the fluid bladder 22 is formed. Here, the portions of the base layer 91 and the top layer 92 that oppose the sheets 93 for preventing lateral bulging are not welded. With this configuration, it is possible to effectively use the width of the fluid bladder while preventing lateral bulging.

Here, a modified example of a method for manufacturing the fluid bladder 22 will be described. With the method for manufacturing the fluid bladder 22, laser light is emitted twice to the same region (the outside region 93o of the sheet 93). In this case, since laser emission is performed multiple times on the same region, there is a possibility that the material will deteriorate. In contrast to this, in the present modified example, the problem related to deterioration of the material is prevented from occurring by setting the number of emissions of laser light on the same region to one.

FIG. 26 shows lateral cross-sectional views illustrating a modified example of a step of a method for manufacturing the fluid bladder 22 according to a modified example of the first embodiment. Similarly to the example shown in FIG. 25, the fluid bladder 22 is formed into a bladder shape overall by overlapping two layers (the base layers 91 and the top layer 92). The sheet 93 for preventing lateral bulging is furthermore overlaid on the edge portion of the fluid bladder 22. Here, one edge portion in the width direction (X direction) has been described. The other edge portion is welded using a similar method as well.

Figure 26A:
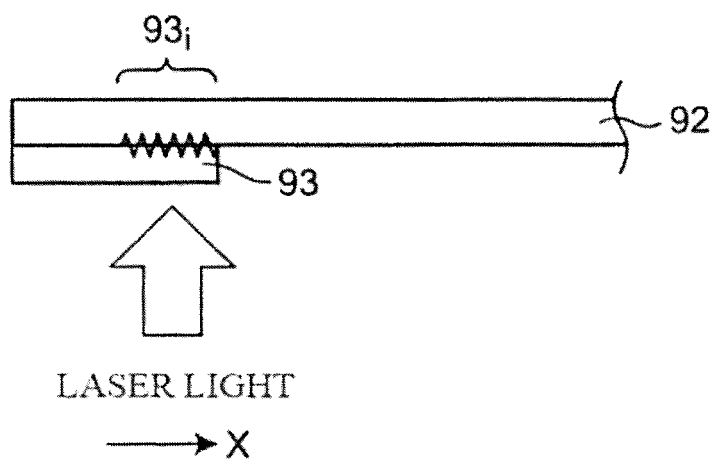
FIG. 26A is a lateral cross-sectional view illustrating a modified example of a first step of a method for manufacturing the fluid bladder 22 in FIG. 23D according to a modified example of the first embodiment.

First, as shown in FIG. 26A, the top layer 92 composed of a light-absorbing material is prepared, and the sheet 93 for preventing lateral bulging, which is composed of a light-absorbing material, is laid on the edge portion on the outer surface of the top layer 92. Next, laser light is emitted from the sheet 93 side to only the inside region 93i of the sheet 93 in the width direction (X direction). Upon doing so, the light absorbing material melts and the sheet 93 is welded at the inside region 93i.

Figure 26B:
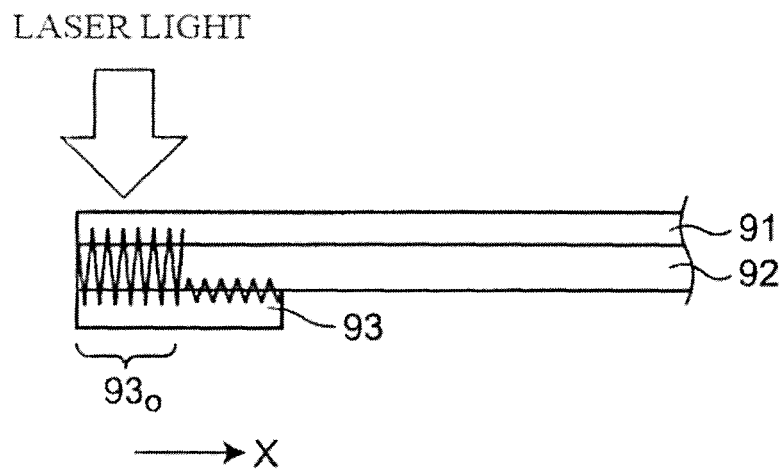
FIG. 26B is a lateral cross-sectional view illustrating a modified example of a second step of a method for manufacturing the fluid bladder 22 in FIG. 23D according to a modified example of the first embodiment.

Next, as shown in FIG. 26B, the base layer 91 composed of a light-transmitting material is laid on the inner surface of the top layer 92. Then, the laser light is once again emitted from the base layer 91 side to only the outside region 93o of the sheet 93 in the width direction (X direction). Upon doing so, the base layer 91 and the top layer 92 are welded at the emission region (outside region 93o). Accordingly, the base layer 91 and the top layer 92 are welded and the fluid bladder 22 is formed. Here, laser light can be partially transmitted by making the top layer 92 thinner. Here, the portions of the base layer 91 and the top layer 92 that oppose the sheets 93 for preventing lateral bulging are not welded. With this configuration, it is possible to effectively use the width of the fluid bladder while preventing lateral bulging.

The above-described belt 20 is manufactured as follows.

Figure 11A:
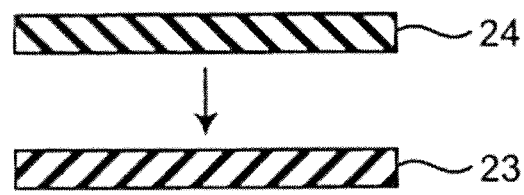
FIGS. 11A, 11B, and 11C show lateral cross-sectional views illustrating a step of a method for manufacturing a belt 20 in FIG. 1.
Figure 11B:
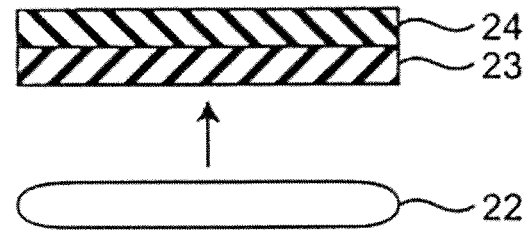
Figure 11C:
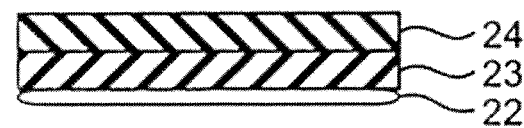

FIGS. 11A to 11C are lateral cross-sectional views illustrating steps of a method for manufacturing the belt 20 shown in FIG. 1. As illustrated in FIG. 11A, first, the reinforcing layer 23 is prepared and resin that forms the material of the outer circumferential layer 24 is laid on the outer surface of the reinforcing layer 23 through insert molding. The fluid bladder 22 prepared in advance is adhered or welded as illustrated in FIG. 11B along the inner surface of the reinforcing layer 23 of the intermediate body composed of the reinforcing layer 23 and the outer circumferential layer 24, which were integrated in this manner. In this manner, as illustrated in FIG. 11C, a belt 20 with a three-layer structure, which includes the outer circumferential layer 24, the reinforcing layer 23, and the fluid bladder 22, is formed. Note that in order to facilitate understanding, in the drawings, the resin that forms the material of the outer circumferential layer 24 is denoted by the same reference numeral as the outer circumferential layer 24.

Figure 12A:
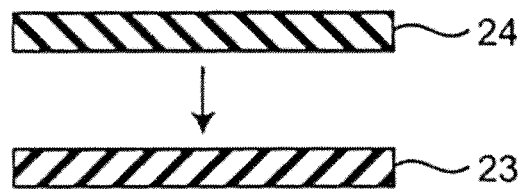
FIGS. 12A, 12B, and 12C show lateral cross-sectional views illustrating a step of a method for manufacturing the belt 20 in FIG. 1, according to a modified example of an embodiment of the present invention.
Figure 12B:
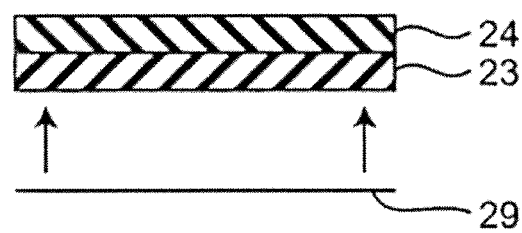
Figure 12C:
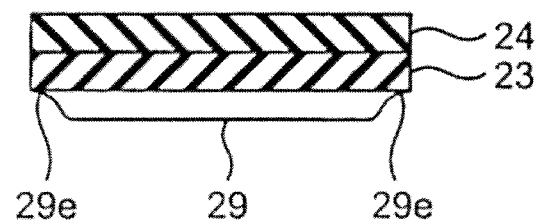

FIGS. 12A to 12C are lateral cross-sectional views illustrating steps of a method for manufacturing the belt 20 shown in FIG. 1, according to a modified example of an embodiment of the present invention. As illustrated in FIG. 12A, first, the reinforcing layer 23 is prepared and resin that forms the material of the outer circumferential layer 24 is laid on the outer surface of the reinforcing layer 23 through insert molding. Next, as illustrated in FIG. 12B, an intermediate body composed of the reinforcing layer 23 and the outer circumferential layer 24 is manufactured. Also, one sheet 29 is prepared in addition to this. Finally, the fluid bladder 22 composed of the reinforcing layer 23 and the sheet 29 is formed by adhering or welding the circumferential edge portions 29e of the sheet 29 prepared in advance along the inner surface of the reinforcing layer 23 of the intermediate body manufactured as illustrated in FIG. 12C. In this manner, a belt 20 with a three-layer structure including the outer circumferential layer 24, the reinforcing layer 23, and the fluid bladder 22 can be manufactured easily. Note that in order to facilitate understanding, in the drawings, the resin that forms the material of the outer circumferential layer 24 is denoted by the same reference numeral as the outer circumferential layer 24.

Note that the above-described reinforcing layer 23 need not be present, and in such a case, the portion of the reinforcing layer is formed as the outer circumferential layer.

As can be understood from FIGS. 1A, 1B, and 3, an operation portion that includes a blood pressure measurement switch 52B for inputting an instruction to measure bodily information is arranged at a site (in this example, the approximate center portion) that is different from a specific portion (in this example, the base end portion a) at which the main body 10 is arranged in the lengthwise direction of the belt 20. Also, as shown in FIG. 5, an FPC cable 54 that electrically connects the main body 10 and the operation portion 52 is interposed between the fluid bladder 22 and the reinforcing layer 23. Thus, since the main body 10 and the operation portion 52 are electrically connected by the FPC cable 54, the belt 20 can be made thin. Note that in the present embodiment, only the operation unit is arranged, but the present invention is not limited to this, and a communication unit and a display unit may be arranged.

As can be understood from FIG. 2, magnets 33 are provided on the inner surface side of the base end portion a of the belt 20, protruding portions 31 made of metal that sticks to the magnets 33 are provided on the second plate frame member 30b, and thus the sticking mechanism is formed. With this sticking mechanism, the inner surface side of the base end portion a of the belt 20 or the one end portion d of the first plate frame member 30a and the other end portion h of the second plate frame member 30b can stick to each other. Accordingly, when the main body 10, the first plate frame member 30a, and the second plate frame member 30b of the buckle 30 are folded in on each other, the inner surface of the main body 10, the first plate frame member 30a, and the second plate frame member 30b of the buckle 30 are guided so as to overlap.

Note that in addition to or instead of the above-described sticking mechanism, it is desirable to include a lock mechanism that allows the inner surface side of the base end portion a of the belt 20 or the one end portion d of the first plate frame member 30a and the other end portion h of the second plate frame member 30b to engage with each other. Also, the sticking mechanism and/or the lock mechanism preferably include an unlocking mechanism for removing the sticking and/or the engagement. In this example, a release button 19 (see FIGS. 1A, 2, and 5) for removing the sticking is provided as an unlocking mechanism on the main body 10. As shown in FIG. 5, a slide board 19a is integrally formed on the release button 19. When the release button 19 is pressed toward the interior of the main body 10, the slide board 19a enters like a wedge between the one end portion d of the first plate frame member 30a and the other end portion h of the second plate frame member 30b shown in FIG. 6B, and the sticking between the first plate frame member 30a and the second plate frame member 30b is removed.

Figure 6A:
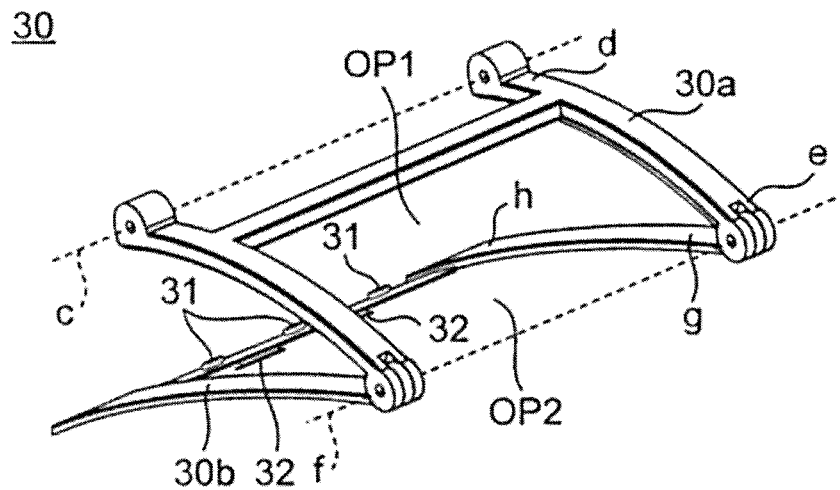
FIG. 6A is a schematic perspective view for illustrating a first state of operations of a buckle 30 in FIG. 5.
Figure 6B:
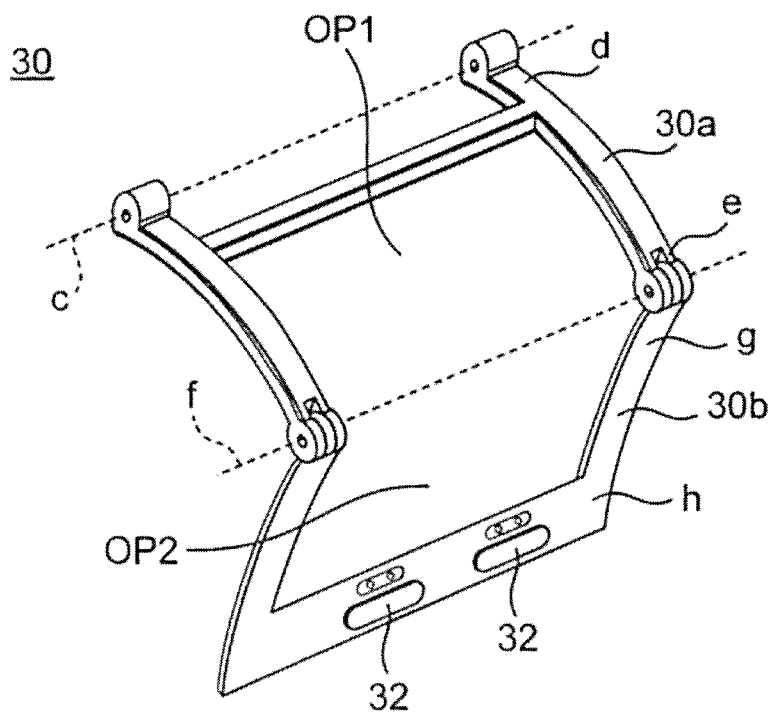
FIG. 6B is a schematic perspective view for illustrating a second state of operations of the buckle 30 in FIG. 5.

As shown in FIGS. 6A and 6B, a first fixing element, which includes engaging portions 32 having protruding shapes, is provided on the inner surface of the other end portion h of the second plate frame member 30b, and as shown in FIGS. 1A, 1B, and 5, a second fixing element, which includes engaged portions 25 having recessed shapes that can engage with the engaging portions 32, is provided on the outer surface of the leading end portion b of the belt 20. Accordingly, as shown in FIGS. 3 and 4, the second plate frame member 30b and the leading end portion b of the belt 20 can be engaged such that the belt 20 is made into a loop shape. Accordingly, the bodily information measurement apparatus 1 can be fixed to the measurement site. Furthermore, since the non-through, recessed second fixing elements (engaged portions 25), which are formed so as to be able to be engaged with the protruding first fixing elements (engaging portions 32), are provided on the outer surface of the leading end portion b of the belt 20, the fixing elements no longer interfere with the fluid bladder 22. Accordingly, the wrist 90 serving as the measurement site can be reliably compressed by the fluid bladder 22 during blood pressure measurement.

Also, as a conventional technique, for example, Patent Documents 2 and 3 disclose watch-type blood pressure measurement devices with an arm-wrapping belt (band) on which a cuff (air bladder) is attached, the arm-wrapping belt being attached to both sides of a main body and being fixed to the arm using an adjustment belt. However, with these blood pressure measurement devices, if the cuff includes a normal watch-type belt that extends to both sides of the main body, the joining portion is located near the radial artery, and therefore the radial artery cannot be compressed correctly and the blood pressure cannot be measured accurately.

Furthermore, Patent Document 4 discloses a watch-type blood pressure monitor with an arm belt (band) made of cloth that extends from one end of a blood pressure monitor main body portion, the leading end of the arm belt being passed through a band link provided on the end portion on the side opposite to the main body, folded over, and fixed with Magic Tape (registered trademark). A cuff is constituted such that an air bladder composed of a nylon upper portion and a nylon lower portion is stored inside of the band (cuff case) of the watch-type blood pressure monitor. Here, the cuff is formed so as to be short enough to cover the blood pressure measurement portion and the pump portion so that the cuff is located near the artery, and the main body portion is rotated inward of the wrist during blood pressure measurement. However, since the cuff is not formed so as to go around the wrist, the blood pressure cannot be measured accurately in the state in which the main body portion is located on the backhand side of the wrist. Even if the cuff is extended to the leading end of the band, the cuff will break at the band ring portion or the folded-over portion of the cuff will become thick, whereby the appearance of the wearable device will deteriorate.

In comparison with the conventional technique, as can be understood from FIG. 4, the buckle 30 of the bodily information measurement apparatus 1 according to the present embodiment differs in that it serves as a fastening portion for fastening a base end portion a and a leading end portion b on the side opposite thereto in the lengthwise direction of the belt 20, so that the belt 20 forms a loop shape. In other words, in the state in which the base end portion a of the belt 20 and the leading end portion b of the belt 20 overlap, the base end portion a and the leading end portion b are fastened and are attached to the wrist 90 serving as the measurement site by the buckle 30. With this configuration, the base end portion a of the belt 20 and the leading end portion b of the belt 20 overlap when the base end portion a of the belt 20 and the leading end portion b of the belt 20 are fastened. For this reason, the degree of swelling of the fluid bladder 22 on the backhand side of the wrist, or in other words, the swelling of the fluid bladder 22 in the thickness direction, increases, and therefore the pulse can be detected accurately. Accordingly, the blood pressure measurement accuracy improves. Furthermore, the appearance improves without the leading end portion b of the belt 20 protruding in the fastened state.

Note that in the present embodiment, a protruding shape was used as the first fixing element and a recessed shape was used as the second fixing element, but the present invention is not limited thereto. For example, a recessed shape may be used as the first fixing element and a protruding shape may be used as the second fixing element. In this case as well, an effect similar to that of the present embodiment can be obtained.

As can be understood from FIGS. 1A, 1B, and 5, the engaged portions 25 are formed in alignment in the lengthwise direction of the belt 20 so as to enable adjustment of the attachment position of the other end portion h of the second plate frame member 30b in the lengthwise direction of the belt 20. Accordingly, the attachment position of the other end portion h (see FIG. 6B) of the second plate frame member 30b can be adjusted in the lengthwise direction of the belt 20. Accordingly, the length of the loop of the belt 20 can be set variably so as to exactly match the circumferential length of the wrist 90 serving as the measurement site.

Also, the multiple (in this example, 2) engaged portions 25 are formed in alignment in the width direction of the belt 20. Accordingly, even if the belt 20 twists slightly, the engagement between the engaging portions 32 and the engaged portions 25 is not likely to come off.

Also, at least the outer surface of the leading end portion b of the belt 20 is composed of a flexible material. Accordingly, it is easy to remove the engagement between the engaging portions 32 and the engaged portions 25. Note that it is possible to include a removal mechanism (not shown) according to which the user removes the locking between the engaging portions 32 and the engaged portions 25. In this case, in the state in which the belt 20 is attached to the wrist 90, the user can remove the locking between the engaging portions 32 and the engaged portions 25 using the removal mechanism. Accordingly, removal of the belt 20 is even easier.

FIG. 6A is a schematic perspective view for illustrating a first state of operations of the buckle 30 shown in FIG. 5, and FIG. 6B is a schematic perspective view for illustrating a second state of operations of the buckle 30 shown in FIG. 5.

The buckle 30 includes a first plate frame member 30a that is attached at the one end portion d so as to be able to rotate about the axis c that intersects with the lengthwise direction of the belt 20 on the inner surface side of the base end portion a of the belt 20, and the first plate frame member 30a extends in a curved manner in the form of a plate from the one end portion d to the other end portion e on the opposite side. Also, the second plate frame member 30b attached so as to be able to rotate about an axis f that is parallel to an axis c is included on the other end portion e of the first plate frame member 30a, and the second plate frame member 30b extends in a curved manner in the form of a plate from the one end portion g to the other end portion h on the opposite side.

Furthermore, the other end portion h of the second plate frame member 30b is formed so as to be able to attach to the leading end portion b of the belt 20, and the first plate frame member 30a and the second plate frame member 30b include a first opening portion OP1 and a second opening portion OP2 that penetrate through the plate surfaces of the respective members. Here, in a state in which the inner surface of the main body 10, the first plate frame member 30a, and the second plate frame member 30b of the buckle 30 are folded over so as to overlap, the first opening portion OP1 of the first plate frame member 30a and the second opening portion OP2 of the second plate frame member 30b are continuous in the thickness direction of the main body 10.

Accordingly, it is possible to use a configuration in which the fluid bladder 22 is arranged so as to compress the measurement site on the inner side of the main body 10.

The first opening portion OP1 opens toward the other end portion e side of the first plate frame member 30a, the second opening portion OP2 opens toward the one end portion g side of the second plate frame member 30b, and the first opening portion OP1 and the second opening portion OP2 are in communication. In other words, the first plate frame member 30a and the second plate frame member 30b are formed into an approximate U shape, and are joined together at the sides at which the opening portions are open. Also, as can be understood from FIG. 2, the fluid bladder 22 for compressing the measurement site during blood pressure measurement is provided along the lengthwise direction of the belt 20 in the belt 20, and the fluid bladder 22 is in communication with the interior of the main body 10 through the region corresponding to the first opening portion OP1 and the second opening portion OP2 in the folded state.

With this configuration, the region of the wrist 90 serving as the measurement site that is spatially continuous from the portion corresponding to the inside of the main body 10 to the leading end portion b of the belt 20 in the circumferential direction can be compressed with the fluid bladder 22. Accordingly, since it is possible to further increase the area with which the air bladder 22 and the measurement site come into contact, the efficiency of compressing the artery can be improved. Accordingly, the blood pressure measurement accuracy can be further increased.

Also, the fluid bladder 22 extends in the lengthwise direction to the leading end portion b of the belt 20. Also, in the state in which the inner surface of the main body 10, the first plate frame member 30a, and the second plate frame member 30b of the buckle 30 are folded so as to overlap, the portion of the main body 10 with which the fluid bladder 22 is in communication overlaps with the portion of the belt 20 at which the fluid bladder 22 is present.

Due to this configuration, the above-described region of the belt 20 that overlaps in the lengthwise direction expands by an amount corresponding to the thickness, which is larger than the thickness of the other regions of the main body 10. Accordingly, the distance by which the artery in the wrist 90 is pushed away by the regions other than the overlapping region decreases, and the extra pressure increase amount for pressing down the artery decreases. As a result, the measurement value of the blood pressure measured by inflating the fluid bladder can be brought closer to the true value, and the measurement accuracy can be increased. Note that the effect of being able to reduce the extra pressure increase amount for pressing down the artery is also achieved in the case where the first opening portion OP1 of the first plate frame member 30a and the second opening portion OP2 of the second plate frame member 30b are omitted in the buckle 30.

Figure 7A:
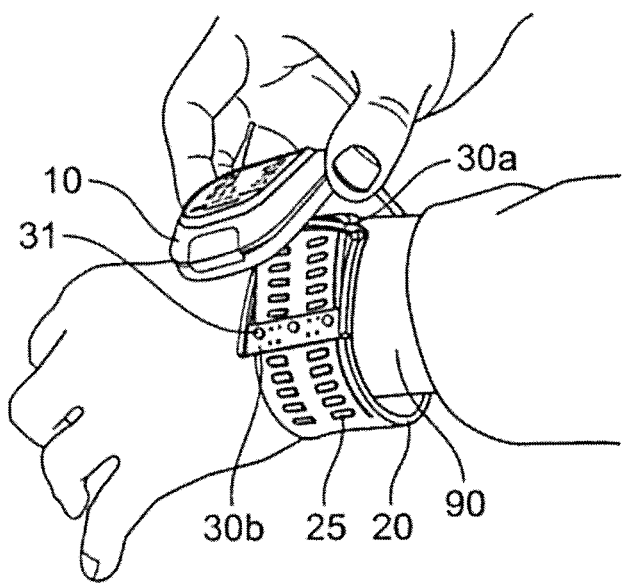
FIG. 7A is a schematic diagram for illustrating a first procedure of performing measurement with the bodily information measurement apparatus 1 in FIG. 1 attached to the wrist.
Figure 7B:
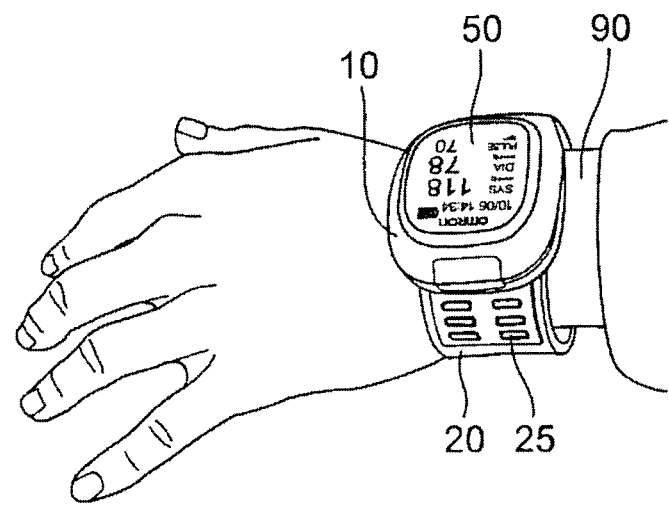
FIG. 7B is a schematic diagram for illustrating a second procedure of performing measurement with the bodily information measurement apparatus 1 in FIG. 1 attached to the wrist.
Figure 7C:
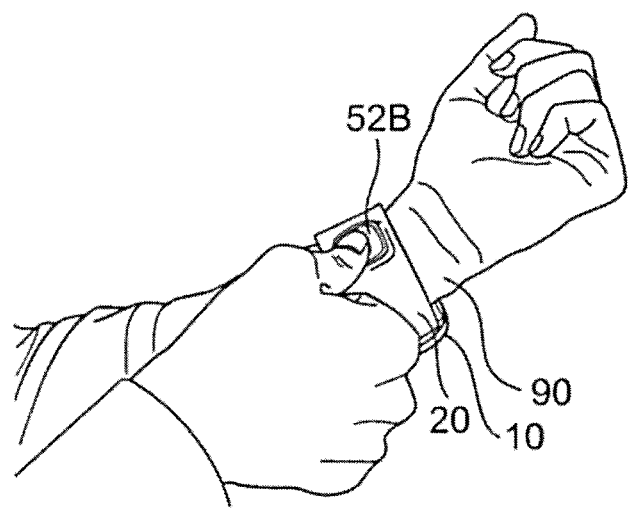
FIG. 7C is a schematic diagram for illustrating a third procedure of performing measurement with the bodily information measurement apparatus 1 in FIG. 1 attached to the wrist.

FIGS. 7A to 7C are schematic diagrams for illustrating a procedure of attaching the bodily information measurement apparatus 1 shown in FIG. 1 to a wrist and performing measurement. When the bodily information measurement apparatus 1 is actually attached to the wrist 90, as shown in FIG. 7A, the user first aligns the belt 20 with the wrist 90 in the state in which the main body 10, the first plate frame member 30a, and the second plate frame member 30b of the buckle 30 are open toward each other. Then, the leading end portion b of the belt 20 is passed through the interior of the second opening portion OP2 (see FIGS. 6A and 6B) of the second plate frame member 30b, and the engaging portions 32 of the second plate frame member 30b are engaged with the engaged portions 25 on the leading end portion b side of the belt 20. Accordingly, the belt 20 is made into a loop, and is set to a state in which the wrist 90 is passed through the loop of the belt 20. Thus, the length of the loop of the belt 20 is set so as to exactly match the circumferential length of the wrist 90.

Next, as shown in FIG. 7B, the main body 10 is brought close to the wrist 90 side, and the inner surface of the main body 10, the first plate frame member 30a, and the second plate frame member 30b of the buckle 30 are folded so as to overlap. Upon doing so, the protrusions 31 of the second plate frame member 30b stick to the magnet 33, whereby the attachment of the bodily information measurement apparatus 1 to the wrist 90 is complete. Next, as shown in FIG. 7C, measurement of the blood pressure is started when the user presses the blood pressure measurement switch 52B.

Figure 8:
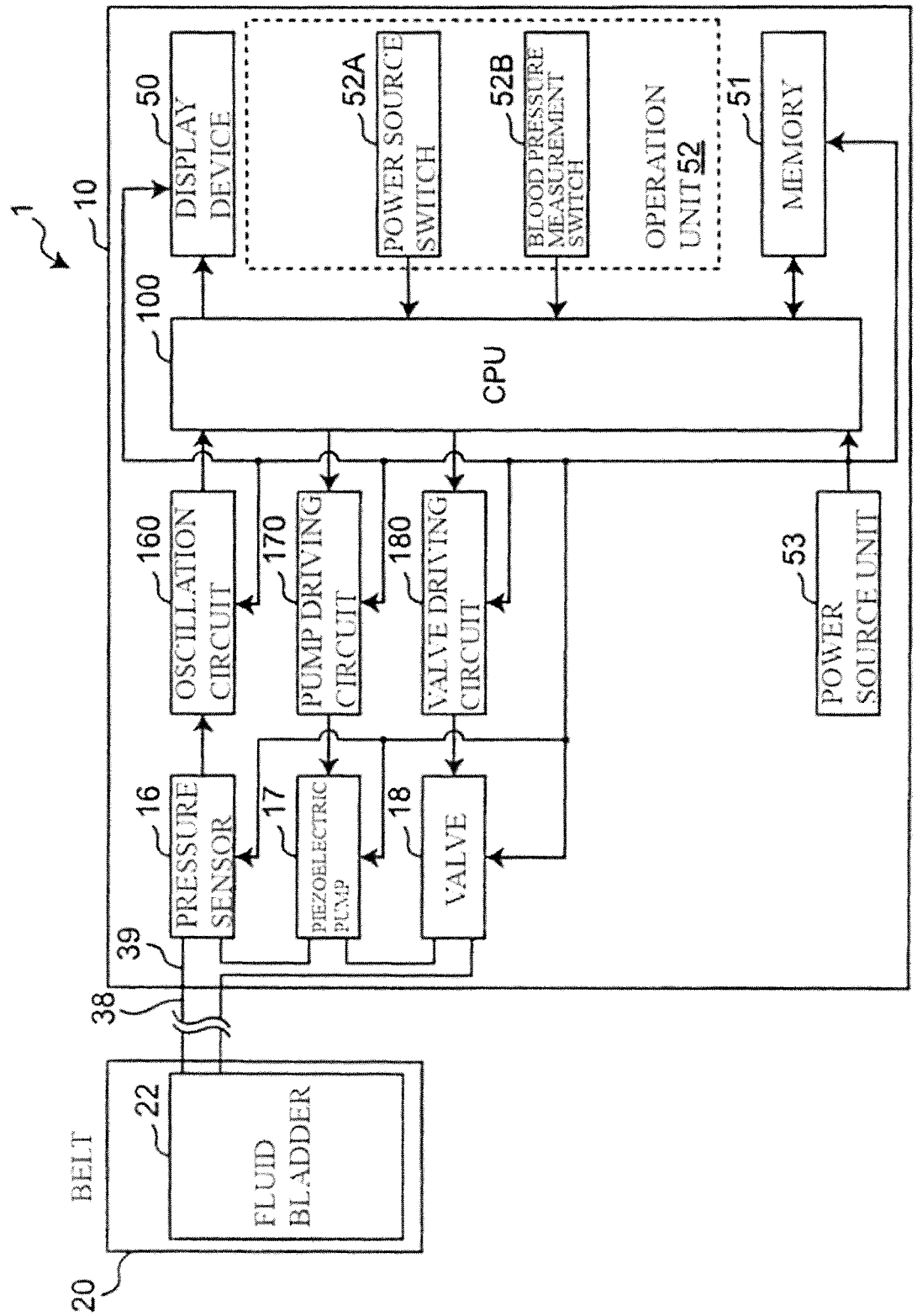
FIG. 8 is a block diagram schematically showing a configuration of control system inside of the bodily information measurement apparatus 1 in FIG. 1.

FIG. 8 is a block diagram schematically showing an internal configuration of the bodily information measurement apparatus 1 shown in FIG. 1. In addition to the above-described display device 50 and the operation unit 52, the main body 10 is provided with a CPU (Central Processing Unit) 100, a memory 51, a power source unit 53, a piezoreistant pressure sensor 16, a piezoelectric pump 17, which is a piezoelectric pump that supplies air serving as a fluid to the fluid bladder 22, a valve 18 for adjusting the pressure (back pressure) on the discharge side of the piezoelectric pump 17, an oscillation circuit 160 that converts the output from the pressure sensor 16 into a frequency, a pump driving circuit 170 that drives the piezoelectric pump 17, and a valve driving circuit 180 that drives the valve 18. The pressure sensor 16, the piezoelectric pump 17, and the valve 18 are connected to the fluid bladder 22 contained in the belt 20 via an air tube 39 provided inside of the main body and a nipple 38 (see FIG. 5) that fits in and is in communication with the air tube 39. Accordingly, the air serving as the fluid flows through the gap between the pressure sensor 16, piezoelectric pump 17, and valve 18, and the fluid bladder 22.

The display device 50 includes a display, an indicator, and the like, and displays predetermined information in accordance with the control signal from the CPU 100.

With the operation unit 52, the power switch 52A receives an instruction to turn on or off the power source unit 53 and an instruction to start blood pressure measurement. The blood pressure measurement switch 52B receives an instruction to display the data of the measurement results of the blood pressure values stored in the memory 51 on the display device 50. The switches 52A and 52B input operation signals corresponding to instructions given by the user to the CPU 100.

The memory 51 stores programs for controlling the bodily information measurement apparatus 1, setting data for setting various functions of the bodily information measurement apparatus 1, and data of measurement results of blood pressure values. Also, the memory 51 is used as a work memory or the like for when a program is executed.

The power source unit 53 supplies power to the units, namely, the CPU 100, the pressure sensor 16, the piezoelectric pump 17, the valve 18, the display device 50, the memory 51, the oscillation circuit 160, the pump driving circuit 170, and the valve driving circuit 180.

The oscillation circuit 160 oscillates based on an electric signal value based on changes in electrical resistance caused by a piezoreistant effect from the pressure sensor 16 and outputs the frequency signal including the frequency corresponding to the electrical signal value of the pressure sensor 16 to the CPU 100.

The CPU 100 functions as a back pressure control unit in accordance with a program for controlling the bodily information measurement apparatus 1 stored in the memory 51 so as to perform control for driving the piezoelectric pump 17 via the pump driving circuit 170 according to the operation signals from the operation unit 52, and driving the valve 18 via the valve driving circuit 180. The valve 18 opens and closes so as to control the back pressure by discharging or sealing the air in the air bladder 22. Also, the CPU 100 calculates the blood pressure values based on the signal from the pressure sensor 16 and controls the display device 50 and the memory 51.

The piezoelectric pump 17 supplies air as a fluid to the fluid bladder 22 in order to increase the pressure (back pressure) in the fluid bladder 22 contained in the belt 20. The valve 18 opens and closes so as to control the back pressure by discharging or sealing the air in the air bladder 22. The pump driving circuit 170 drives the piezoelectric pump 17 based on the control signal provided by the CPU 100. The valve driving circuit 180 opens and closes the valve 18 based on the control signal provided by the CPU 100.

The pressure sensor 16 and the oscillation circuit 160 operate as a pressure detection unit that detects back pressure. The pressure sensor 16 is, for example, a piezoreistant pressure sensor, and is connected via the air tube 39 to the piezoelectric pump 17, the valve 18, and the fluid bladder 22 contained in the belt 20. In this example, the oscillation circuit 160 oscillates based on an electric signal value based on changes in electrical resistance caused by a piezoreistant effect from the pressure sensor 16 and outputs the frequency signal including the frequency corresponding to the electrical signal value of the pressure sensor 16 to the CPU 100.

Operations of the bodily information measurement apparatus 1 configured as described above will be described below.

Figure 9:
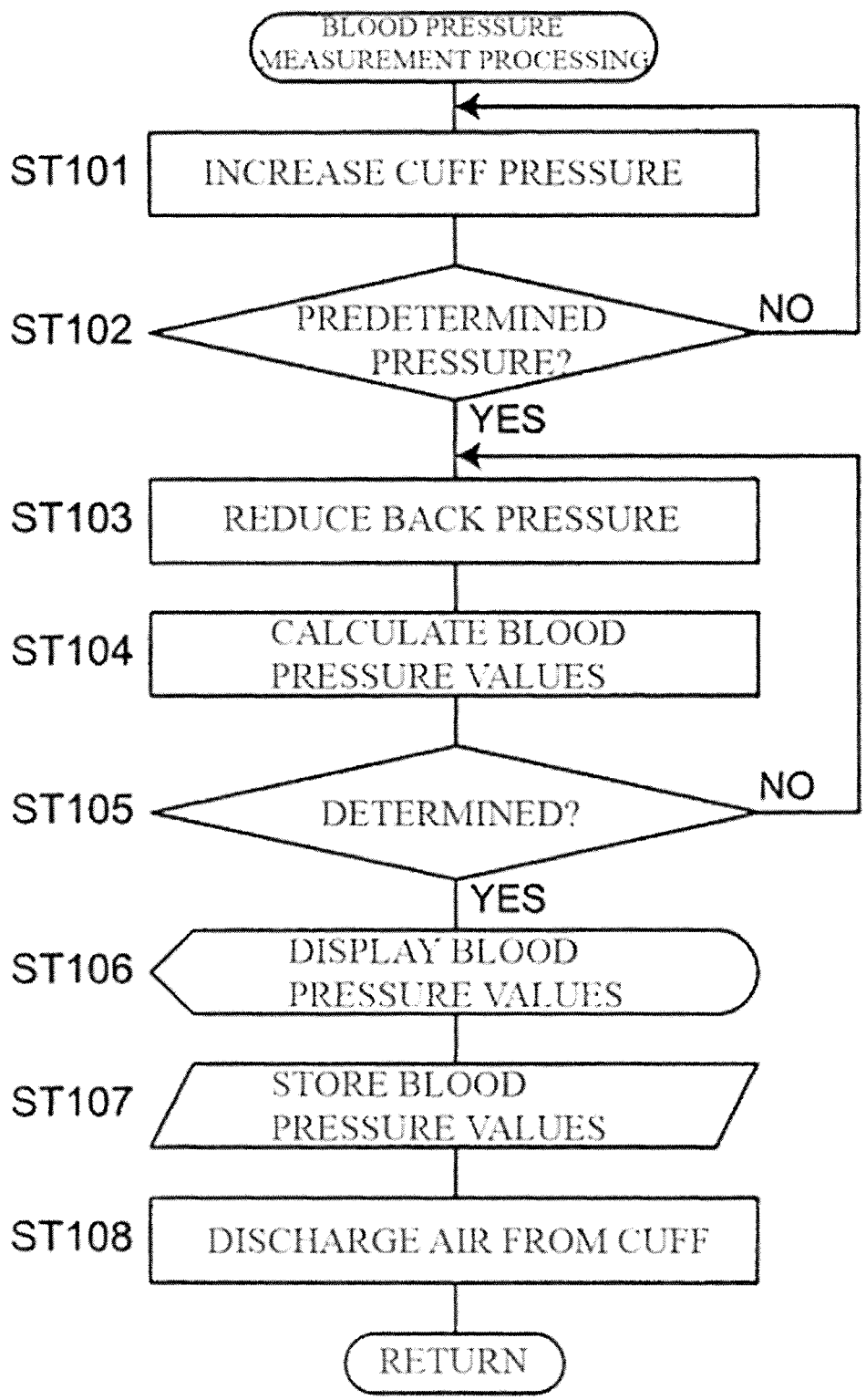
FIG. 9 is a flowchart showing blood pressure measurement processing executed by the bodily information measurement apparatus 1 in FIG. 1.
Figure 10:
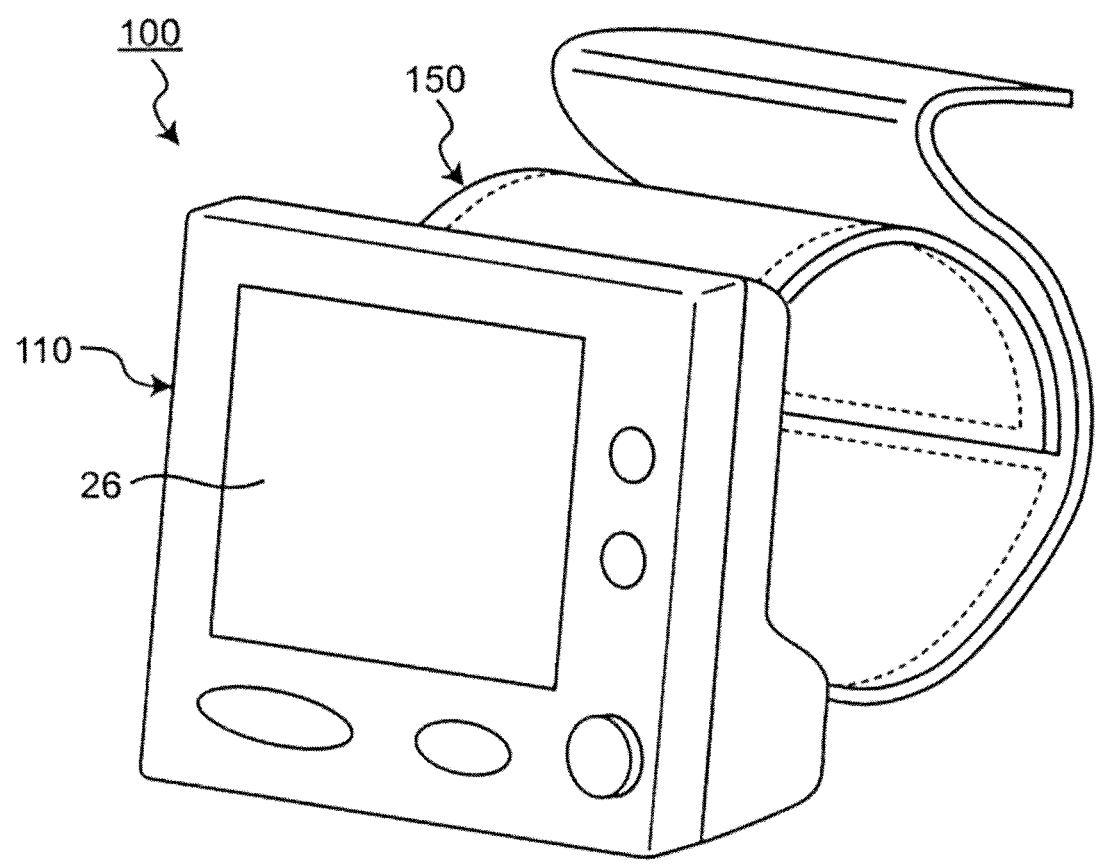
FIG. 10 is a schematic perspective view showing an exterior of a conventional wrist-type blood pressure monitor 100.

FIG. 9 is a flowchart showing blood pressure measurement processing executed by the bodily information measurement apparatus 1 shown in FIG. 1. In the case of measuring the blood pressure in accordance with a common oscillometric method, the following operations are generally performed. In other words, the cuff is wrapped around the measurement site (wrist, etc.) of the user in advance, and during measurement, the pump and valve are controlled, the back pressure is increased to be greater than the systolic blood pressure, and thereafter the back pressure is gradually reduced. In the process of reducing the pressure, the back pressure is detected by the pressure sensor, and the variation in the artery volume that occurs in the artery at the measurement site is taken as a pulse wave signal. The systolic blood pressure and the diastolic blood pressure are calculated based on changes in the amplitude of the pulse wave signal accompanying changes in the back pressure at this time (mainly rising edges and falling edges).

With the bodily information measurement apparatus 1, the blood pressure values of the user are measured by the CPU 100 using an oscillometric method according to the flow shown in FIG. 9.

Specifically, when the measurement switch 52B is pressed while the power source switch 52A is on, the bodily information measurement apparatus 1 starts blood pressure measurement as shown in FIG. 9. At the start of blood pressure measurement, the CPU 100 initializes the memory region for processing and outputs a control signal to the valve driving circuit 180. Based on the control signal, the valve driving circuit 180 opens the valve 18 to discharge the air in the fluid bladder 22 of the belt 20. Next, control for adjusting the pressure sensor 16 to 0 mmHg is performed.

In FIG. 9, when the blood pressure measurement is started, first, the CPU 100 closes the valve 18 via the valve driving circuit 180, and thereafter, drives the pump 32 via the pump driving circuit 170 to perform pressure increase processing for sending air to the fluid bladder 22. Accordingly, the fluid bladder 22 is inflated and the back pressure gradually increases (step ST101).

When the cuff pressure is increased and reaches a predetermined cuff pressure (YES in step ST102), the CPU 100 stops the pump 32 via the pump driving circuit 170 and thereafter performs control for gradually opening the valve 18 via the valve control circuit 180. Accordingly, the fluid bladder 22 contracts and the back pressure gradually decreases (step ST103).

Here, the predetermined pressure is a pressure that is sufficiently higher than the systolic blood pressure of the user (e.g., systolic blood pressure+30 mmHg), and is stored in the memory 51 in advance or is determined by the CPU 100 estimating the systolic blood pressure using a predetermined calculation method while the back pressure is increasing (e.g., see JP 2001-70263A).

Also, regarding the pressure decrease speed, a target pressure decrease speed is set while the pressure in the cuff is increased, and the CPU 100 controls the opening degree of the valve 18 so as to reach the target pressure decrease speed (see JP 2001-70263A).

In the process of reducing the pressure, the pressure sensor 16 detects a back pressure signal (indicated by reference sign Pc) that indicates the pressure of the belt 20, via the belt 20. Based on the back pressure signal Pc, the CPU 100 calculates the blood pressure values (systolic blood pressure and diastolic blood pressure) by applying a later-described algorithm through the oscillometric method (step ST104). Note that the calculation of the blood pressure values is not limited to being performed during the pressure reduction process and may be performed during the pressure increase process.

When the blood pressure values are calculated and determined (YES in step ST105), the CPU 100 displays the calculated blood pressure values on the display device 50 (step ST106) and performs control for storing the blood pressure values in the memory 51 (step ST107).

Next, the CPU 100 opens the valve 18 via the valve driving circuit 180 and performs control for discharging the air in the fluid bladder 22 of the belt 20 (step ST108).

Thereafter, when the power source switch 52A is pressed, the blood pressure measurement ends.

In the case of removing the bodily information measurement apparatus 1 from the wrist 90, the user opens the first plate frame member 30a and the second plate frame member 30b of the buckle 30 and removes the wrist 90 from the belt 20 in a state in which the loop of the belt 20 has been made larger.

During the second and subsequent instances of attaching, the wrist 90 need only be passed through the loop of the belt 20 in a state in which the first plate frame member 30a and the second plate frame member 30b of the buckle 30 are open, and the buckle 30 need only be closed. Accordingly, the user can easily attach the bodily information measurement apparatus 1 to the wrist 90.

Modified Example 1 of First Embodiment

Figure 17A:
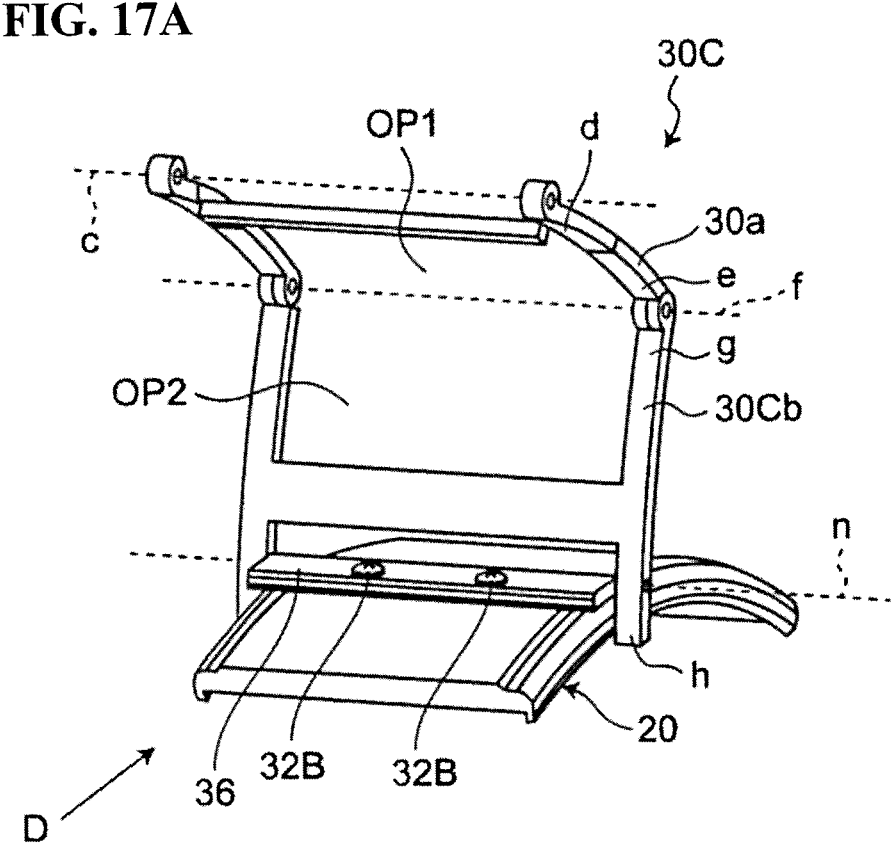
FIG. 17A is a perspective view showing a first state of the buckle 30C at a time when the buckle 30C according to Modified Example 1 of the first embodiment of the present invention is attached to the belt 20.
Figure 17B:
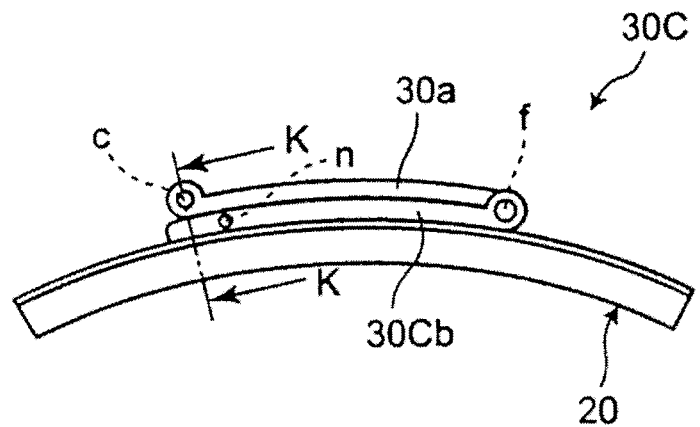
FIG. 17B is a side view showing a second state at a time when the buckle 30C in FIG. 17A is attached to the belt 20.
Figure 17C:
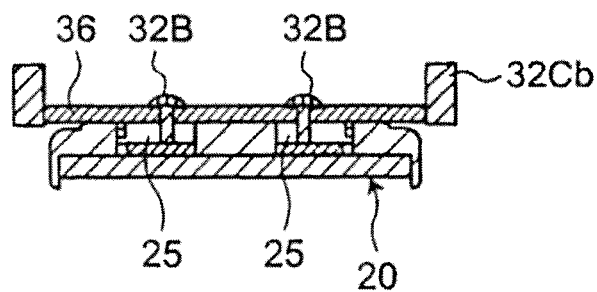
FIG. 17C is a lateral cross-sectional view taken along line K-K in FIG. 17B.

FIG. 17A is a perspective view showing a first state of the buckle 30C at a time when a buckle 30C according to Modified Example 1 of the first embodiment is attached to the belt 20. FIG. 17B is a side view (a side view taken in the direction of arrow D in FIG. 17A) showing a second state at a time when the buckle 30C shown in FIG. 17A is attached to the belt 20. FIG. 17C is a lateral cross-sectional view taken along line K-K in FIG. 17B.

The buckle 30C shown in FIG. 17 differs in comparison to the buckle 30 according to the first embodiment in that a second plate frame member 30Cb is included instead of the second plate frame member 30b. As shown in FIG. 17A, in comparison to the second plate frame member 30b according to the first embodiment, the second plate frame member 30Cb differs in that a plate-shaped plate portion 36 having first fixing elements (fastening screws 32B) that can rotate about an axis n that is parallel to an axis c is attached to one end portion h of the second plate frame member 30Cb. Screw-holes that are penetrated by the fastening screws 32B, which are the first fixing elements, are formed in the plate portion 36. Due to the leading end portion of the fastening screw 32B reaching the bottom portion of the engaged portion 25 (second fixing element) via the screw hole, the second plate frame member 30Cb can be fixed to the belt 20 (see FIG. 17C).

With this configuration, the first fixing elements (fastening screws 32B) can rotate with respect to the belt 20, and therefore the first fixing elements (fastening screws 32B) are easily engaged with the second fixing elements (engaged portions 25). Accordingly, the length of the loop of the belt 20 is variable and thus is easily set so as to exactly match the circumferential length of the wrist 90 serving as the measurement site. Furthermore, since the fastening screw 32B is formed on the plate portion 36, which can be rotated with respect to the second plate frame member 30Cb, the plate portion 36 rotates even if a force is applied in the direction in which the fastening screws 32B come out when attaching to the wrist 90. Accordingly, the force applied between the engaged portions 25 and the fastening screws 32B of the belt 20 does not change, and therefore the fastening screws 32B are not likely to come out from the engaged portions 25.

Second Embodiment

Figure 13A:
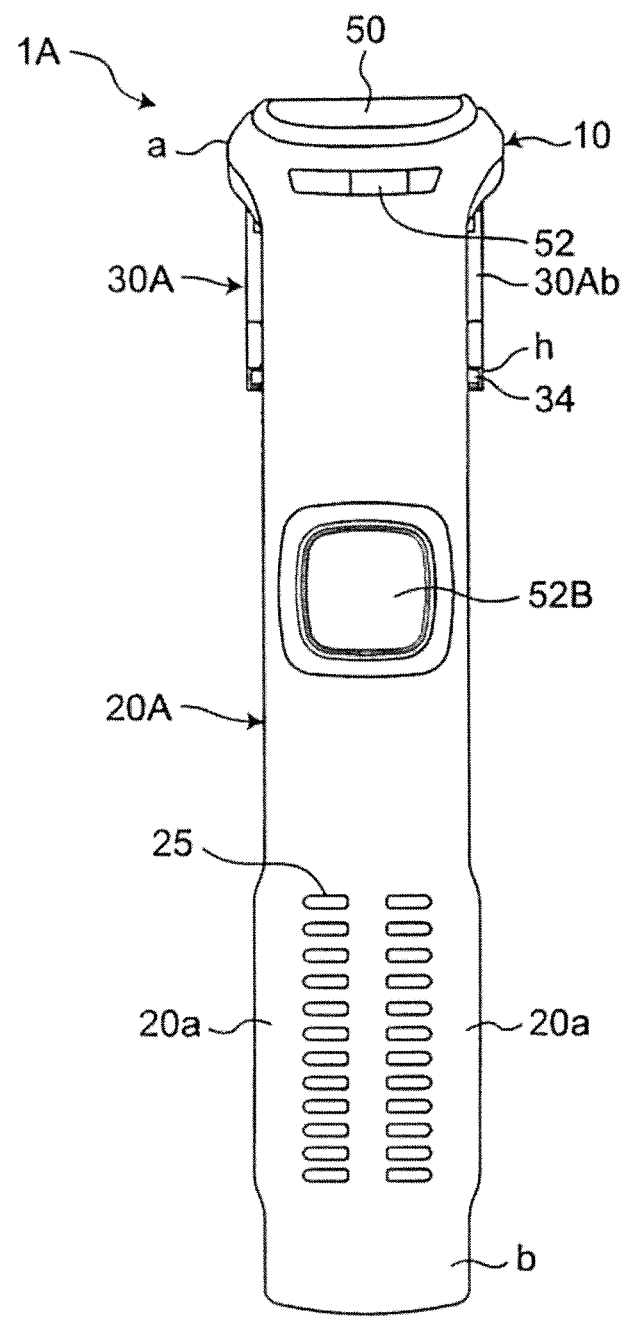
FIG. 13A is a top view showing an exterior of a bodily information measurement apparatus 1A according to a second embodiment of the present invention.
Figure 13B:
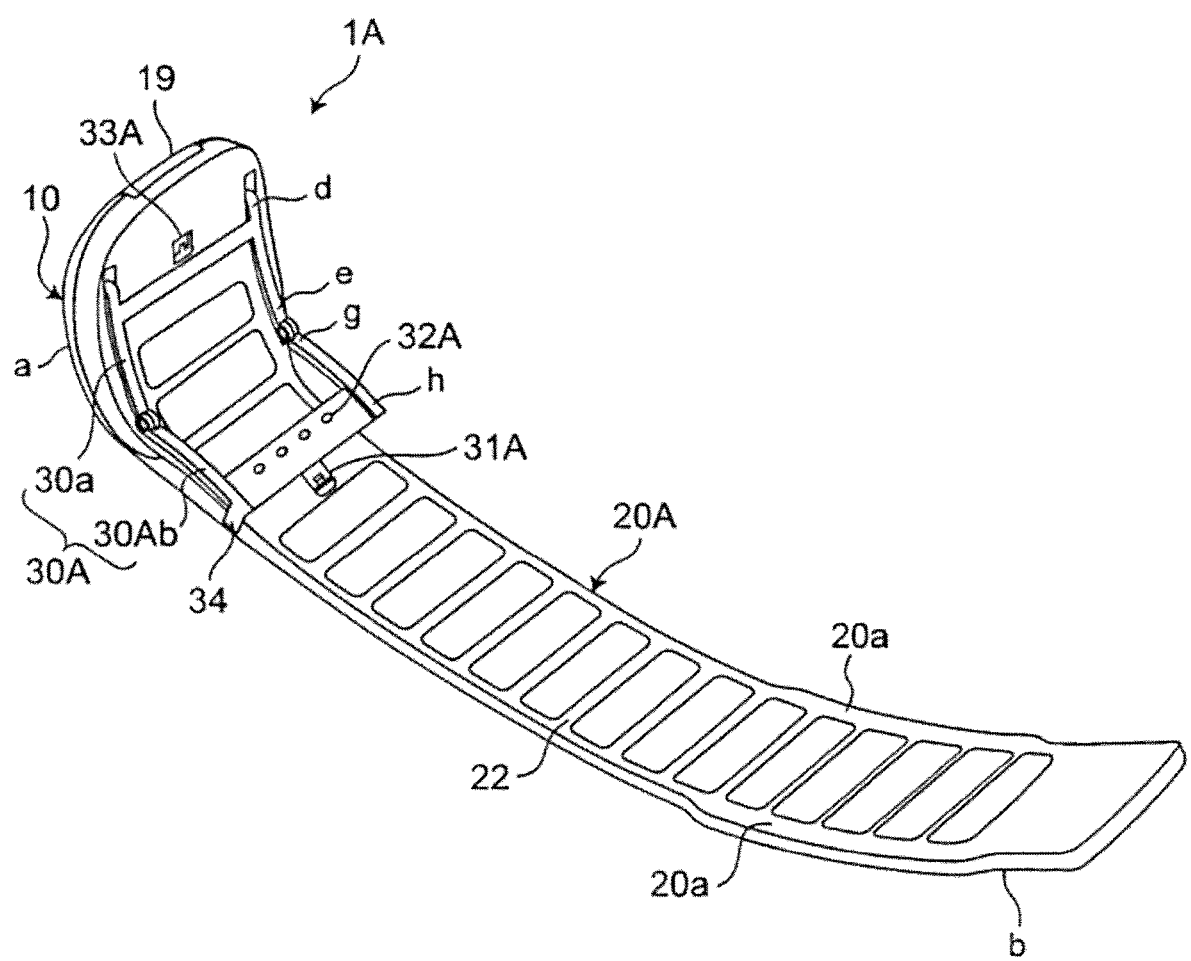
FIG. 13B is a bottom view of the bodily information measurement apparatus 1A in FIG. 13A.

FIG. 13A is a top view showing the exterior of a bodily information measurement apparatus 1A according to a second embodiment of the present invention. FIG. 13B is a bottom view of the bodily information measurement apparatus 1A shown in FIG. 13A, and FIG. 13C is a perspective view showing a state at a time of attaching the bodily information measurement apparatus 1A shown in FIG. 13A by wrapping it around a measurement site.

As shown in FIG. 13A, in comparison to the bodily information measurement apparatus 1 according to the first embodiment, the bodily information measurement apparatus 1A according to the present embodiment differs in that a belt 20A is included instead of the belt 20 and a buckle 30A is included instead of the buckle 30.

Also, as can be understood from FIGS. 13A and 13B, in comparison to the belt 20 according to the first embodiment, the belt 20A according to the present embodiment differs in that wide portions 20a are provided in the width direction, which is perpendicular to the lengthwise direction of the belt 20A. The wide portions 20a are formed on both sides of the second fixing elements (engaged portions 25) in the width direction. In other words, the engaged portions 25 is formed in a wide region of the belt 20A and is formed such that the leading end portion of the belt 20A is wide in the width direction, which is perpendicular to the lengthwise direction of the belt 20A, such that the engaged portions 25 are caught by the leading end portions of later-described hook portions 34.

Figure 13C:
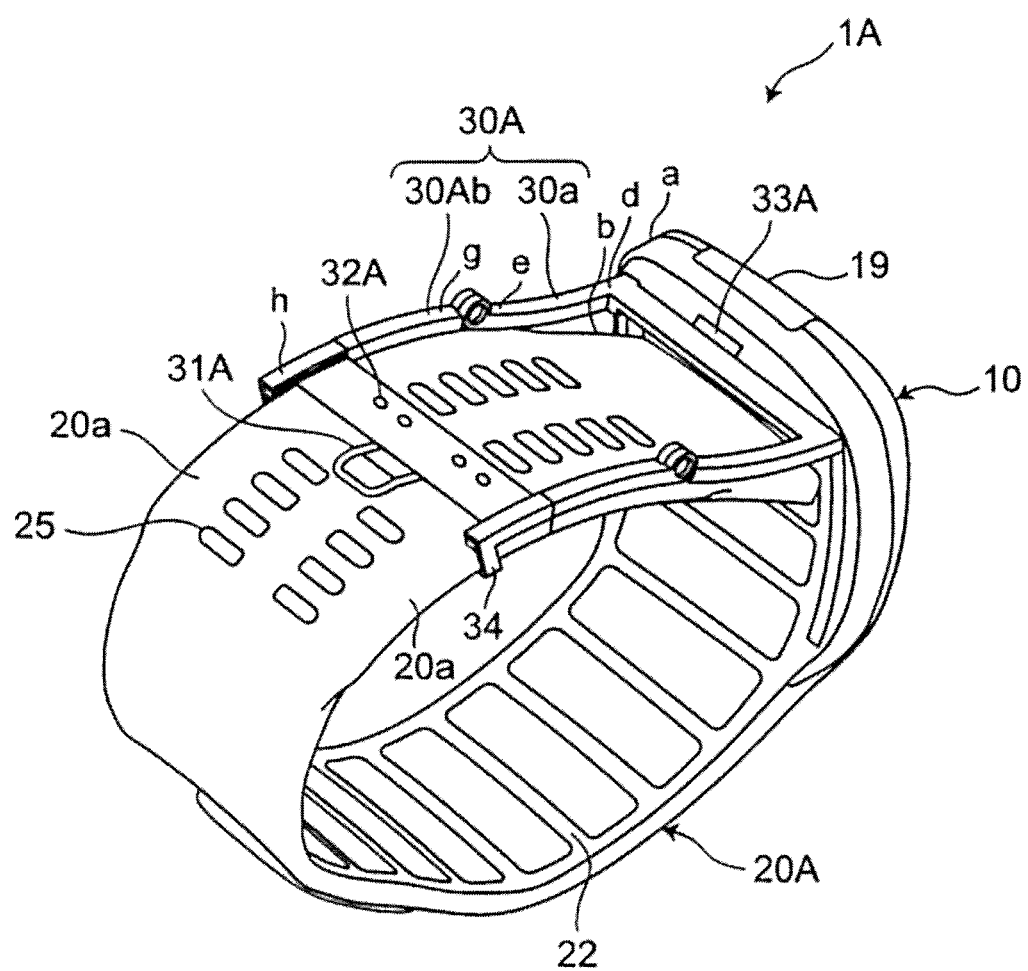
FIG. 13C is a perspective view showing a state at a time of attaching the bodily information measurement apparatus 1 in FIG. 13A by wrapping it around a measurement site.

Also, as can be understood from FIGS. 13B and 13C, in comparison to the buckle 30 according to the first embodiment, the buckle 30A according to the present embodiment differs in that the second plate frame member 30Ab is included instead of the second plate frame member 30b. Here, the first fixing elements including the engaging portions 32A, which have protruding shapes, are provided on the inner surface of the other end portion h of the second plate frame member 30Ab. Along with this, as shown in FIGS. 13A and 13C, second fixing elements including the engaged portions 25, which have recessed shapes that can be engaged with the engaging portion 32A, are provided on the outer surface of the leading end portion b of the belt 20A. Accordingly, as shown in FIG. 13C, the second plate frame member 30Ab and the leading end portion b of the belt 20A can be engaged so as to make the belt 20A into a loop shape. Accordingly, the bodily information measurement apparatus 1A can be fixed to the measurement site. Furthermore, since the non-through, recessed second fixing elements (engaged portions 25), which are formed so as to be able to be engaged with the protruding first fixing elements (engaging portions 32A), are provided on the outer surface of the leading end portion b of the belt 20A, the fixing elements no longer interfere with the fluid bladder 22. Accordingly, the wrist 90 serving as the measurement site can be reliably compressed by the fluid bladder 22 during blood pressure measurement.

As shown in FIGS. 13A, 13B, and 13C, hook-shaped hook portions 34 that are formed so as to protrude are formed on the other end portion h of the second plate frame member 30Ab. The hook portions 34 are locked by catching on the wide portion 20a of the belt 20A. Accordingly, the second plate frame member 30Ab can be reliably fixed to the belt 20A.

As can be understood from FIG. 13B, the engaged portions 33A, which have recessed shapes, are included on the inner surface side of the base end portion a of the belt 20A, and the engaging portions 31A that engage with the engaged portions 33A are included on the second plate frame member 30Ab, and thereby the lock mechanism is configured. With the lock mechanism, it is possible to lock the inner surface side of the base end portion a or the one end portion d of the first plate frame member 30a of the belt 20A together with the other end portion h of the second plate frame member 30Ab. Accordingly, when the main body 10, the first plate frame member 30a, and the second plate frame member 30Ab of the buckle 30A are folded in on each other, the inner surface of the main body 10, the first plate frame member 30a, and the second plate frame member 30Ab of the buckle 30A are fixed so as to overlap.

As can be understood from FIGS. 13A and 13C, multiple engaged portions 25 are formed in alignment in the lengthwise direction of the belt 20A so as to enable the attachment position of the other end portion h of the second plate frame member 30Ab to be adjusted in the lengthwise direction of the belt 20A. Accordingly, the attachment position of the other end portion h (see FIG. 13C) of the second plate frame member 30Ab can be adjusted in the lengthwise direction of the belt 20A. Accordingly, the length of the loop of the belt 20A is variable and thus can be set so as to exactly match the circumferential length of the wrist 90 serving as the measurement site.

Modified Example 1 of Second Embodiment

Figure 15A:
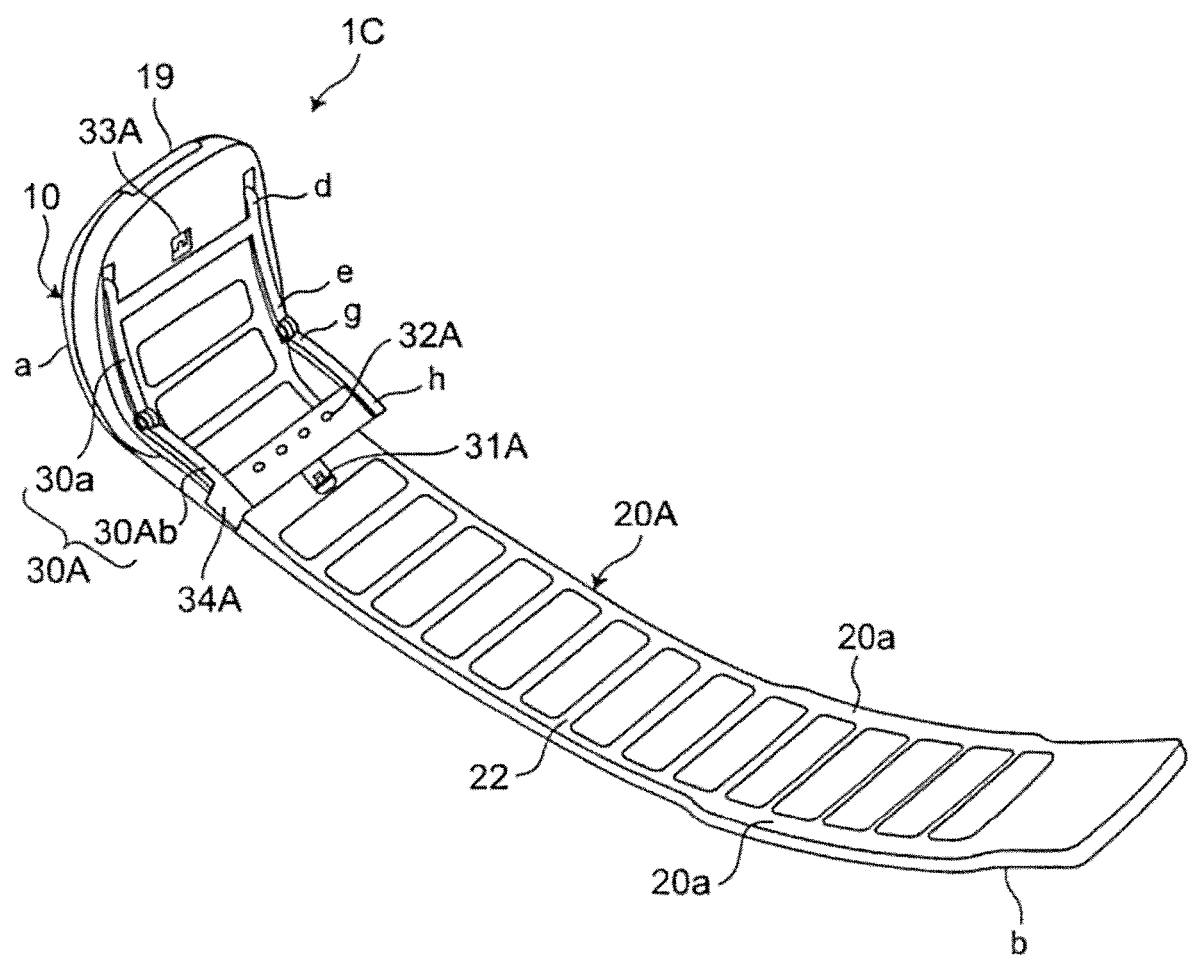
FIG. 15A is a bottom view of a bodily information measurement apparatus 1C according to Modified Example 1 of the second embodiment of the present invention.

FIG. 15A is a bottom view of a bodily information measurement apparatus 1C according to a modified example 1 of the second embodiment of the present invention. In comparison to the bodily information measurement apparatus 1A according to the second embodiment, the bodily information measurement apparatus 1C according to the present embodiment differs in that hook portions 34A are included instead of the hook portions 34. In comparison to the hook portions 34, the portions of the hook portions 34A that are locked by catching on the belt 20A are even larger. Stated in further detail, in the lengthwise direction of the belt, the hook portions 34 extend only to one side with respect to the first fixing elements (engaging portions 32A), but the hook portions 34A extend to both sides. With this configuration, it is possible to more reliably fix the second plate frame member 30Ab using the belt 20A.

Note that in the second embodiment and the modified examples thereof, one hook portion is formed on one side of the buckle, but the present invention is not limited to this. For example, two or more hook portions may be formed on one side of the buckle. With this configuration, it is possible to even more reliably fix the second plate frame member 30Ab using the belt 20A.

Modified Example 2 of Second Embodiment

Figure 16A:
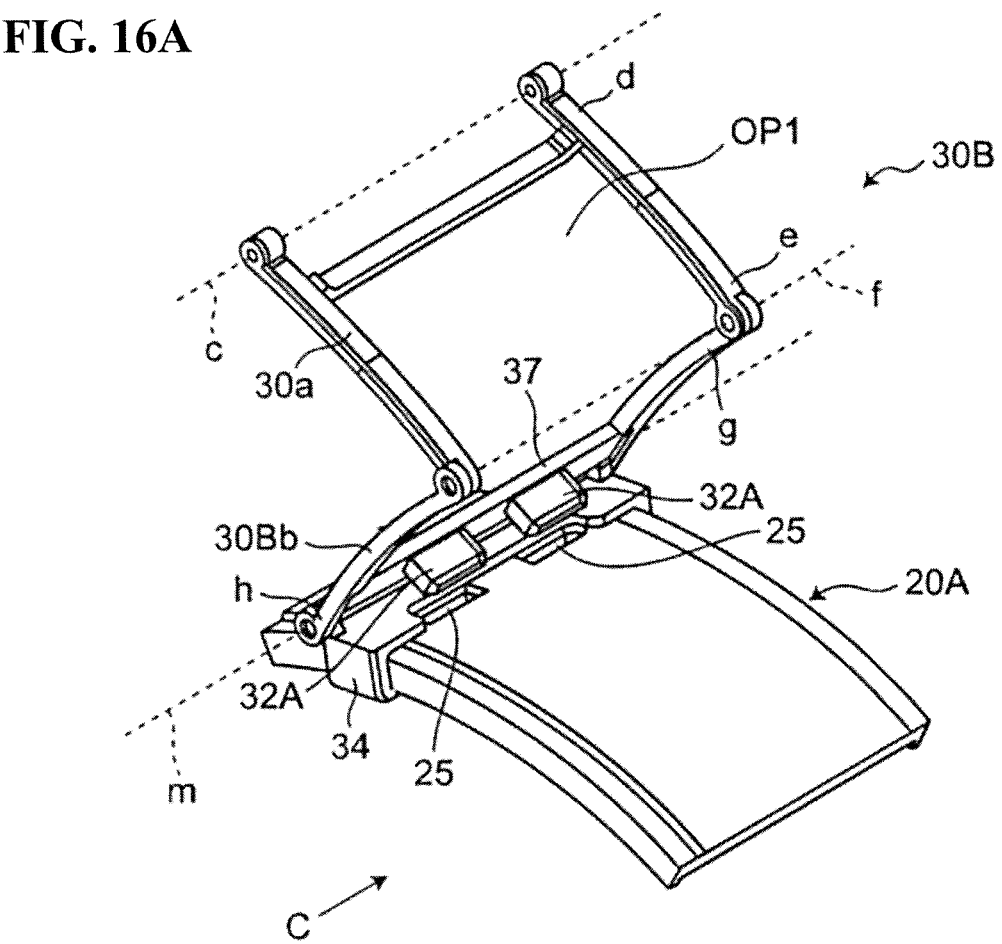
FIG. 16A is a perspective view showing a first state of the buckle 30B at a time when the buckle 30B according to Modified Example 2 of the second embodiment of the present invention is attached to the belt 20A.
Figure 16B:
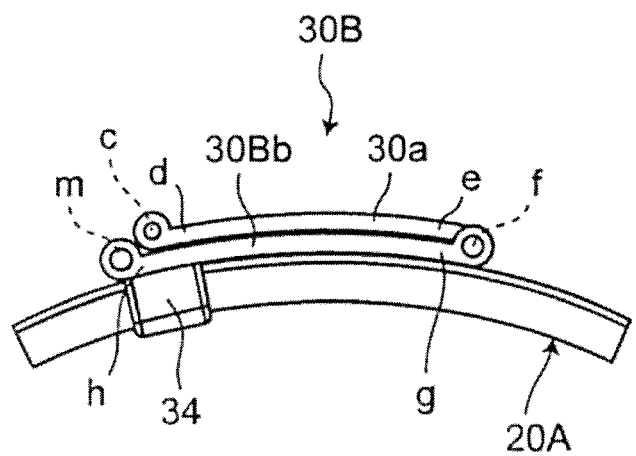
FIG. 16B is a side view showing a second state at a time when the buckle 30B shown in FIG. 16A is attached to the belt 20A.

FIG. 16A is a perspective view showing a first state of the buckle 30B at a time when the buckle 30B according to Modified Example 2 of the second embodiment of the present invention is attached to the belt 20A. FIG. 16B is a side view (a side view taken in the direction of arrow C in FIG. 16A) showing a second state at a time when the buckle 30B shown in FIG. 16A is attached to the belt 20A.

The buckle 30B shown in FIG. 16 differs in comparison to the buckle 30A according to the second embodiment in that a second plate frame member 30Bb is included instead of the second plate frame member 30Ab. In comparison to the second plate frame member 30Ab according to the second embodiment, the second plate frame member 30Bb differs in that the plate portion 37 having the first fixing elements (engaging portions 32A) that can rotate about an axis m that is parallel to an axis c is attached to the other end portion h of the second plate frame member 30Bb. The protruding engaging portions 32A (first fixing elements) are formed on the plate portion 37. The length of the loop of the belt 20A is set by engaging the engaging portions 32A with the recessed engaged portions 25 (second fixing elements) formed on the belt 20A.

With this configuration, the first fixing elements (engaging portions 32A) can rotate with respect to the belt 20A, and therefore the first fixing elements (engaging portions 32A) are easily engaged with the second fixing elements (engaged portions 25). Accordingly, the length of the loop of the belt 20A is variable and thus is easily set so as to exactly match the circumferential length of the wrist 90 serving as the measurement site.

Third Embodiment

Figure 14A:
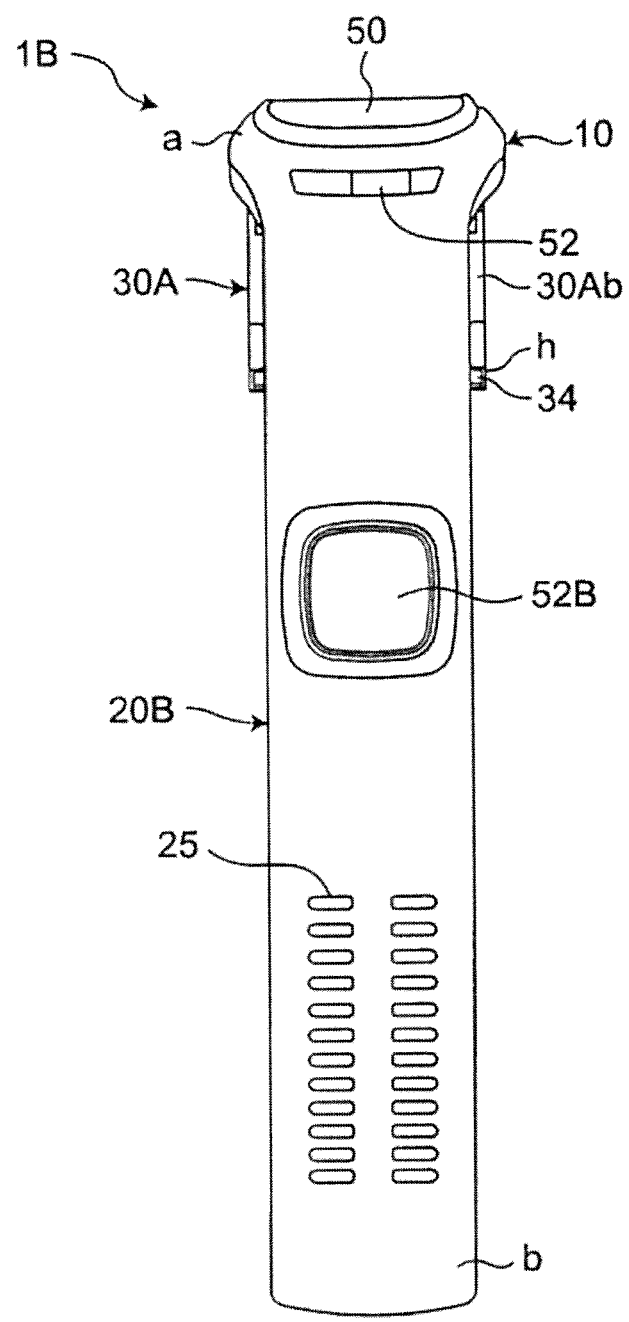
FIG. 14A is a top view showing an exterior of a bodily information measurement apparatus 1B according to a third embodiment of the present invention.
Figure 14B:
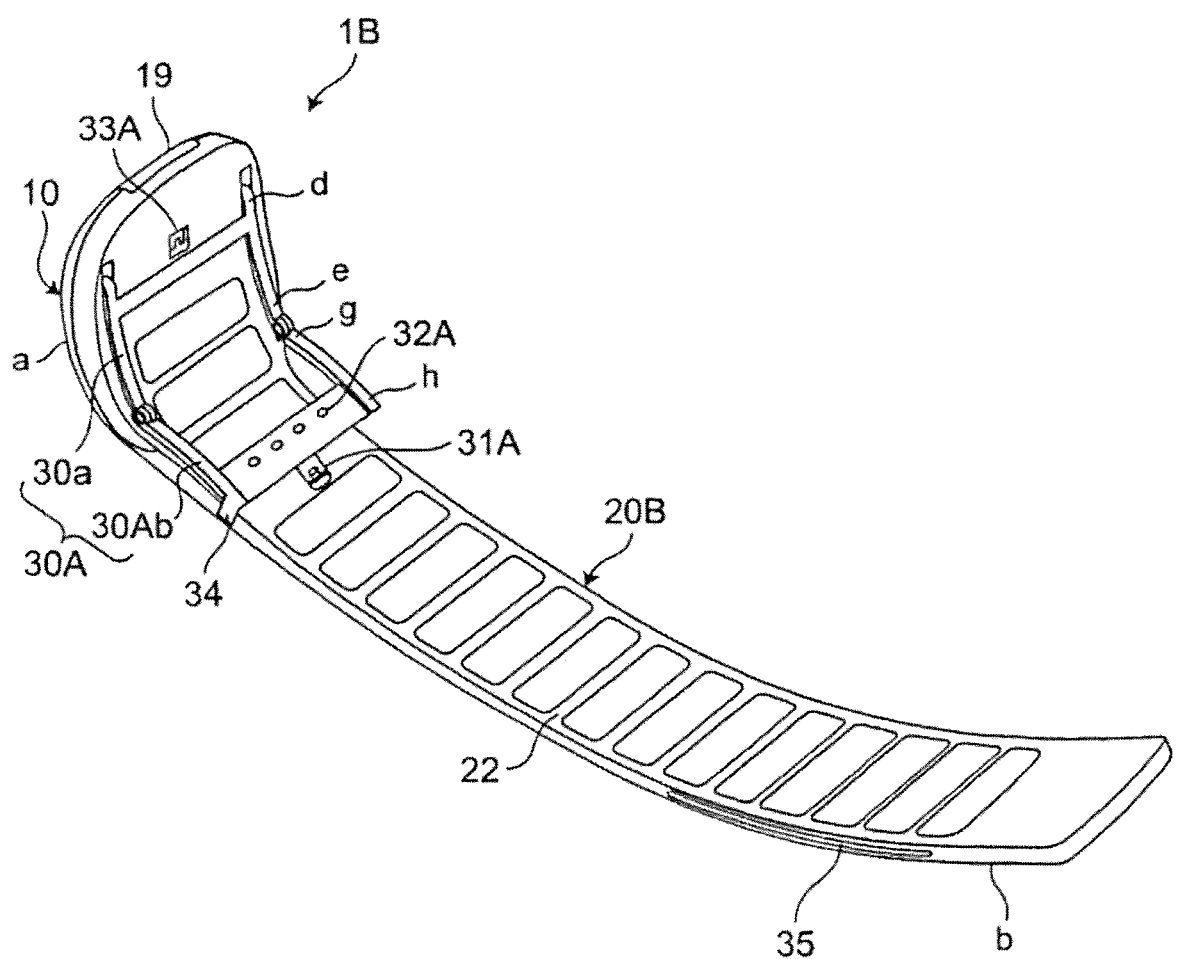
FIG. 14B is a bottom view of the bodily information measurement apparatus 1B in FIG. 14A.
Figure 14C:
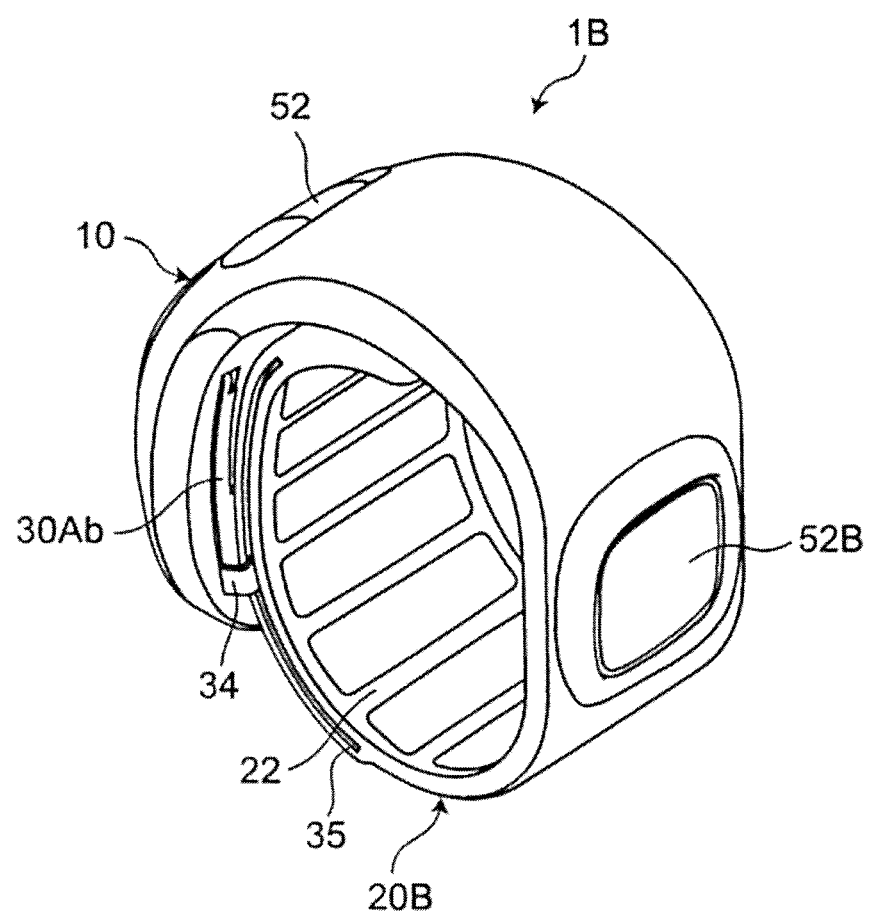
FIG. 14C is a perspective view showing a state at a time of attaching the bodily information measurement apparatus 1B in FIG. 14A by wrapping it around a measurement site.

FIG. 14A is a top view showing the exterior of a bodily information measurement apparatus 1B according to a third embodiment of the present invention. FIG. 14B is a bottom view of the bodily information measurement apparatus 1B shown in FIG. 14A, and FIG. 14C is a perspective view showing a state at a time of attaching the bodily information measurement apparatus 1B shown in FIG. 14A by wrapping it around a measurement site.

In comparison to the bodily information measurement apparatus 1A according to the second embodiment, the bodily information measurement apparatus 1B according to the present embodiment differs in that a belt 20B is included instead of the belt 20A. In comparison to the belt 20A according to the second embodiment, the belt 20B differs in that cut-out portions 35 that are locked due to the leading end portions of the hook portions 34 being inserted are provided instead of the wide portions 20a at a portion of the leading end portion b of the belt 20B that is formed so as to be thick. With this configuration, as shown in FIG. 14C, the hook portions 34 grip the belt 20B in the cut-out portions 35 of the belt 20B. Accordingly, the second plate frame member 30Ab can be reliably fixed to the belt 20B.

Modified Example of Third Embodiment

Figure 15B:
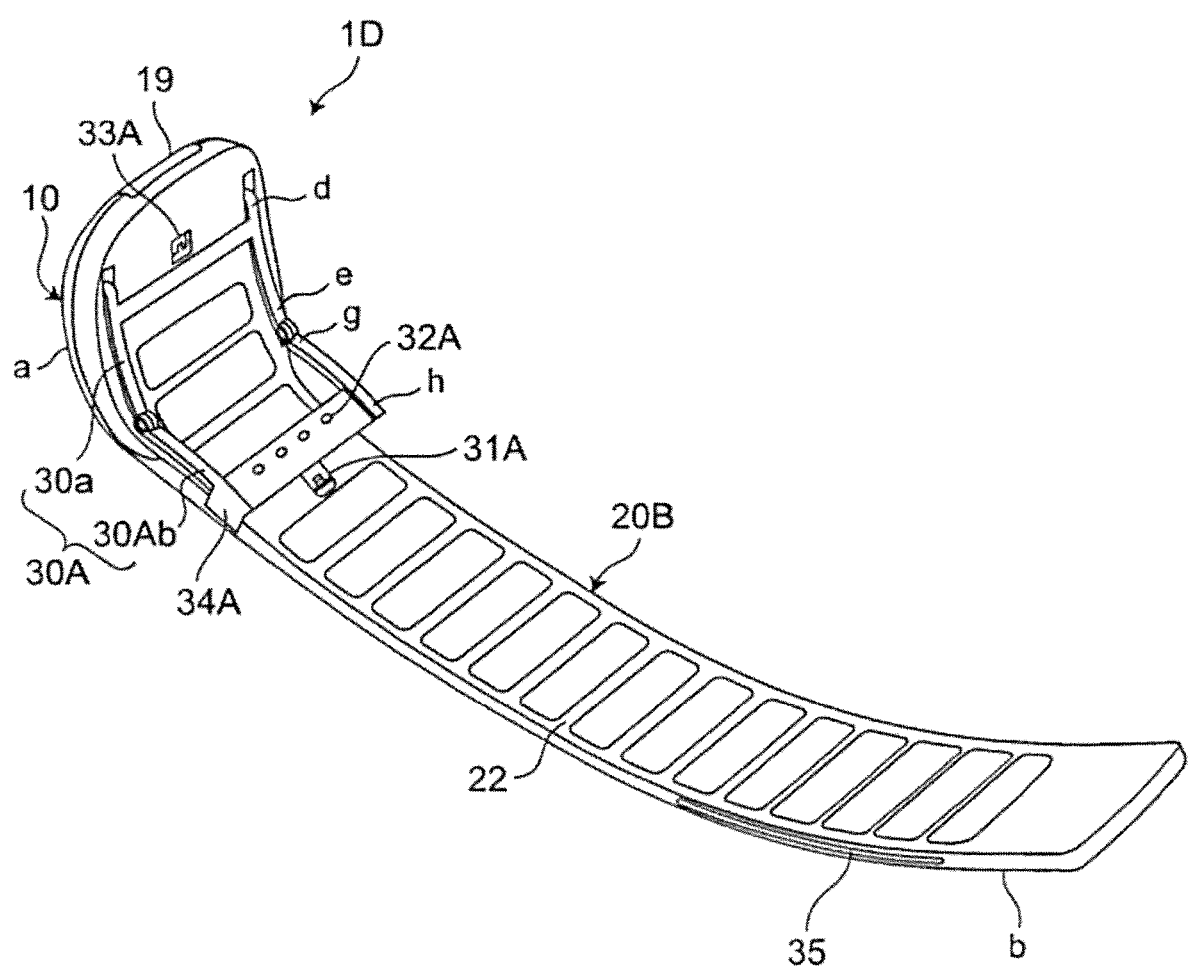
FIG. 15B is a bottom view of a bodily information measurement apparatus 1D according to a modified example of the third embodiment of the present invention.

FIG. 15B is a bottom view of a bodily information measurement apparatus 1D according to a modified example of the third embodiment of the present invention. In comparison to the bodily information measurement apparatus 1B according to the third embodiment, the bodily information measurement apparatus 1D according to the present modified example differs in that hook portions 34A are included instead of the hook portions 34. In comparison to the hook portions 34, the portions of the hook portions 34A that are locked by catching on the belt 20B are even larger. Stated in further detail, in the lengthwise direction of the belt, the hook portions 34 extend to only one side with respect to the first fixing elements (engaging portions 32A), but the hook portions 34A extend to both sides. With this configuration, on the leading ends of the hook portions 34A, the portions that are inserted into the cut-out portions 35 of the belt 20B are even larger. Accordingly, the second plate frame member 30Ab can be reliably fixed by the belt 20B.

Note that in the third embodiment and the modified example thereof, one hook portion is formed on one side of the buckle, but the present invention is not limited to this. For example, two or more hook portions may be formed on one side of the buckle. With this configuration, it is possible to more reliably fix the second plate frame member 30Ab using the belt 20B.

Fourth Embodiment

Figure 18A:
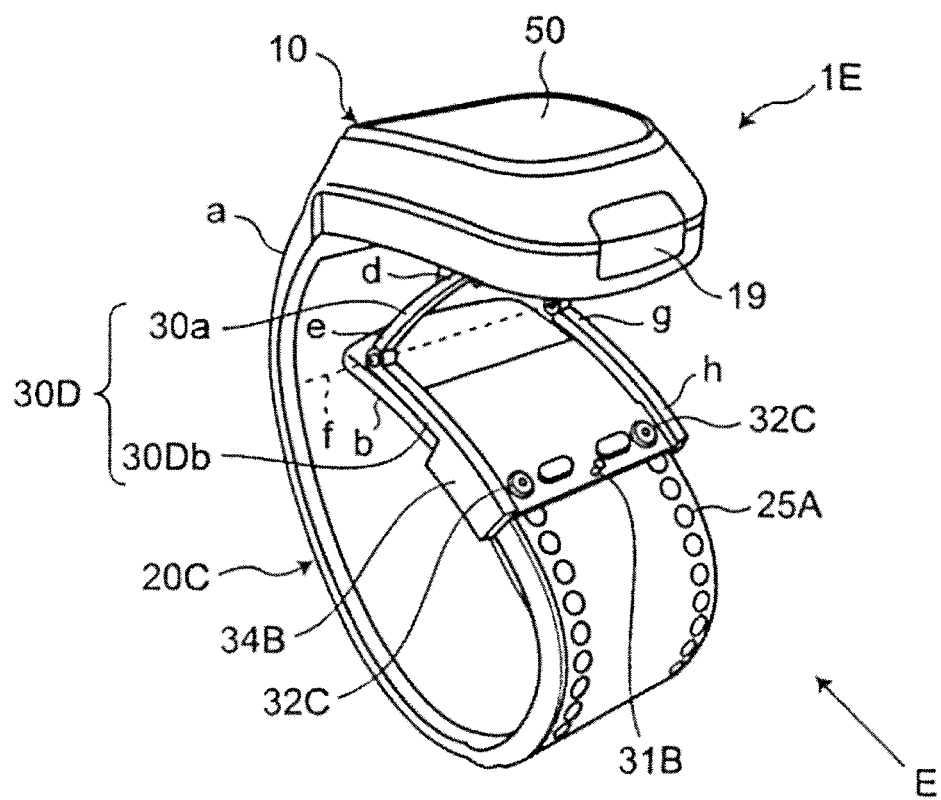
FIG. 18A is a perspective view at a time of attaching a bodily information measurement apparatus 1E according to a fourth embodiment of the present invention by wrapping it around a measurement site.
Figure 18B:
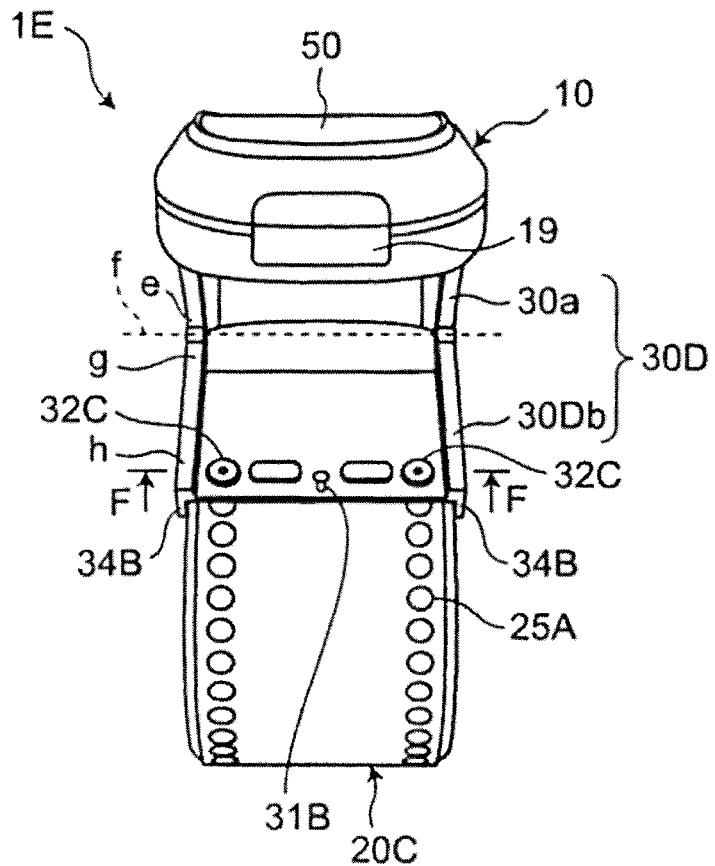
FIG. 18B is a side view of FIG. 18A.
Figure 18C:
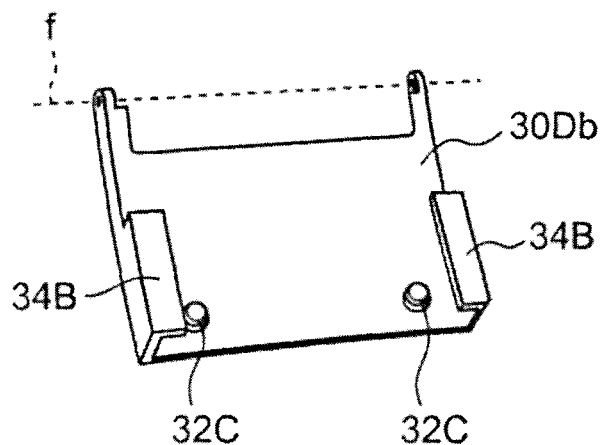
FIG. 18C is a plan view of a first plate-shaped member 30Db shown in FIG. 18A.
Figure 18D:
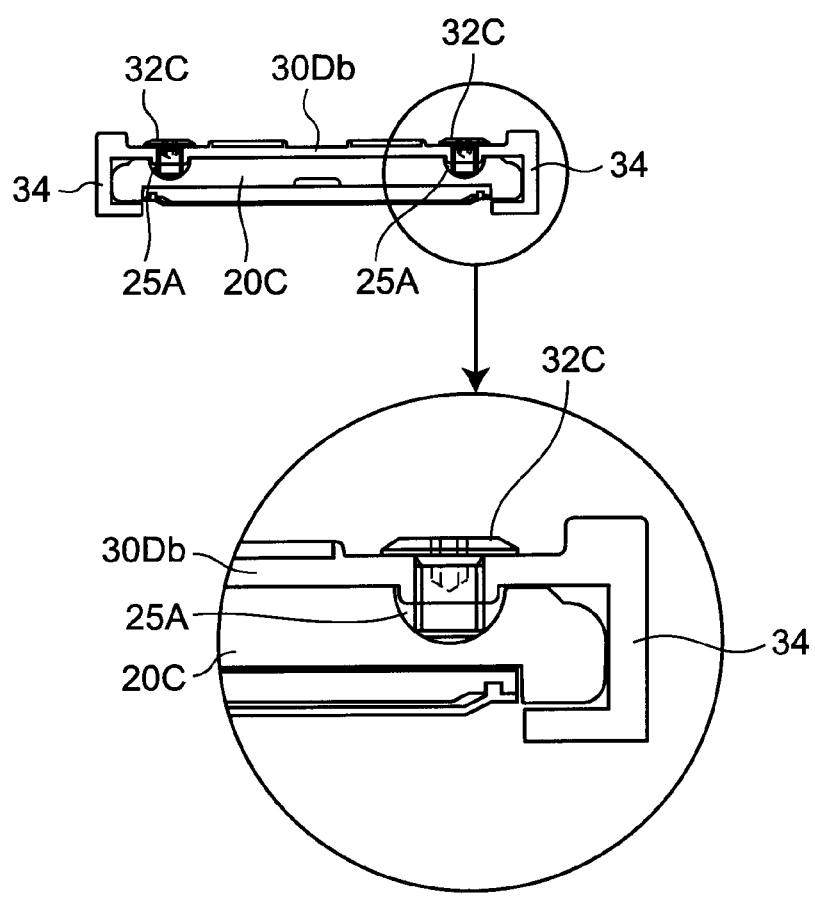
FIG. 18D is a lateral cross-sectional view taken along line F-F in FIG. 18B.

FIG. 18A is a perspective view at a time when a bodily information measurement apparatus 1E according to a fourth embodiment of the present invention is attached to a measurement site by being wrapped around it. FIG. 18B is a side view of FIG. 18A (a side view taken in the direction of arrow E in FIG. 18A). FIG. 18C is a plan view of the first plate frame member 30Db shown in FIG. 18A. Here, a surface that comes into contact with the belt 20C when the bodily information measurement apparatus 1E is attached by being wrapped around the measurement site is shown. FIG. 18D is a lateral cross-sectional view taken along line F-F in FIG. 18B. Here, the end side of the arrow indicates an enlarged view of the drawing on the origin side of the arrow.

As shown in FIGS. 18A and 18B, in comparison to the bodily information measurement apparatus 1 shown in FIG. 2, the bodily information measurement apparatus 1E differs in that a buckle 30D is included instead of the buckle 30 and a belt 20C is included instead of the belt 20.

As shown in FIGS. 18A and 18B, in comparison to the belt 20, the belt 20C differs in that engaged portions 25A are included instead of the engaged portions 25 as the second fixing elements. As shown in FIGS. 18A and 18B, multiple (in this example, two) engaged portions 25A with an approximately hemispherical recessed shape are formed in alignment in the width direction of the belt 20C. Accordingly, even if the belt 20C twists slightly, the engagement between later-described fastening screws 32C and the engaged portions 25A is not likely to come off.

As shown in FIGS. 18A and 18B, in comparison to the buckle 30, the buckle 30D differs in that a first plate-shaped member 30Db is included instead of the second plate frame member 30b. As shown in FIGS. 18A to 18D, hook-shaped hook portions 34B that are formed so as to protrude are formed on the other end portion h of the first plate-shaped member 30Db. The hook portions 34B are locked by catching on the two end portions in the width direction of the belt 20C. Accordingly, the first plate-shaped member 30Db can be reliably fixed to the belt 20C.

As can be understood from FIG. 18D, screw holes through which the fastening screws 32C, which are first fixing elements, penetrate are formed in the first plate-shaped member 30Db, and the leading end portions of the fastening screws 32C are received in the recessed engaged portions 25A (second fixing elements) via the screw holes. Accordingly, the first plate-shaped member 30Db is fixed to the belt 20C.

Also, as shown in FIGS. 18A and 18B, the engaged portions (not shown), which have recessed shapes, are included on the inner surface side of the base end portion a of the belt 20C, the engaging portions 31B that engage with the engaged portions are included on the first plate-shaped member 30Db, and thereby the lock mechanism is formed. With the lock mechanism, it is possible to lock the inner surface side of the base end portion a of the belt 20C or the one end portion d of the first plate frame member 30a together with the other end portion h of the first plate-shaped member 30Db. Accordingly, when the main body 10, the first plate frame member 30a, and the first plate-shaped member 30Db of the buckle 30D are folded in on each other, the inner surface of the main body 10, the first plate frame member 30a, and the first plate-shaped member 30Db of the buckle 30D are fixed so as to overlap.

Modified Example 1 of Fourth Embodiment

Figure 19A:
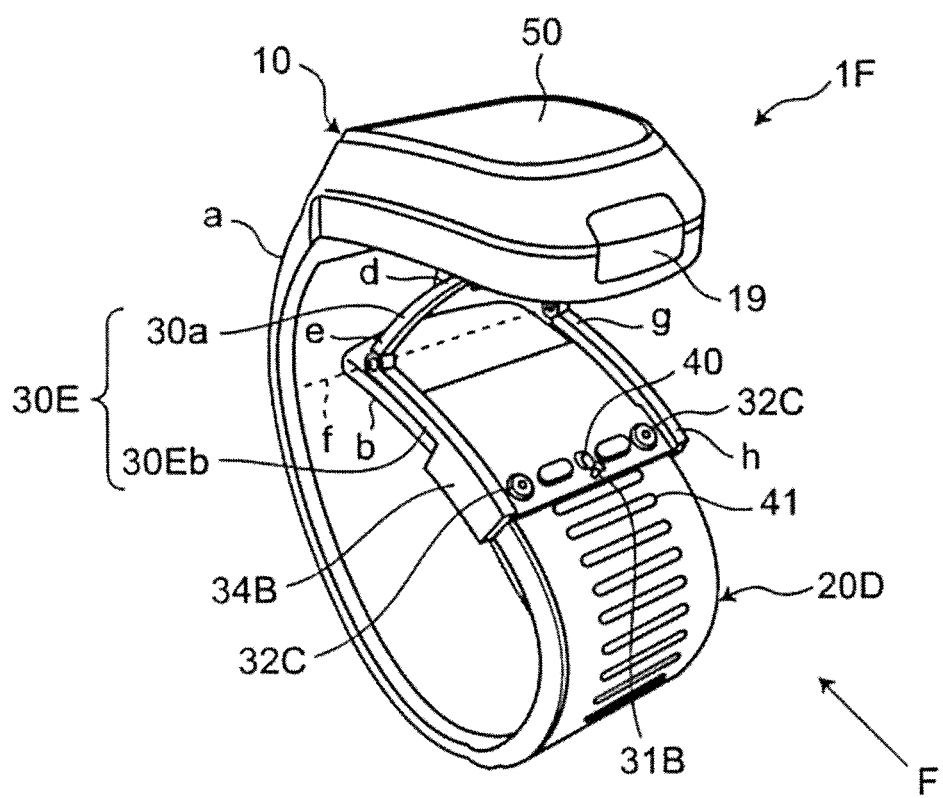
FIG. 19A is a perspective view taken when the bodily information measurement apparatus 1F according to Modified Example 1 of the fourth embodiment of the present invention is attached to the measurement site by being wrapped around it.
Figure 19B:
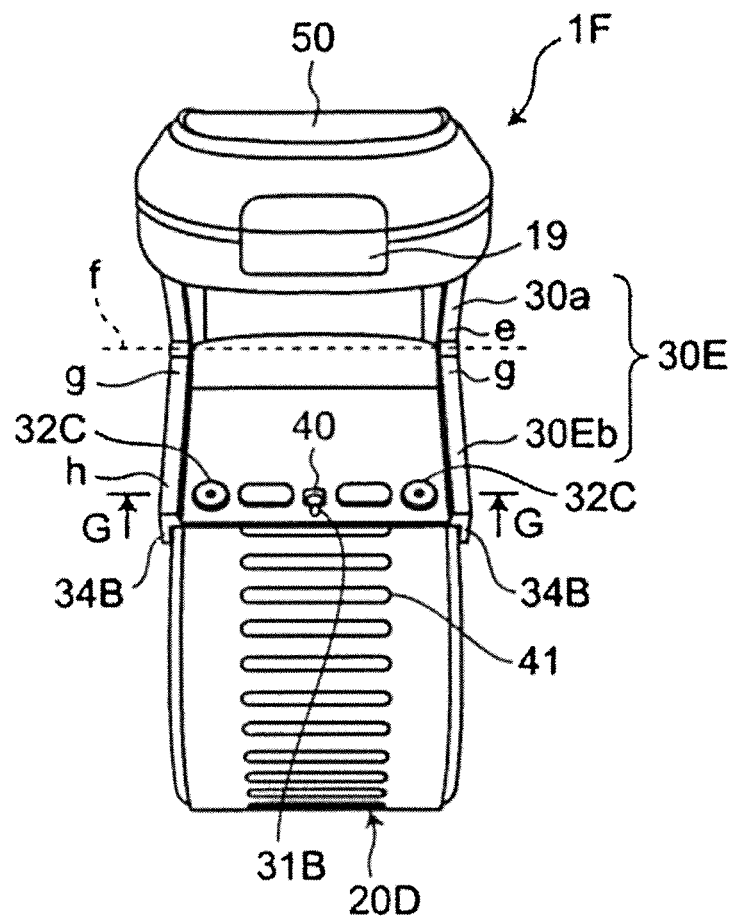
FIG. 19B is a side view of FIG. 19A.
Figure 19C:
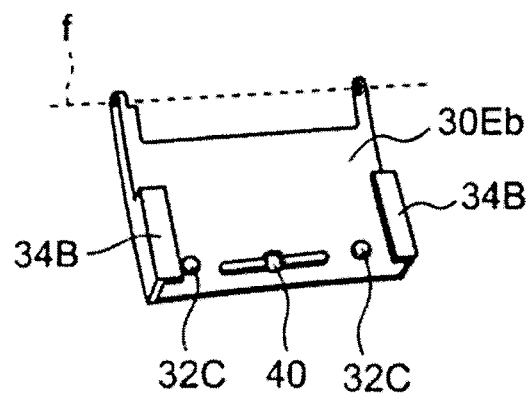
FIG. 19C is a plan view of a first plate-shaped member 30Eb shown in FIG. 19A.
Figure 19D:
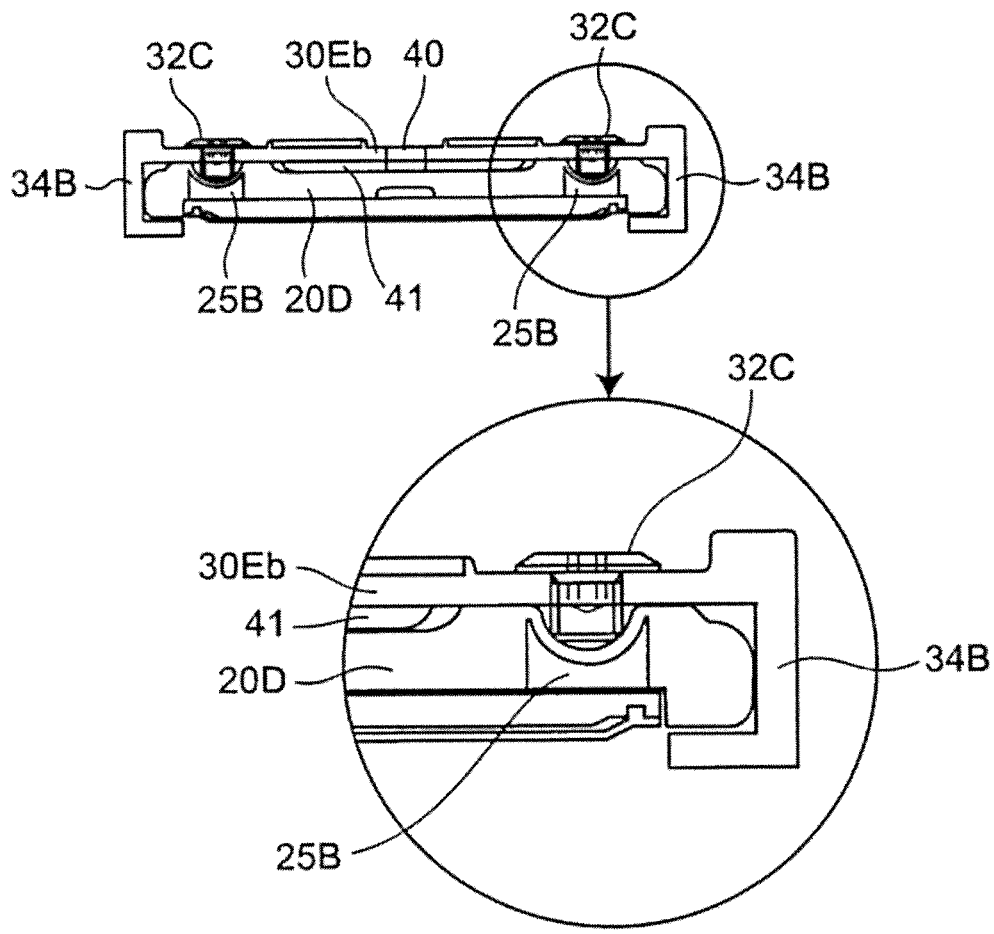
FIG. 19D is a lateral cross-sectional view taken along line G-G in FIG. 19B.
Figure 19E:
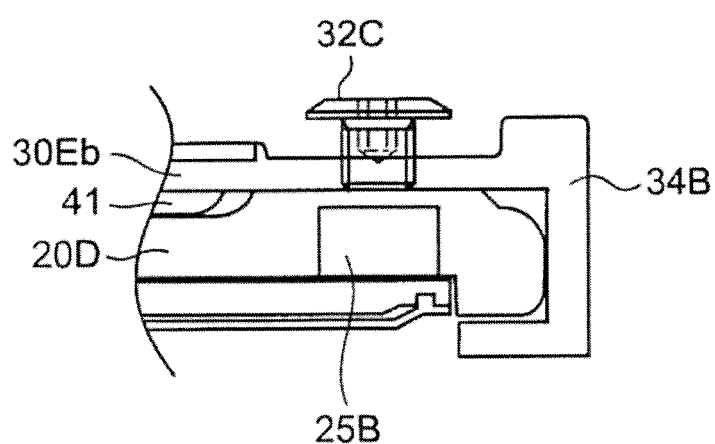
FIG. 19E is a lateral cross-sectional view for illustrating a state prior to performing fastening using a fastening screw 32C shown in FIG. 19A.

FIG. 19A is a perspective view at a time when the bodily information measurement apparatus 1F according to Modified Example 1 of the fourth embodiment of the present invention is attached to the measurement site by being wrapped around it. FIG. 19B is a side view of FIG. 19A (a side view taken in the direction of arrow F in FIG. 19A). FIG. 19C is a plan view of a first plate-shaped member 30Eb shown in FIG. 19A. Here, a surface that comes into contact with the belt 20D when the bodily information measurement apparatus 1E is attached by being wrapped around the measurement site is shown. FIG. 19D is a lateral cross-sectional view taken along line G-G in FIG. 19B. Here, the end side of the arrow indicates an enlarged view of the drawing on the origin side of the arrow. FIG. 19E is a lateral cross-sectional view for illustrating a state prior to performing fastening using fastening screws 32C shown in FIG. 19A.

In comparison to the bodily information measurement apparatus 1E shown in FIG. 18A, the bodily information measurement apparatus 1F shown in FIG. 19A differs in that a buckle 30E is included instead of the buckle 30D and a belt 20D is included instead of the belt 20C.

As shown in FIGS. 19A and 19B, in comparison to the buckle 30D according to the fourth embodiment, the buckle 30E according to the present modified example differs in that a first plate-shaped member 30Eb is included instead of the first plate-shaped member 30Db. As shown in FIGS. 19A to 19D, in comparison to the first plate-shaped member 30Db, the first plate-shaped member 30Eb differs in that a cylindrical opening portion 40 that penetrates through the first plate-shaped member 30Eb is included at the approximately central position between the fastening screws 32C.

As shown in FIGS. 19A and 19B, in comparison to the belt 20C according to the fourth embodiment, the belt 20D according to the present modified example differs in that cavity portions 25B are included instead of the recessed engaged portions 25A and recessed portions 41 that extend in the width direction are included between the cavity portions 25B. The recessed portions 41 serve as markers for when searching for the positions of the cavity portions 25B, and the user specifies the locations of the cavity portions 25B while viewing the recessed portions 41 through the opening portion 40 and performs position alignment for when fastening using the fastening screws 32C.

FIG. 19E shows a state immediately prior to when the fastening screws 32C are received in the cavity portions 25B. If the fastening screws 32C shown in FIG. 19E are rotated and the fastening screws 32C are rotated via the screw holes in the first plate-shaped member 30Eb, as shown in FIG. 19D, the bottom portions of the fastening screws 32C reach the belt 20D between the cavity portions 25B and the screw holes. Furthermore, when the fastening screws 32C are rotated, the belt 20D warps, the bottom portions of the fastening screws 32C advance to the cavity portions 25B, and the fastening screws 32C are received in the cavity portions 25B. Accordingly, the first plate-shaped member 30Eb is fixed to the belt 20D.

Modified Example 2 of Fourth Embodiment

Figure 20A:
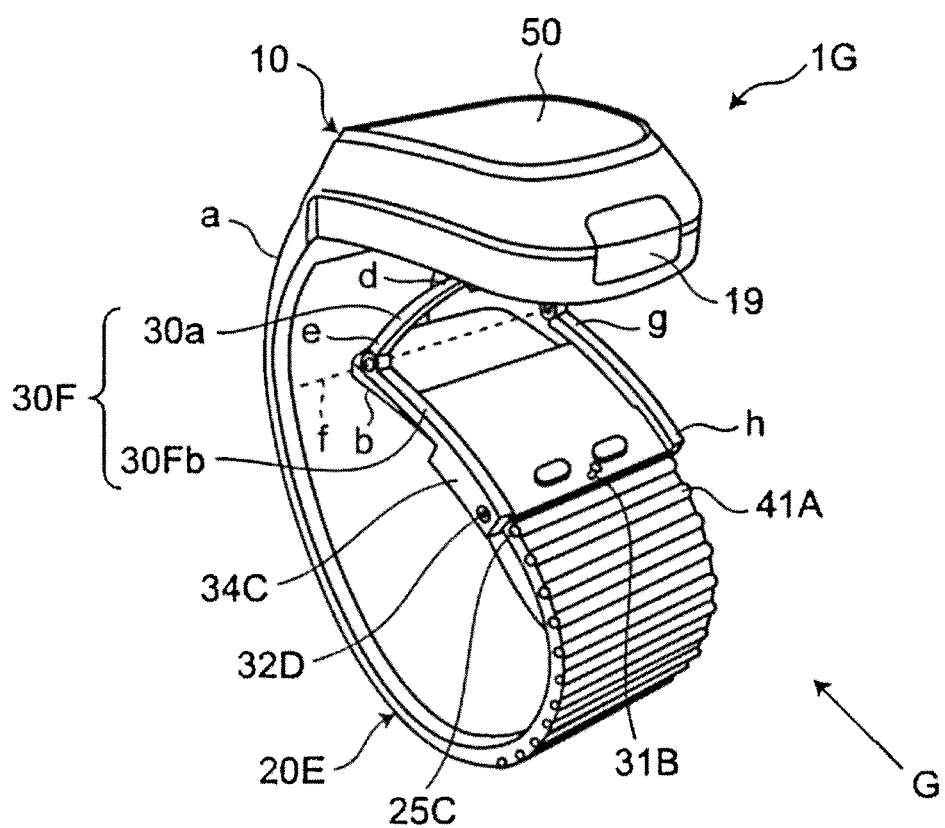
FIG. 20A is a perspective view taken when a bodily information measurement apparatus 1G according to Modified Example 2 of the fourth embodiment of the present invention is attached to the measurement site by being wrapped around it.
Figure 20B:
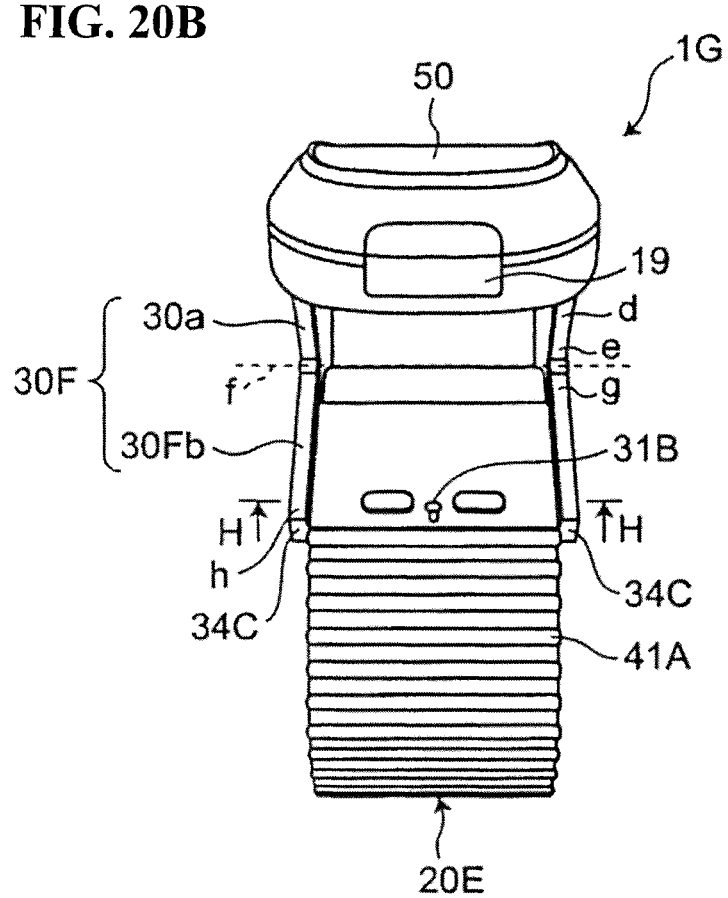
FIG. 20B is a side view of FIG. 20A.
Figure 20C:
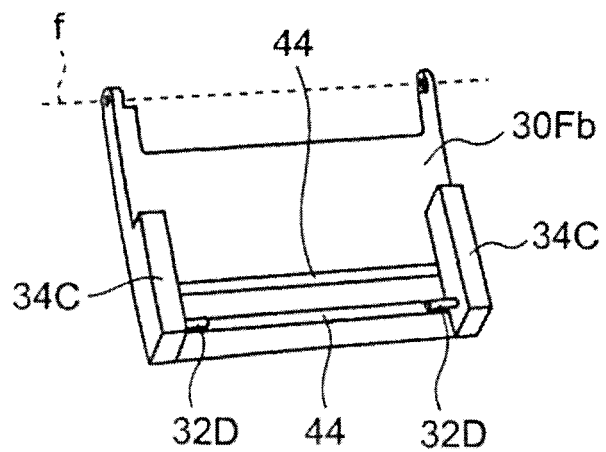
FIG. 20C is a plan view of a first plate-shaped member 30Fb shown in FIG. 20A.
Figure 20D:
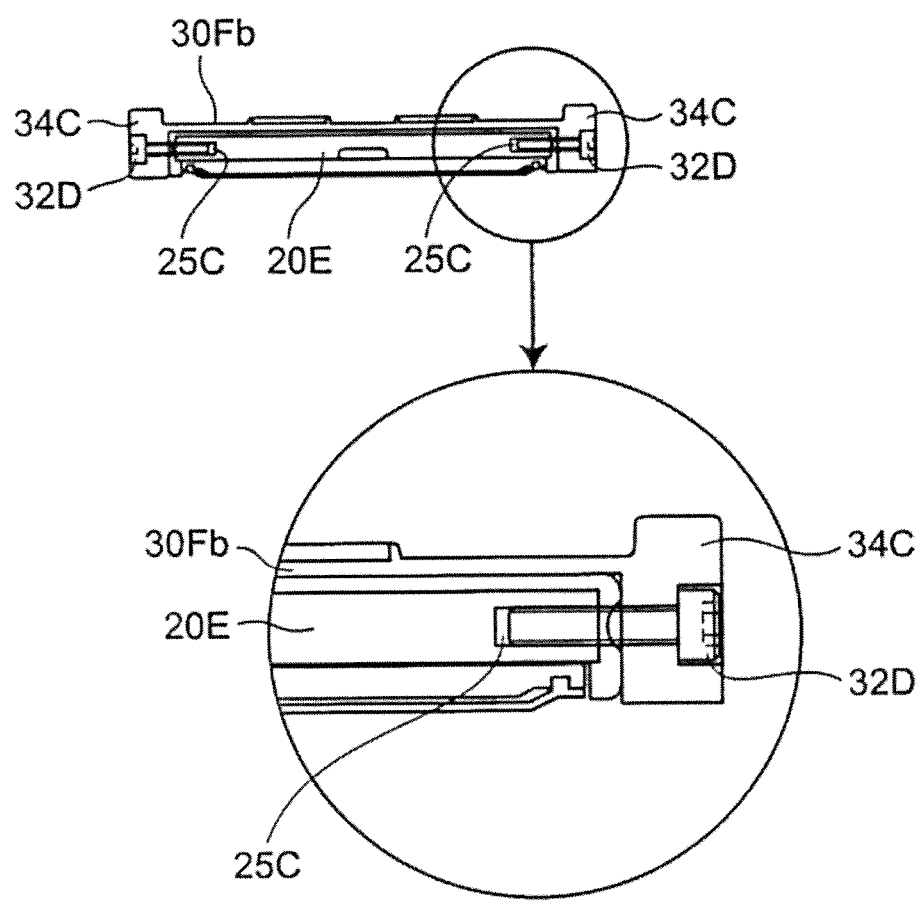
FIG. 20D is a lateral cross-sectional view taken at a time of cutting along line H-H in FIG. 20B.

FIG. 20A is a perspective view taken when a bodily information measurement apparatus 1G according to Modified Example 2 of the fourth embodiment of the present invention is attached to the measurement site by being wrapped around it. FIG. 20B is a side view of FIG. 20A (a side view taken in the direction of arrow G in FIG. 20A). FIG. 20C is a plan view of a first plate-shaped member 30Fb shown in FIG. 20A. Here, a surface that comes into contact with the belt 20E when the bodily information measurement apparatus 1G is attached to the measurement site by being wrapped around it is shown. FIG. 20D is a lateral cross-sectional view taken along line H-H in FIG. 20B. Here, a state at a time of performing fixing by fastening using the fastening screws 32D is shown. Note that the end side of the arrow indicates an enlarged view of the drawing drawn on the origin side of the arrow.

In comparison to the bodily information measurement apparatus 1E shown in FIG. 18A, the bodily information measurement apparatus 1G shown in FIG. 20A differs in that a buckle 30F is included instead of the buckle 30D and a belt 20E is included instead of the belt 20C.

As shown in FIGS. 20A and 20B, in comparison to the buckle 30D according to the fourth embodiment, the buckle 30F according to the present modified example differs in that a first plate-shaped member 30Fb is included instead of the first plate-shaped member 30Db. As shown in FIGS. 20A to 20D, in comparison to the first plate-shaped member 30Db, the first plate-shaped member 30Fb differs in that a fastening screw 32D is included instead of the fastening screw 32C, a recessed portion 44 that fits together with a later-described protruding portion 41A that is formed so as to protrude in the width direction and serves as a marker is included, and a hook portion 34C is included instead of the hook portion 34. Here, screw holes through which the fastening screws 32D pass are provided on the surface on which the hook portions 34C and the belt 20E come into contact when the first plate-shaped member 30Fb is fixed to the belt 20E.

As shown in FIGS. 20A and 20D, in comparison to the belt 20C according to the fourth embodiment, the belt 20E according to the present modified example differs in that cavity portions 25C are included instead of the recessed engaged portions 25A, and protruding portions 41A that extend in the width direction are included between the cavity portions 25C. The protruding portions 41A serve as markers for when searching for the position of the cavity portions 25C. Two adjacent protruding portions 41A and two adjacent recessed portions 44 of the first plate-shaped member 30Fb fit together, whereby the first plate-shaped member 30Fb is fixed to the belt 20.

FIG. 20D shows a state after the fastening screws 32D have been inserted into the cavity portions 25C. When the fastening screws 32D are rotated via the screw holes in the first plate-shaped member 30Fb, as shown in FIG. 20D, the bottom portions of the fastening screws 32D reach the belt 20E between the cavity portions 25C and the screw holes. Furthermore, when the fastening screws 32D are rotated, the belt 20E warps, the bottom portions of the fastening screws 32D penetrate through the belt 20E and advance to the cavity portions 25C, and the fastening screws 32D are received in the cavity portions 25C. Accordingly, the first plate-shaped member 30Fb is fixed to the belt 20E.

Modified Example 3 of Fourth Embodiment

Figure 21A:
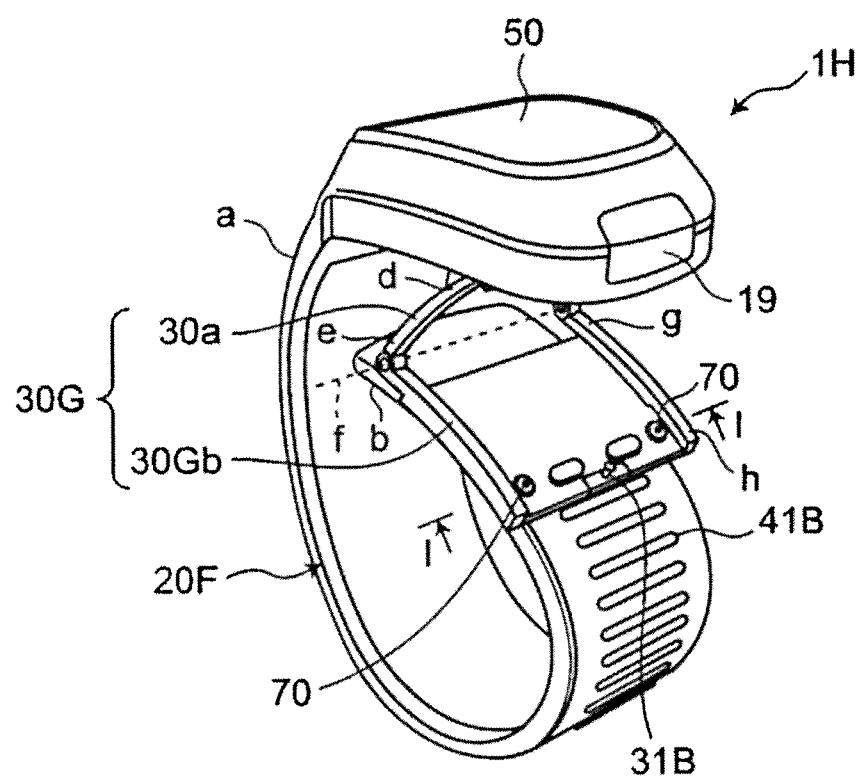
FIG. 21A is a perspective view taken when a bodily information measurement apparatus 1H according to Modified Example 3 of the fourth embodiment of the present invention is attached to the measurement site by being wrapped around it.
Figure 21B:
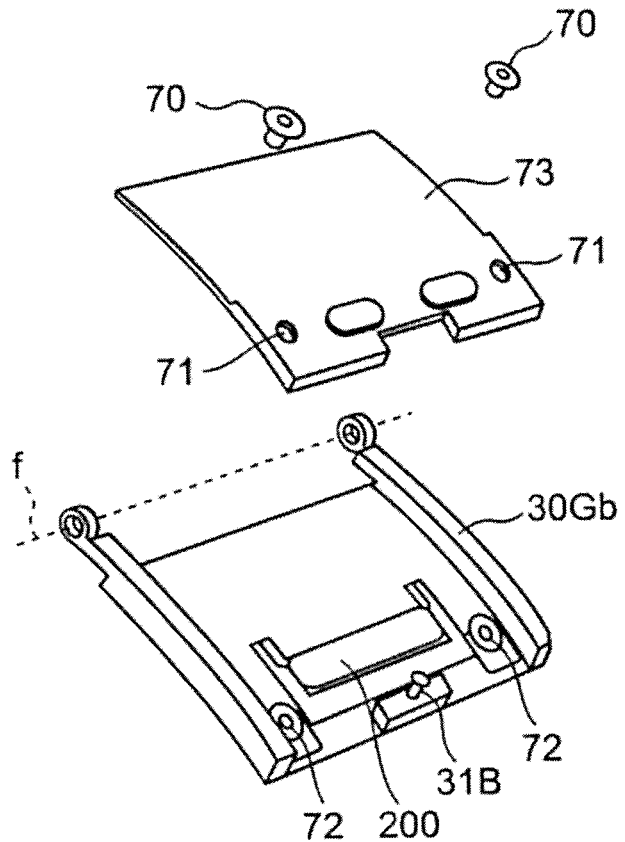
FIG. 21B is an exploded perspective view of a buckle 30G in FIG. 21A.
Figure 21C:
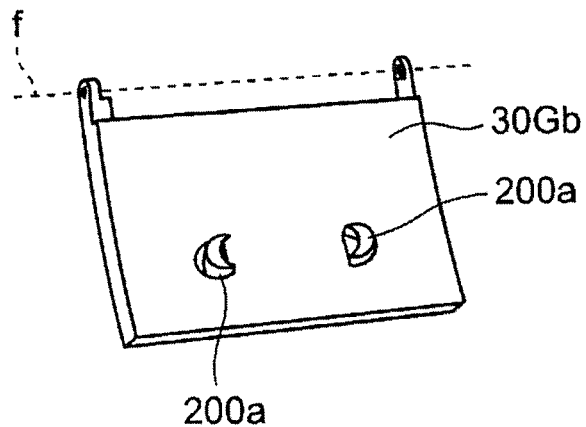
FIG. 21C is a plan view of the buckle 30G in FIG. 21A.
Figure 21D:
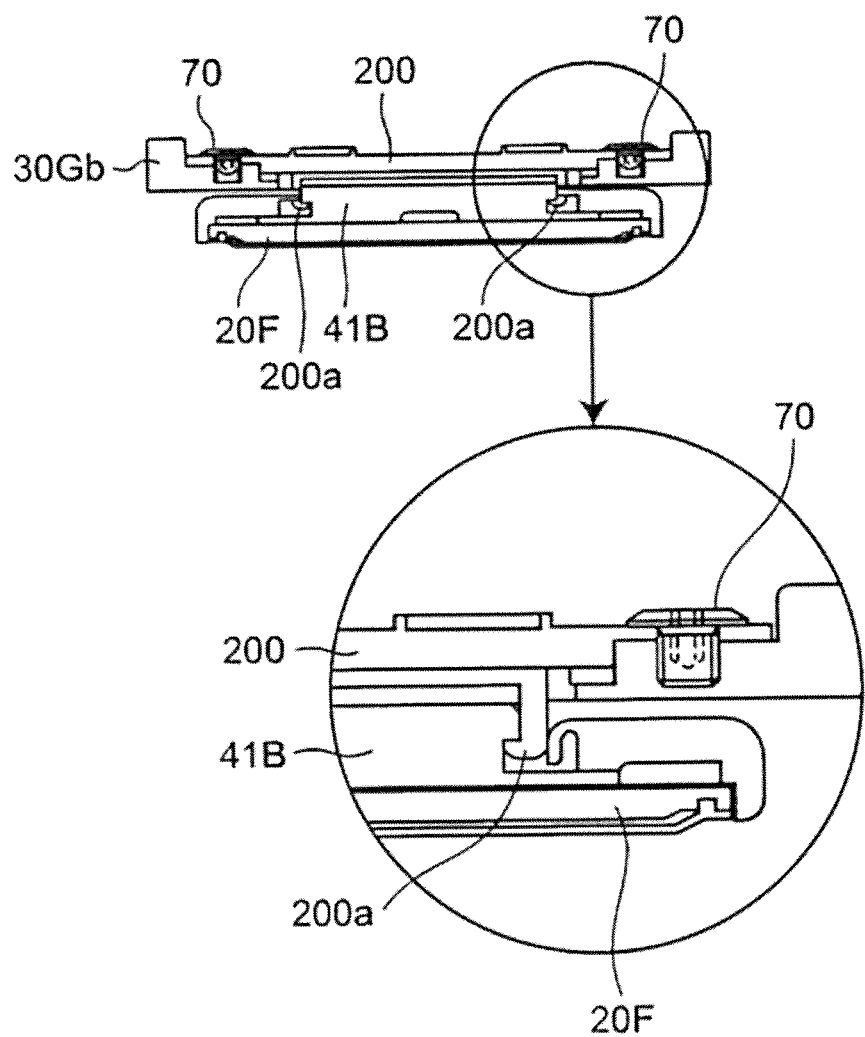
FIG. 21D is a lateral cross-sectional view taken along line I-I in FIG. 21A.

FIG. 21A is a perspective view taken when a bodily information measurement apparatus 1H according to Modified Example 3 of the fourth embodiment of the present invention is attached to the measurement site by being wrapped around it. FIG. 21B is an exploded perspective view of the buckle 30G shown in FIG. 21A. FIG. 21C is a plan view of the buckle 30G shown in FIG. 21A. Here, a surface that comes into contact with the belt 20F when the bodily information measurement apparatus 1H is attached to the measurement site by being wrapped around it is shown. FIG. 21D is a lateral cross-sectional view taken along line I-I in FIG. 21A. Here, a state at a time of performing fixing by interposing the protruding portions 41B that extend in the width direction from both sides using a latch mechanism 200 is shown. Note that the end side of the arrow indicates an enlarged view of the drawing drawn on the origin side of the arrow.

In comparison to the bodily information measurement apparatus 1E shown in FIG. 18A, the bodily information measurement apparatus 1H shown in FIG. 21A differs in that the buckle 30G is included instead of the buckle 30D and a belt 20F is included instead of the belt 20C.

As shown in FIG. 21A, in comparison to the buckle 30D according to the fourth embodiment, the buckle 30G according to the present modified example differs in that a first plate-shaped member 30Gb is included instead of the first plate-shaped member 30Db. As shown in FIGS. 21A to 21D, in comparison to the first plate-shaped member 30Db, the first plate-shaped member 30Gb differs in that the hook portions 34B are removed, a latch mechanism 200 is included instead of the fastening screws 32C, and a cover member 73 that covers the latch mechanism 200 is further included. The cover member 73 has an approximate plate shape so as to overlap in the thickness direction with the first plate-shaped member 30Gb.

As shown in FIG. 21A, in comparison to the belt 20C according to the fourth embodiment, the belt 20F according to the present modified example differs in that protruding portions 41B that extend in the width direction are included instead of the recessed engaged portions 25A.

As shown in FIG. 21B, the cover member 73 is installed so as to overlap with the first plate-shaped member 30Gb using the screws 70. Specifically, first, the cover member 73 is installed on the first plate-shaped member 30Gb such that the screw holes 71 formed on the cover member 73 and the screw holes 72 formed on the first plate-shaped member 30Gb overlap. Next, when the screws 70 are inserted into the screw holes 71 and 72 and the screws 70 are fastened, the screws 70 are fixed by the screw holes 72. In this way, the cover member 73 is attached to the first plate-shaped member 30 Gb.

As shown in FIG. 21C, the latch mechanism 200 includes latch arms 200a between which an object can be interposed due to the interval in the width direction, which is parallel to the axis f, being changed and a spring (not shown) that changes the interval between the latch arms 200a. The latch mechanism 200 controls the spring such that when one latch arm 200a is moved outward, the other latch arm 200a is moved outward simultaneously. In this way, the interval between the latch arms 200a widens. Furthermore, the latch mechanism 200 controls the spring such that if none of the latch arms 200a is moved, the interval between the latch arms 200a becomes slightly smaller than the length in the width direction of the protruding portions 41B. In this way, the latch mechanism 200 can grip a protruding portion 41B at both ends by controlling the spring.

FIG. 21D shows a state at a time when a protruding portion 41B formed on the belt 20F is fixed by being gripped at both ends in the width direction by the latch arms 200a of the latch mechanism 200. When the protruding portion 41B is gripped by the latch mechanism 200, first, one latch arm 200a is moved outward by being caught on one end of the protruding portion 41B. Upon doing so, the other latch arm 200a also moves outward, the interval between the latch arms 200a widens and becomes larger than the length in the width direction of the protruding portion 41B, and therefore the protruding portion 41B can be gripped at both ends between the latch arms 200a. In this way, the buckle 30G can be fixed to the belt 20F.

Modified Example 4 of Fourth Embodiment

Figure 22A:
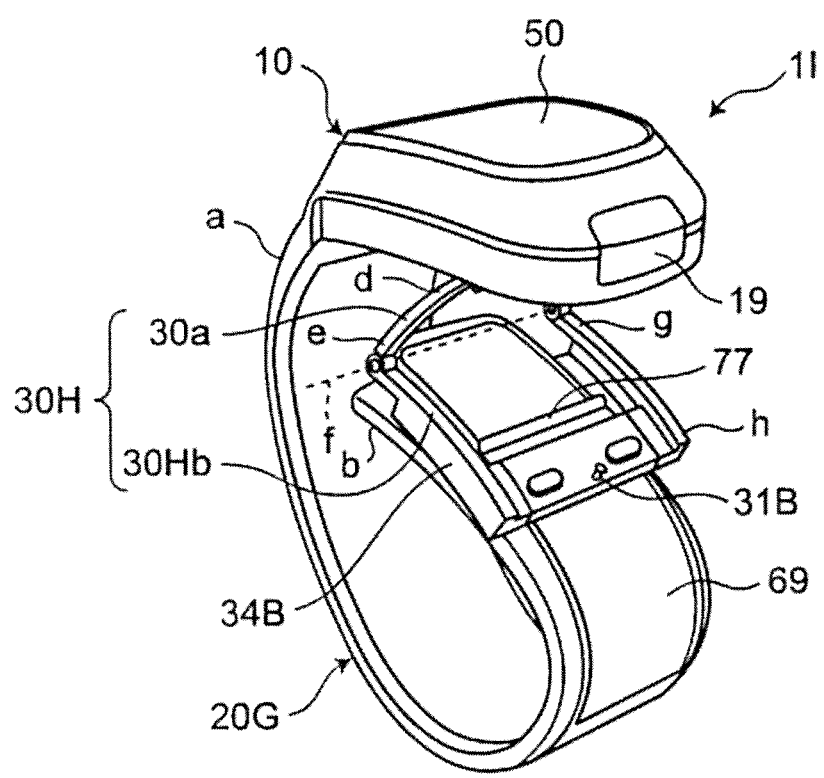
FIG. 22A is a perspective view taken when a bodily information measurement apparatus 1I according to Modified Example 4 of the fourth embodiment of the present invention is attached to the measurement site by being wrapped around it.
Figure 22B:
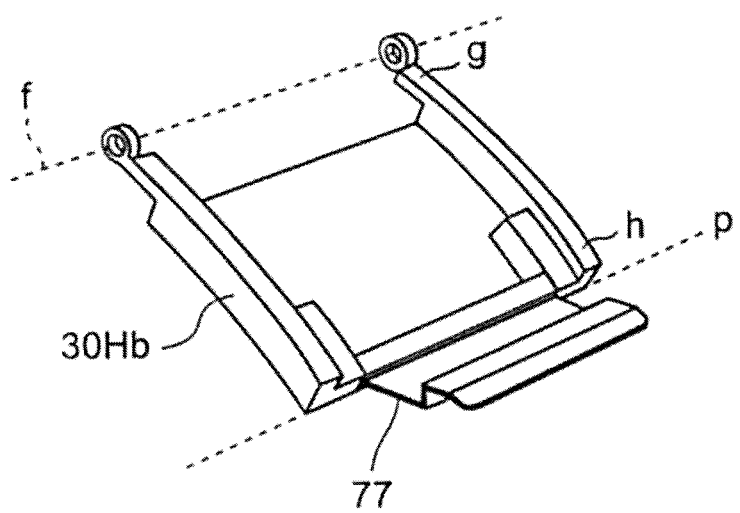
FIG. 22B is a perspective view of a buckle 30H in FIG. 22A.

FIG. 22A is a perspective view at a time when a bodily information measurement apparatus 1I according to Modified Example 4 of the fourth embodiment of the present invention is attached by being wrapped around the measurement site. FIG. 22B is a perspective view of a buckle 30H in FIG. 22A. FIG. 22B shows a surface that comes into contact with the belt 20G when the bodily information measurement apparatus 1I is attached by being wrapped around the measurement site.

In comparison to the bodily information measurement apparatus 1E shown in FIG. 18A, the bodily information measurement apparatus 1I shown in FIG. 22A differs in that the buckle 3014 is included instead of the buckle 30D and a belt 20G is included instead of the belt 20C.

As shown in FIG. 22A, in comparison to the belt 20C according to the fourth embodiment, the belt 20G according to the present modified example differs in that a sub-belt portion 69 that is divided in two in the thickness direction on the leading end portion b side of the belt 20G is further included instead of the recessed engaged portions 25A. As will be described below, it is possible to adjust the length of the belt 20G by folding the second plate-shaped member 77 in the sub-belt portion 69 and fixing it.

As shown in FIG. 22B, in comparison to the buckle 30D according to the fourth embodiment, the buckle 30H according to the present modified example differs in that a first plate-shaped member 30Hb is included instead of the first plate-shaped member 30Db. As shown in FIGS. 22A and 22B, in comparison to the first plate-shaped member 30Db, the first plate-shaped member 30Hb differs in that a second plate-shaped member 77 that is attached to the other end portion h of the first plate-shaped member 30 Hb so as to be able to rotate about an axis p that is parallel to the axis f is included instead of the fastening screws 32C.

As shown in FIG. 22A, when the second plate-shaped member 77 is arranged so as to fold up between the first plate-shaped member 30Hb and the belt 20G, the second plate-shaped member 77 prevents sliding and can fix the first plate-shaped member 30Hb to the belt 20G In other words, the second plate-shaped member 77 serves as a member for fixing the sub-belt portion 69.

The above-described embodiments are merely exemplary, and various modifications are possible without departing from the scope of the invention. The above-described multiple embodiments can be achieved independently, but the embodiments can also be combined. Also, the various characteristics in the different embodiments can be achieved independently, and the characteristics in the different embodiments can also be combined.

REFERENCE NUMERALS LIST 1 to 1I Bodily information measurement apparatus
10 Main body
16 Pressure sensor
17 Piezoelectric pump
18 Valve
20 to 20G Belt
22 Fluid bladder
23 Reinforcing layer
24 Outer circumferential layer
25, 25A Engaged portion
25B, 25C Cavity portion
29 Sheet
30 to 30H Buckle
30a First plate frame member
30b, 30Ab, 30Bb, 30Cb Second plate frame member
30Db, 30Eb, 30Fb, 30Gb, 30Hb First plate-shaped member
31 Protruding portion
31A, 31B, 32, 32A Engaging portion
32B, 32C, 32D Fastening screw
33 Magnet
34 to 34B Hook portion
36 Plate portion
38 Nipple
39 Air tube
50 Display device
51 Memory
52 Operation portion
52A Power source switch
52B Blood pressure measurement switch
53 Power source unit
66 Cap member
77 Second plate-shaped member
160 Oscillation circuit
170 Pump driving circuit
180 Valve driving circuit
100 CPU
200 Latch mechanism

The invention claimed is:

1. A bodily information measurement apparatus that is to be attached by being wrapped around a rod-shaped measurement site, wherein the rod-shaped measurement site is a limb, the bodily information measurement apparatus comprising:
   a band-shaped belt that is to be wrapped around the measurement site;
   a main body that is arranged at a base end portion in a lengthwise direction of the belt and on which an element configured to measure bodily information is mounted;
   a fluid bladder for compressing the measurement site during blood pressure measurement arranged on an inner side of the main body and an inner side of the belt in the lengthwise direction; and
   a buckle for joining the base end portion and a leading end portion on an opposite side in the lengthwise direction of the belt such that the belt forms a loop shape,
   wherein the buckle includes, on an inner surface side of the base end portion of the belt, a first plate frame member that is attached at one end portion so as to be able to rotate about a first axis that intersects the lengthwise direction of the belt, the first plate frame member extending in a plate shape from the one end portion to another end portion on the opposite side,
   wherein on the other end portion of the first plate frame member, the buckle includes a second plate frame member that is attached at the one end portion so as to be able to rotate about a second axis that is parallel to the first axis, the second plate frame member extending in a plate shape from the one end portion to the other end portion on the side opposite thereto, and the other end portion of the second plate frame member is configured to be attachable to the leading end portion of the belt,
   wherein the first plate frame member and the second plate frame member include a first opening portion and a second opening portion that penetrate through the respective members with respect to a plate surface,
   wherein in a state in which the inner surface of the main body, the first plate frame member of the buckle, and the second plate frame member of the buckle are folded so as to overlap, the first opening portion of the first plate frame member and the second opening portion of the second plate frame member are continuous in a thickness direction of the main body,
   wherein, when folded so as to overlap, the first plate member and the second plate member are approximately in a U-shape, and
   wherein the fluid bladder is removable from the belt, and the fluid bladder is in communication with the inside of the main body through a region corresponding to the first opening portion and the second opening portion in the folded state such that, during blood pressure measurement, a region of the measurement site that is spatially continuous from a portion of the fluid bladder corresponding to the inner side of the main body to the leading end portion of the belt is compressed in a circumferential direction by the fluid bladder.

2. The bodily information measurement apparatus according to claim 1, comprising
   a sticking mechanism that causes the inner surface side of the base end portion of the belt or the one end portion of the first plate frame member and the other end portion of the second plate frame member to stick together, or a lock mechanism that causes the inner surface side of the base end portion of the belt or the one end portion of the first plate frame member and the other end portion of the second plate frame member to engage with each other.

3. The bodily information measurement apparatus according to claim 1,
   wherein the first opening portion opens toward the other end portion side of the first plate frame member, the second opening portion opens toward the one end portion side of the second plate frame member, and the first opening portion and the second opening portion are in communication.

4. The bodily information measurement apparatus according to claim 3,
   wherein the fluid bladder extends in the lengthwise direction to the leading end portion of the belt, and
   wherein in the folded state, the portion of the main body with which the fluid bladder is in communication overlaps with the portion of the belt in which the fluid bladder is present.

5. The bodily information measurement apparatus according to claim 1,
   wherein a first fixing element is provided on the inner surface of the other end portion of the second plate frame member, and a second fixing element is provided on the outer surface of the leading end portion of the belt, and
   wherein the first fixing element and the second fixing element are configured to be able to engage with each other.

6. The bodily information measurement apparatus according to claim 5,
   wherein the first fixing element has one of a recessed shape and a protruding shape, and
   wherein the second fixing element has the other of the recessed shape and the protruding shape.

7. The bodily information measurement apparatus according to claim 5,
   wherein the first fixing element is a screw, and the second fixing element is a recessed portion or a cavity portion that receives the screw.

8. The bodily information measurement apparatus according to claim 5,
   wherein a plurality of said second fixing elements are formed in alignment in the lengthwise direction of the belt so as to enable adjustment of the attachment position of the other end portion of the second plate frame member in the lengthwise direction of the belt.

9. The bodily information measurement apparatus according to claim 8,
   wherein a plurality of said second fixing elements are formed in alignment in the width direction of the belt.

10. The bodily information measurement apparatus according to claim 5,
    wherein at least the outer surface of the leading end portion of the belt is composed of a flexible material.

11. The bodily information measurement apparatus according to claim 5, further comprising:
    at least one hook portion that is formed on the other end portion of the second plate frame member,
    wherein the leading end portion of the belt is formed so as to be wide in the width direction, which is perpendicular to the lengthwise direction of the belt, such that the leading end portion of the hook portion is caught and locked.

12. The bodily information measurement apparatus according to claim 11,
   wherein a third fixing element is provided on a side surface of the hook portion, and a fourth fixing element is provided on a side surface of the leading end portion of the belt, and
   wherein the third fixing element and the fourth fixing element are configured to be able to engage with each other.

13. The bodily information measurement apparatus according to claim 12,
   wherein the third fixing element is a screw, and the fourth fixing element is a recessed portion or a cavity portion that receives the screw.

14. The bodily information measurement apparatus according to claim 5, further comprising:
   on the other end portion of the second plate frame member, a plate-shaped member that can rotate about a third axis that is parallel to the first axis.

15. The bodily information measurement apparatus according to claim 1,
   wherein a plate-shaped plate portion that can rotate about a third axis that is parallel to the first axis is formed on the other end portion of the second plate frame member,
   wherein a first fixing element is provided on the inner surface of the plate portion, and a second fixing element is provided on the outer surface of the leading end portion of the belt, and
   wherein the first fixing element and the second fixing element are configured to be able to engage with each other.

* * * * *